United States Patent [19]
Kondo et al.

[11] Patent Number: 6,124,005
[45] Date of Patent: Sep. 26, 2000

[54] FLUORO-SUBSTITUTED ALKYL ETHER COMPOUNDS, LIQUID CRYSTAL COMPOSITIONS AND LIQUID CRYSTAL DISPLAY DEVICES

[75] Inventors: Tomoyuki Kondo; Shuichi Matsui; Kazutoshi Miyazawa; Hiroyuki Takeuchi, all of Ichihara; Fusayuki Takeshita, Sodegaura; Etsuo Nakagawa, Ichihara, all of Japan

[73] Assignee: Chisso Corporation, Osaka, Japan

[21] Appl. No.: 09/147,387

[22] PCT Filed: Jun. 6, 1997

[86] PCT No.: PCT/JP97/01936

§ 371 Date: Dec. 14, 1998

§ 102(e) Date: Dec. 14, 1998

[87] PCT Pub. No.: WO97/47576

PCT Pub. Date: Dec. 18, 1997

[30] Foreign Application Priority Data

Jun. 14, 1996 [JP] Japan ................................ 8-174347

[51] Int. Cl.⁷ ............................ C09K 19/34; G02F 1/13; C07C 19/06
[52] U.S. Cl. ................ 428/1.1; 252/299.01; 252/299.61; 252/299.66; 549/369; 549/374; 570/144
[58] Field of Search .................. 252/299.01, 299.63, 252/299.61, 299.66; 428/1.1; 549/369, 374; 570/130, 131, 144

[56] References Cited

U.S. PATENT DOCUMENTS

| | | | |
|---|---|---|---|
| 5,534,187 | 7/1996 | Miyazawa et al. | 252/299.01 |
| 5,562,858 | 10/1996 | Bartmann et al. | 252/299.66 |
| 5,670,085 | 9/1997 | Miyazawa et al. | 252/299.01 |
| 5,723,068 | 3/1998 | Hachiya et al. | 252/299.63 |

FOREIGN PATENT DOCUMENTS

| | | |
|---|---|---|
| 41 11 991 | 4/1991 | Germany . |
| 41 37 401 | 11/1991 | Germany . |
| 41 42 519 | 12/1991 | Germany . |
| 4137401 | 5/1993 | Germany . |
| 19513007 | 10/1995 | Germany . |
| 195 28 085 A 1 | 2/1996 | Germany . |
| 63-44132 | 2/1988 | Japan . |
| 63-13411 | 3/1988 | Japan . |
| 2-501311 | 5/1990 | Japan . |
| 2-233626 | 9/1990 | Japan . |
| 3-500413 | 1/1991 | Japan . |
| 6-500343 | 1/1994 | Japan . |
| 7-118184 | 5/1995 | Japan . |
| 7-316082 | 12/1995 | Japan . |
| 8-239665 | 9/1996 | Japan . |
| 9-67576 | 3/1997 | Japan . |
| WO 88/08441 | 11/1988 | WIPO . |

*Primary Examiner*—Shean C. Wu
*Attorney, Agent, or Firm*—Oblon, Spivak, McClelland, Maier & Neustadt, P.C.

[57] ABSTRACT

Liquid crystalline compounds which have excellent compatibility with other liquid crystal materials, especially at low temperatures, high voltage holding ratio, low threshold voltage, their small temperature dependency, high Δn, and broad liquid phase temperature range, the compounds being represented by formula (1)

$$Ra-A_1-Z_1-A_2-Z_2-(-A_3-Z_3-)_m-A_0-Rf \quad (1)$$

(wherein m is 0 or 1; $A_0$, $A_1$, $A_2$ and $A_3$ represent a six-membered ring, ring $A_0$ is 1,4-phenylene which may be substituted with 1 to 3 of F and/or Cl, rings $A_1$, $A_2$ and $A_3$, independently of one another, are selected from trans-1,4-cyclohexylene, 1,4-phenylene which may be substituted with one or more halogen atoms, cyclohexene-1,4-diyl or 1,3-dioxane-2,5-diyl; $Z_1$, $Z_2$ and $Z_3$ represent a bridge between the rings and independently of one another, are selected from —(CH$_2$)$_2$—, —(CH$_2$)$_4$—, —CH$_2$O—, —OCH$_2$— bonds, one or more hydrogen atoms in these bonds being optionally substituted with a halogen atom, or a single bond (—); Rf represents —OCF$_2$CF$_2$H or —OCF$_2$CFHCF$_3$; and Ra is a straight- or branched monovalent organic radical of 1 to 20 carbons); liquid crystal compositions comprising at least one of the compounds; and liquid crystal display devices composed of the compositions.

10 Claims, No Drawings

FLUORO-SUBSTITUTED ALKYL ETHER COMPOUNDS, LIQUID CRYSTAL COMPOSITIONS AND LIQUID CRYSTAL DISPLAY DEVICES

This application is a 371 of PCT/JP97/01936 filed Jun. 6, 1997.

TECHNICAL FIELD

This invention relates to liquid crystalline compounds, more specifically liquid crystalline compounds comprising new fluoro-substituted alkyl ether compounds consisting of tricyclic or tetracyclic compounds having a fluoroalkoxy group at one end, liquid crystal compositions containing said liquid crystalline compounds and liquid crystal display devices composed of said liquid crystal compositions.

The term "liquid crystalline compound" as used herein refers generically to a compound exhibiting a liquid crystal phase singly and a compound not exhibiting a liquid crystal phase singly but having a liquid crystal phase potentially as a constitutional component for a liquid crystal composition.

BACKGROUND ART

Display devices using liquid crystalline compounds have been extensively used in the display for watches, calculators, word processors and so forth. These display devices are those utilizing optical anisotropy, dielectric anisotropy, etc. of liquid crystalline compounds. Liquid crystal phases include a nematic phase, a smectic phase and a cholesteric phase, but display devices utilizing the nematic phase have been most extensively used. Display modes include a dynamic scattering (DS) mode, a deforming of aligned phases (DAP) mode, a guest-host (GH) mode, a twisted nematic (TN) mode, a supertwisted nematic (STN) mode, a thin film transistor (TFT) mode and the like.

Liquid crystalline compounds used for these display modes should exhibit liquid crystal phases within a broad temperature range around room temperature, have a sufficient stability under conditions where the display devices are used, and also have sufficient characteristics for driving the display devices, but at present, no single liquid crystalline compound satisfying these conditions has been found. Therefore, the fact is that several kinds to dozens of kinds of liquid crystalline compounds have been blended to prepare liquid crystal compositions furnished with the required characteristics. These liquid crystal compositions are required to be stable to moisture, light, heat and air which are usually present under conditions where the display devices are used, to be also stable to electric field or electromagnetic irradiation, and moreover, to be chemically stable to the blended compounds. It is further required for the liquid crystal compositions that values of various physical properties such as optical anisotropy value ($\Delta n$), dielectric anisotropy value ($\Delta \epsilon$), etc. are suitable, depending upon the display mode and the shape of the display devices. Furthermore, it is important for the respective components in the liquid crystal compositions to have good compatibility.

In recent years, a TFT type display having characteristics such as high contrast, broad view angle or the like has been studied extensively. Liquid crystal compositions for TFT have required such physical properties as high voltage holding ratio, small temperature dependency of the ratio, broad liquid crystal phase temperature range, low threshold voltage (Vth), small temperature dependency of the voltage, good compatibility with other liquid crystal materials or low viscosity. Alternatively, the compositions having high $\Delta n$ are also useful to improve the response rate.

For this purpose, suitable is a polycyclic compound containing at its end rings substituted with a fluorine atom or a fluoro-substituted alkyl group, many syntheses and studies of which have been done extensively.

For instance, Japanese Patent Publication No. Sho 63-13411 discloses tricyclic compounds containing a fluorophenyl group at the terminal, Japanese Patent Publication No. Sho 63-44132 discloses tricyclic compounds containing a difluorophenyl group at the terminal, Japanese Patent Kokai No. Hei 2-233626 discloses di- to tetra-cyclic compounds containing a trifluorophenyl group, Japanese Patent Publication No. Hei 3-500413 discloses polycyclic compounds containing a difluoromethoxyphenyl group, and Japanese Patent Publication No. Hei 2-501311 discloses polycyclic compounds containing a trifluoromethoxyphenyl group. Each of the above publications also discloses liquid crystal compositions containing such compounds.

DE 4111991 discloses polycyclic compounds containing a fluoroethoxyphenyl group at the terminal, DE 4137401 and DE 4142519 disclose polycyclic compounds containing a fluoropropoxyphenyl group, the claims of which include a great number of compounds, but the compounds as concretely synthesized or illustrated are a very limited number of compounds comprising a combination of the specified ring and bridge.

An object of the present invention is to provide a liquid crystalline compound having exceedingly high voltage holding ratio, exceedingly small temperature dependency of the ratio, low threshold voltage, high $\Delta n$ and excellent compatibility with other liquid crystal materials, especially at low temperatures, a liquid crystal composition containing said compound as a constituent and a liquid crystal display device composed of said liquid crystal composition.

As a result of our intensive studies to achieve the above object, it was found surprisingly that a group of compounds included within the claims of said DE patents, but not illustrated concretely therein satisfy various characteristics required for said liquid crystalline compounds and have excellent compatibility with other liquid crystalline compounds, especially at low temperatures, thus leading to completion of the present invention.

DISCLOSURE OF THE INVENTION

The invention is directed to a liquid crystalline compound comprising a fluoro-substituted alkyl ether compound represented by formula (1)

$$\text{Ra} - A_1 - Z_1 - A_2 - Z_2 - (-A_3 - Z_3 -)_m - A_0 - \text{Rf} \qquad (1)$$

wherein m is 0 or 1; $A_0$, $A_1$, $A_2$ and $A_3$ represent a six-membered ring, ring $A_0$ is 1,4-phenylene which may be substituted with 1 to 3 of F and/or Cl, rings $A_1$, $A_2$ and $A_3$, independently of one another, are selected from trans-1,4-cyclohexylene, 1,4-phenylene which may be substituted with one or more halogen atoms, cyclohexene-1,4-diyl or 1,3-dioxane-2,5-diyl; $Z_1$, $Z_2$ and $Z_3$ represent a bridge between the rings and independently of one another, are selected from —$(CH_2)_2$—, —$(CH_2)_4$—, —$CH_2O$—, —$OCH_2$— bonds, one or more hydrogen atoms in these bonds being optionally substituted with a halogen atom, or a single bond; Rf represents —$OCF_2CF_2H$ or —$OCF_2CFHCF_3$; and Ra is selected from a straight- or branched monovalent organic radical of 1 to 20 carbons in which one or more hydrogen atoms in the radical may be substituted with a halogen atom and/or a cyano group, and in which one or more of —O—, —S—, —CO—, —CH=CH— or an ethynylene bond may be inserted in the radical, but two or more —O— and/or —S— are not adjacent to one another.

The present invention is also directed to a liquid crystal composition comprising at least one of the said liquid crystalline compounds, preferably a liquid crystal composition comprising at least one of the compounds represented by formula (2)

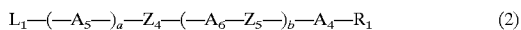
(2)

wherein a is 1 or 2, b is 0 or 1; $A_4$, $A_5$ and $A_6$ represent a six-membered ring, ring $A_4$ is 1,4-phenylene which may be substituted with one or two fluorine atoms, ring $A_5$ is trans-1,4-cyclohexylene, ring $A_6$ is trans-1,4-cyclohexylene, or 1,4-phenylene which may be substituted with one or more fluorine atoms; $Z_4$ and $Z_5$ represent a bridge between the rings and independently of one another, are selected from a single bond, —(CH$_2$)$_2$— or —CH=CH—; $R_1$ is selected from F, Cl, —OCF$_3$, —OCF$_2$H, —CF$_3$, —CF$_2$H or —CFH$_2$; and $L_1$ is an alkyl group of 1–10 carbons; and/or at least one of the compounds represented by formula (3)

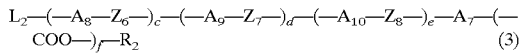
(3)

wherein c, d, e and f are independently of one another 0 or 1; $A_7$, $A_8$, $A_9$ and $A_{10}$ represent a six-membered ring, ring $A_7$ is trans-1,4-cyclohexylene or 1,4-phenylene which may be substituted with one or more fluorine atoms, rings $A_8$, $A_9$ and $A_{10}$, independently of one another, are selected from trans-1,4-cyclohexylene, 1,4-phenylene which may be substituted with one or more halogen atoms, cyclohexene-1,4-diyl, 1,3-dioxane-2,5-diyl or pyrimidine-2,5-diyl; $Z_6$, $Z_7$ and $Z_8$ represent a bridge between the rings and independently of one another, are selected from a single bond, —(CH$_2$)$_2$—, —COO—, —CH=CH—, ethynylene or 1-butene-3-ynylene; $R_2$ is selected from F, —OCF$_3$, —OCF$_2$H, —CF$_3$, —CF$_2$H, —CFH$_2$, —CN, a monovalent saturated organic radical of 1–10 carbons which may have one or more non-adjacent —O— in the radical, and a monovalent unsaturated organic radical of 2–10 carbons having —CH=CH at the terminal of the radical and/or in the radical in which one or more non-adjacent —O— may be inserted in the radical; $L_2$ is selected from a fluorine atom, a monovalent saturated organic radical of 1–10 carbons which may have one or more non-adjacent —O— in the radical, and a monovalent unsaturated organic radical of 2–10 carbons having —CH=CH— at the terminal of the radical and/or in the radical in which one or more non-adjacent —O— may be inserted in the radical; and to a liquid crystal display device using these liquid crystal compositions.

BEST FORM FOR CARRYING OUT THE INVENTION

The fluoro-substituted alkyl ether compounds represented by formula (1) according to the present invention include tricyclic and tetracyclic compounds which have a 1,1,2,2-tetrafluoroethoxy group or a 1,1,2,3,3,3-hexafluoropropoxy group at one end, as represented by formula (1A)

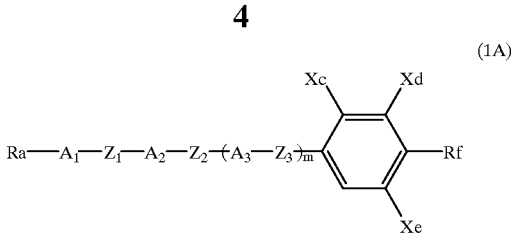
(1A)

wherein Ra, Rf, $A_1$, $A_2$, $A_3$, $Z_1$, $Z_2$, $Z_3$ and m have the same meanings as defined above, and Xc, Xd and Xe are independently of one another H, F or Cl. The present invention also includes a compound wherein one or more atoms in the chain are substituted by isotopes thereof.

In formula (1), rings $A_1$, $A_2$ and $A_3$, independently of one another, are selected from trans-1,4-cyclohexylene, 1,4-phenylene which may be substituted with one or more halogen atoms, cyclohexene-1,4-diyl or 1,3-dioxane-2,5-diyl, but preferably, these rings do not contain two or more heterocycles. $Z_1$, $Z_2$ and $Z_3$ which are a bridge between these rings, independently of one another, are selected from —(CH$_2$)$_2$—, —(CH$_2$)$_4$—, —CH$_2$O—, —OCH$_2$— bonds, one or more hydrogen atoms in these bonds being optionally substituted with a halogen atom, or a single bond (—).

The fluoro-substituted alkyl ether compounds represented by formula (1) according to the present invention can be roughly classified into compounds having three 6-membered rings wherein m is 0, and compounds having four 6-membered rings wherein m is 1, and further divided into the following classes according to the combination of the bridges between the rings.

In the following examples, Rf, Ra, $A_0$, $A_1$, $A_2$ and $A_3$, and $Z_1$, $Z_2$ and $Z_3$ unless stated otherwise have the same meanings as defined above. Compounds having three 6-membered rings:

 (1-1a)

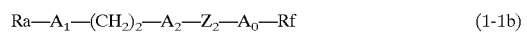 (1-1b)

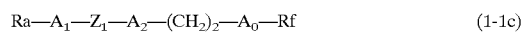 (1-1c)

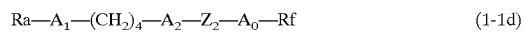 (1-1d)

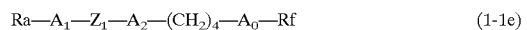 (1-1e)

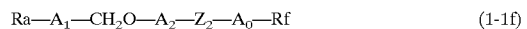 (1-1f)

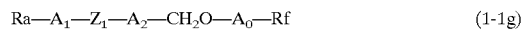 (1-1g)

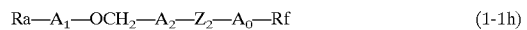 (1-1h)

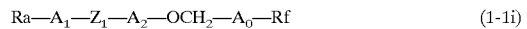 (1-1i)

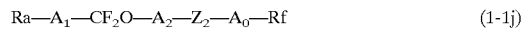 (1-1j)

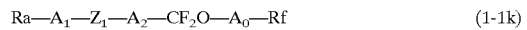 (1-1k)

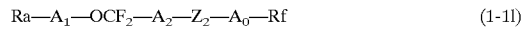 (1-1l)

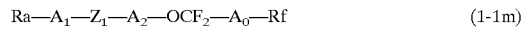 (1-1m)

Compounds having four 6-membered rings:

 (1-2a)

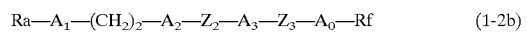 (1-2b)

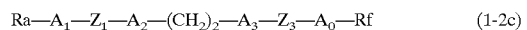 (1-2c)

 (1-2d)

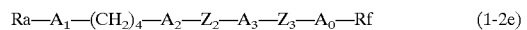 (1-2e)

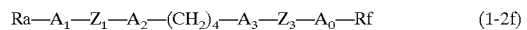 (1-2f)

Ra—A₁—Z₁—A₂—Z₂—A₃—(CH₂)₄—A₀—Rf        (1-2g)

Ra—A₁—CH₂O—A₂—Z₂—A₃—Z₃—A₀—Rf          (1-2h)

Ra—A₁—Z₁—A₂—CH₂O—A₃—Z₃—A₀—Rf          (1-2i)

Ra—A₁—Z₁—A₂—Z₂—A₃—CH₂O—A₀—Rf          (1-2j)

Ra—A₁—OCH₂—A₂—Z₂—A₃—Z₃—A₀—Rf          (1-2k)

Ra—A₁—Z₁—A₂—OCH₂—A₃—Z₃—A₀—Rf          (1-2l)

Ra—A₁—Z₁—A₂—Z₂—A₃—OCH₂—A₀—Rf          (1-2m)

Ra—A₁—CF₂O—A₂—Z₂—A₃—Z₃—A₀—Rf          (1-2n)

Ra—A₁—Z₁—A₂—CF₂O—A₃—Z₃—A₀—Rf          (1-2o)

Ra—A₁—Z₁—A₂—Z₂—A₃—CF₂O—A₀—Rf          (1-2p)

Ra—A₁—OCF₂—A₂—Z₂—A₃—Z₃—A₀—Rf          (1-2q)

Ra—A₁—Z₁—A₂—OCF₂—A₃—Z₃—A₀—Rf          (1-2r)

Ra—A₁—Z₁—A₂—Z₂—A₃—OCF₂—A₀—Rf          (1-2s)

The fluoro-substituted alkyl ether compounds of the present invention are further divided into the following classes according to the combination and order of rings $A_1$, $A_2$ and $A_3$, and each of these compounds can be used preferably as a liquid crystalline compound and as a component of liquid crystal compositions.

In the following examples, "Hx" represents a trans-1,4-cyclohexylene group, "Be(nX)" represents a 1,4-phenylene group in which the number "n" of hydrogen atoms may be substituted with halogen atoms, "Ch" represents a cyclohexene-1,4-diyl group, and "Do" represents a 1,3-dioxane-2,5-diyl group.

Of the compounds represented by formula (1-1a), the following compounds represented by formulae (1aa) to (1ae) are especially preferable as a liquid crystalline compound.

Ra—Be(nX)—Be(nX)—A₀—Rf               (1aa)

Ra—Ch—Be(nX)—A₀—Rf                   (1ab)

Ra—Do—Be(nX)—A₀—Rf                   (1ac)

Ra—Ch—Ch—A₀—Rf                       (1ad)

Ra—Ch—Do—A₀—Rf                       (1ae)

Of the compounds represented by formula (1-1b), the following compounds represented by formulae (1ba) to (1be) are especially preferable as a liquid crystalline compound.

Ra—Be(nX)—(CH₂)₂—Be(nX)—A₀—Rf        (1ba)

Ra—Ch—(CH₂)₂—Be(nX)—A₀—Rf            (1bb)

Ra—Do—(CH₂)₂—Be(nX)—A₀—Rf            (1bc)

Ra—Ch—(CH₂)₂—Ch—A₀—Rf                (1bd)

Ra—Be(nX)—(CH₂)₂—Do—A₀—Rf            (1be)

Of the compounds represented by formula (1-1c), the following compounds represented by formulae (1ca) to (1cc) are especially preferable as a liquid crystalline compound.

Ra—Be(nX)—Be(nX)—(CH₂)₂—A₀—Rf        (1ca)

Ra—Ch—Be(nX)—(CH₂)₂—A₀—Rf            (1ab)

Ra—Do—Be(nX)—(CH₂)₂—A₀—Rf            (1cc)

Of the compounds represented by formula (1-1d), the following compounds represented by formulae (1da) to (1de) are especially preferable as a liquid crystalline compound.

Ra—Be(nX)—(CH₂)₄—Be(nX)—A₀—Rf        (1da)

Ra—Ch—(CH₂)₄—Be(nX)—A₀—Rf            (1db)

Ra—Do—(CH₂)₄—Be(nX)—A₀—Rf            (1dc)

Ra—Be(nX)—(CH₂)₄—Ch—A₀—Rf            (1dd)

Ra—Be(nX)—(CH₂)₄—Do—A₀—Rf            (1de)

Of the compounds represented by formula (1-1e), the following compounds represented by formulae (1ea) to (1ec) are especially preferable as a liquid crystalline compound.

Ra—Be(nX)—Be(nX)—(CH₂)₄—A₀—Rf        (1ea)

Ra—Ch—Be(nX)—(CH₂)₄—A₀—Rf            (1eb)

Ra—Do—Be(nX)—(CH₂)₄—A₀—Rf            (1ec)

Of the compounds represented by formula (1-1f), the following compounds represented by formulae (1fa) to (1fe) are especially preferable as a liquid crystalline compound.

Ra—Be(nX)—CH₂O—Be(nX)—A₀—Rf          (1fa)

Ra—Ch—CH₂O—Be(nX)—A₀—Rf              (1fb)

Ra—Do—CH₂O—Be(nX)—A₀—Rf              (1fc)

Ra—Be(nX)—CH₂O—Ch—A₀—Rf              (1fd)

Ra—Be(nX)—CH₂O—Do—A₀—Rf              (1fe)

Of the compounds represented by formula (1-1g), the following compounds represented by formulae (1ga) to (1gc) are especially preferable as a liquid crystalline compound.

Ra—Be(nX)—Be(nX)—CH₂O—A₀—Rf          (1ga)

Ra—Ch—Be(nX)—CH₂O—A₀—Rf              (1gb)

Ra—Do—Be(nX)—CH₂O—A₀—Rf              (1gc)

Of the compounds represented by formula (1-1j), the following compounds represented by formulae (1ja) to (1je) are especially preferable as a liquid crystalline compound.

Ra—Be(nX)—CF₂O—Be(nX)—A₀—Rf          (1ja)

Ra—Ch—CF₂O—Be(nX)—A₀—Rf              (1jb)

Ra—Do—CF₂O—Be(nX)—A₀—Rf              (1jc)

Ra—Be(nX)—CF₂O—Ch—A₀—Rf              (1jd)

Ra—Be(nX)—CF₂O—Do—A₀—Rf              (1je)

Of the compounds represented by formula (1-1k), the following compounds represented by formulae (1ka) to (1kc) are especially preferable as a liquid crystalline compound.

Ra—Be(nX)—Be(nX)—CF₂O—A₀—Rf          (1ka)

Ra—Ch—Be(nX)—CF₂O—A₀—Rf              (1kb)

Ra—Do—Be(nX)—CF₂O—A₀—Rf              (1kc)

Of the compounds represented by formula (1-2a), the following compounds represented by formulae (2aa) to (2ai) are especially preferable as a liquid crystalline compound.

$$Ra\text{—}Be(nX)\text{—}Be(nX)\text{—}Be(nX)\text{—}A_0\text{—}Rf \quad (2aa)$$

$$Ra\text{—}Hx\text{—}Be(nX)\text{—}Be(nX)\text{—}A_0\text{—}Rf \quad (2ab)$$

$$Ra\text{—}Hx\text{—}Hx\text{—}Be(nX)\text{—}A_0\text{—}Rf \quad (2ac)$$

$$Ra\text{—}Hx\text{—}Hx\text{—}Hx\text{—}A_0\text{—}Rf \quad (2ad)$$

$$Ra\text{—}Ch\text{—}Be(nX)\text{—}Be(nX)\text{—}A_0\text{—}Rf \quad (2ae)$$

$$Ra\text{—}Hx\text{—}Ch\text{—}Be(nX)\text{—}A_0\text{—}Rf \quad (2af)$$

$$Ra\text{—}Hx\text{—}Hx\text{—}Ch\text{—}A_0\text{—}Rf \quad (2ag)$$

$$Ra\text{—}Hx\text{—}Do\text{—}Be(nX)\text{—}A_0\text{—}Rf \quad (2ah)$$

$$Ra\text{—}Hx\text{—}Hx\text{—}Do\text{—}A_0\text{—}Rf \quad (2ai)$$

Of the compounds represented by formula (1-2b), the following compounds represented by formulae (2ba) to (2bf) are especially preferable as a liquid crystalline compound.

$$Ra\text{—}Be(nX)\text{—}(CH_2)_2\text{—}Be(nX)\text{—}Be(nX)\text{—}A_0\text{—}Rf \quad (2ba)$$

$$Ra\text{—}Hx\text{—}(CH_2)_2\text{—}Be(nX)\text{—}Be(nX)\text{—}A_0\text{—}Rf \quad (2bb)$$

$$Ra\text{—}Hx\text{—}(CH_2)_2\text{—}Hx\text{—}Be(nX)\text{—}A_0\text{—}Rf \quad (2bc)$$

$$Ra\text{—}Hx\text{—}(CH_2)_2\text{—}Hx\text{—}Hx\text{—}A_0\text{—}Rf \quad (2bd)$$

$$Ra\text{—}Hx\text{—}(CH_2)_2\text{—}Ch\text{—}Be(nX)\text{—}A_0\text{—}Rf \quad (2be)$$

$$Ra\text{—}Hx\text{—}(CH_2)_2\text{—}Hx\text{—}Do\text{—}A_0\text{—}Rf \quad (2bf)$$

Of the compounds represented by formula (1-2c), the following compounds represented by formulae (2ca) to (2ch) are especially preferable as a liquid crystalline compound.

$$Ra\text{—}Be(nX)\text{—}Be(nX)\text{—}(CH_2)_2\text{—}Be(nX)\text{—}A_0\text{—}Rf \quad (2ca)$$

$$Ra\text{—}Hx\text{—}Be(nX)\text{—}(CH_2)_2\text{—}Be(nX)\text{—}A_0\text{—}Rf \quad (2cb)$$

$$Ra\text{—}Hx\text{—}Hx\text{—}(CH_2)_2\text{—}Be(nX)\text{—}A_0\text{—}Rf \quad (2cc)$$

$$Ra\text{—}Hx\text{—}Hx\text{—}(CH_2)_2\text{—}Hx\text{—}A_0\text{—}Rf \quad (2cd)$$

$$Ra\text{—}Be(nX)\text{—}Hx\text{—}(CH_2)_2\text{—}Be(nX)\text{—}A_0\text{—}Rf \quad (2ce)$$

$$Ra\text{—}Hx\text{—}Ch\text{—}(CH_2)_2\text{—}Be(nX)\text{—}A_0\text{—}Rf \quad (2cf)$$

$$Ra\text{—}Hx\text{—}Hx\text{—}(CH_2)_2\text{—}Ch\text{—}A_0\text{—}Rf \quad (2cg)$$

$$Ra\text{—}Hx\text{—}Hx\text{—}(CH_2)_2\text{—}Do\text{—}A_0\text{—}Rf \quad (2ch)$$

Of the compounds represented by formula (1-2d), the following compounds represented by formulae (2da) to (2de) are especially preferable as a liquid crystalline compound.

$$Ra\text{—}Be(nX)\text{—}Be(nX)\text{—}Be(nX)\text{—}(CH_2)_2\text{—}A_0\text{—}Rf \quad (2da)$$

$$Ra\text{—}Hx\text{—}Be(nX)\text{—}Be(nX)\text{—}(CH_2)_2\text{—}A_0\text{—}Rf \quad (2db)$$

$$Ra\text{—}Hx\text{—}Hx\text{—}Be(nX)\text{—}(CH_2)_2\text{—}A_0\text{—}Rf \quad (2dc)$$

$$Ra\text{—}Hx\text{—}Hx\text{—}Hx\text{—}(CH_2)_2\text{—}A_0\text{—}Rf \quad (2dd)$$

$$Ra\text{—}Hx\text{—}Ch\text{—}Be(nX)\text{—}(CH_2)_2\text{—}A_0\text{—}Rf \quad (2de)$$

Of the compounds represented by formula (1-2e), the following compounds represented by formulae (2ea) to (2ef) are especially preferable as a liquid crystalline compound.

$$Ra\text{—}Be(nX)\text{—}(CH_2)_4\text{—}Be(nX)\text{—}Be(nX)\text{—}A_0\text{—}Rf \quad (2ea)$$

$$Ra\text{—}Hx\text{—}(CH_2)_4\text{—}Be(nX)\text{—}Be(nX)\text{—}A_0\text{—}Rf \quad (2eb)$$

$$Ra\text{—}Hx\text{—}(CH_2)_4\text{—}Hx\text{—}Be(nX)\text{—}A_0\text{—}Rf \quad (2ec)$$

$$Ra\text{—}Hx\text{—}(CH_2)_4\text{—}Hx\text{—}Hx\text{—}A_0\text{—}Rf \quad (2ed)$$

$$Ra\text{—}Hx\text{—}(CH_2)_4\text{—}Ch\text{—}Be(nX)\text{—}A_0\text{—}Rf \quad (2ee)$$

$$Ra\text{—}Hx\text{—}(CH_2)_4\text{—}Hx\text{—}Do\text{—}A_0\text{—}Rf \quad (2ef)$$

Of the compounds represented by formula (1-2f), the following compounds represented by formulae (2fa) to (2fg) are especially preferable as a liquid crystalline compound.

$$Ra\text{—}Be(nX)\text{—}Be(nX)\text{—}(CH_2)_4\text{—}Be(nX)\text{—}A_0\text{—}Rf \quad (2fa)$$

$$Ra\text{—}Hx\text{—}Be(nX)\text{—}(CH_2)_4\text{—}Be(nX)\text{—}A_0\text{—}Rf \quad (2fb)$$

$$Ra\text{—}Hx\text{—}Hx\text{—}(CH_2)_4\text{—}Be(nX)\text{—}A_0\text{—}Rf \quad (2fc)$$

$$Ra\text{—}Hx\text{—}Hx\text{—}(CH_2)_4\text{—}Hx\text{—}A_0\text{—}Rf \quad (2fd)$$

$$Ra\text{—}Be(nX)\text{—}Hx\text{—}(CH_2)_4\text{—}Be(nX)\text{—}A_0\text{—}Rf \quad (2fe)$$

$$Ra\text{—}Hx\text{—}Hx\text{—}(CH_2)_4\text{—}Ch\text{—}A_0\text{—}Rf \quad (2ff)$$

$$Ra\text{—}Hx\text{—}Hx\text{—}(CH_2)_4\text{—}Do\text{—}A_0\text{—}Rf \quad (2fg)$$

Of the compounds represented by formula (1-2g), the following compounds represented by formulae (2ga) to (2ge) are especially preferable as a liquid crystalline compound.

$$Ra\text{—}Be(nX)\text{—}Be(nX)\text{—}Be(nX)\text{—}(CH_2)_4\text{—}A_0\text{—}Rf \quad (2ga)$$

$$Ra\text{—}Hx\text{—}Be(nX)\text{—}Be(nX)\text{—}(CH_2)_4\text{—}A_0\text{—}Rf \quad (2gb)$$

$$Ra\text{—}Hx\text{—}Hx\text{—}Be(nX)\text{—}(CH_2)_4\text{—}A_0\text{—}Rf \quad (2gc)$$

$$Ra\text{—}Hx\text{—}Hx\text{—}Hx\text{—}(CH_2)_4\text{—}A_0\text{—}Rf \quad (2gd)$$

$$Ra\text{—}Hx\text{—}Ch\text{—}Be(nX)\text{—}(CH_2)_4\text{—}A_0\text{—}Rf \quad (2ge)$$

Of the compounds represented by formula (1-2h), the following compounds represented by formulae (2ha) to (2hf) are especially preferable as a liquid crystalline compound.

$$Ra\text{—}Be(nX)\text{—}CH_2O\text{—}Be(nX)\text{—}Be(nX)\text{—}A_0\text{—}Rf \quad (2ha)$$

$$Ra\text{—}Hx\text{—}CH_2O\text{—}Be(nX)\text{—}Be(nX)\text{—}A_0\text{—}Rf \quad (2hb)$$

$$Ra\text{—}Hx\text{—}CH_2O\text{—}Hx\text{—}Be(nX)\text{—}A_0\text{—}Rf \quad (2hc)$$

$$Ra\text{—}Hx\text{—}CH_2O\text{—}Hx\text{—}Hx\text{—}A_0\text{—}Rf \quad (2hd)$$

$$Ra\text{—}Hx\text{—}CH_2O\text{—}Ch\text{—}Be(nX)\text{—}A_0\text{—}Rf \quad (2he)$$

$$Ra\text{—}Hx\text{—}CH_2O\text{—}Hx\text{—}Do\text{—}A_0\text{—}Rf \quad (2hf)$$

Of the compounds represented by formula (1-2i), the following compounds represented by formulae (2ia) to (2ig) are especially preferable as a liquid crystalline compound.

$$Ra\text{—}Be(nX)\text{—}Be(nX)\text{—}CH_2O\text{—}Be(nX)\text{—}A_0\text{—}Rf \quad (2ia)$$

$$Ra\text{—}Hx\text{—}Be(nX)\text{—}CH_2O\text{—}Be(nX)\text{—}A_0\text{—}Rf \quad (2ib)$$

$$Ra\text{—}Hx\text{—}Hx\text{—}CH_2O\text{—}Be(nX)\text{—}A_0\text{—}Rf \quad (2ic)$$

$$Ra\text{—}Hx\text{—}Hx\text{—}CH_2O\text{—}Hx\text{—}A_0\text{—}Rf \quad (2id)$$

$$Ra\text{—}Be(nX)\text{—}Hx\text{—}CH_2O\text{—}Be(nX)\text{—}A_0\text{—}Rf \quad (2ie)$$

$$Ra\text{—}Hx\text{—}Hx\text{—}CH_2O\text{—}Ch\text{—}A_0\text{—}Rf \quad (2if)$$

$$Ra\text{—}Hx\text{—}Hx\text{—}CH_2O\text{—}Do\text{—}A_0\text{—}Rf \quad (2ig)$$

Of the compounds represented by formula (1-2j), the following compounds represented by formulae (2ja) to (2je) are especially preferable as a liquid crystalline compound.

Ra—Be(nX)—Be(nX)—Be(nX)—CH$_2$O—A$_0$—Rf    (2ja)

Ra—Hx—Be(nX)—Be(nX)—CH$_2$O—A$_0$—Rf    (2jb)

Ra—Hx—Hx—Be(nX)—CH$_2$O—A$_0$—Rf    (2jc)

Ra—Hx—Hx—Hx—CH$_2$O—A$_0$—Rf    (2jd)

Ra—Hx—Ch—Be(nX)—CH$_2$O—A$_0$—Rf    (2je)

Of the compounds represented by formula (1-2n), the following compounds represented by formulae (2na) to (2nf) are especially preferable as a liquid crystalline compound.

Ra—Be(nX)—CF$_2$O—Be(nX)—Be(nX)—A$_0$—Rf    (2na)

Ra—Hx—CF$_2$O—Be(nX)—Be(nX)—A$_0$—Rf    (2nb)

Ra—Hx—CF$_2$O—Hx—Be(nX)—A$_0$—Rf    (2nc)

Ra—Hx—CF$_2$O—Hx—Hx—A$_0$—Rf    (2nd)

Ra—Hx—CF$_2$O—Ch—Be(nX)—A$_0$—Rf    (2ne)

Ra—Hx—CF$_2$O—Hx—Do—A$_0$—Rf    (2nf)

Of the compounds represented by formula (1-2o), the following compounds represented by formulae (2oa) to (2og) are especially preferable as a liquid crystalline compound.

Ra—Be(nX)—Be(nX)—CF$_2$O—Be(nX)—A$_0$—Rf    (2oa)

Ra—Hx—Be(nX)—CF$_2$O—Be(nX)—A$_0$—Rf    (2ob)

Ra—Hx—Hx—CF$_2$O—Be(nX)—A$_0$—Rf    (2oc)

Ra—Hx—Hx—CF$_2$O—Hx—A$_0$—Rf    (2od)

Ra—Be(nX)—Hx—CF$_2$O—Be(nX)—A$_0$—Rf    (2oe)

Ra—Hx—Hx—CF$_2$O—Ch—A$_0$—Rf    (2of)

Ra—Hx—Hx—CF$_2$O—Do—A$_0$—Rf    (2og)

Of the compounds represented by formula (1-2p), the following compounds represented by formulae (2pa) to (2pe) are especially preferable as a liquid crystalline compound.

Ra—Be(nX)—Be(nX)—Be(nX)—CF$_2$O—A$_0$—Rf    (2pa)

Ra—Hx—Be(nX)—Be(nX)—CF$_2$O—A$_0$—Rf    (2pb)

Ra—Hx—Hx—Be(nX)—CF$_2$O—A$_0$—Rf    (2pc)

Ra—Hx—Hx—Hx—CF$_2$O—A$_0$—Rf    (2pd)

Ra—Hx—Ch—Be(nX)—CF$_2$O—A$_0$—Rf    (2pe)

Of the above compounds which are especially preferable as a liquid crystalline compound, the following compounds represented by formulae (1-1) to (1-56) can be given as a compound which has outstandingly excellent properties.

In the formulae as shown below, Rf and Ra have the same meanings as defined above, $X_1$ and $X_2$ are independently of one another H, F or Cl, and (F) on the 1,4-phenylene ring represents the case where said ring may be substituted with F.

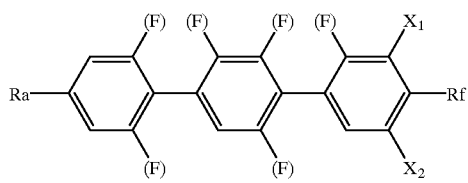

(1-1)

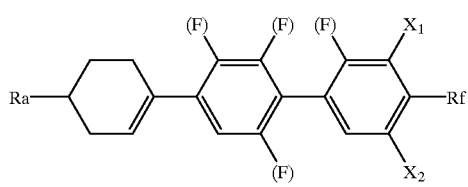

(1-2)

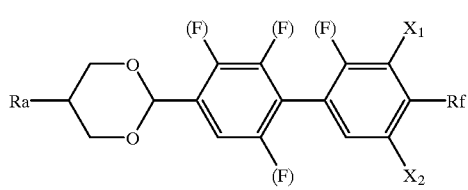

(1-3)

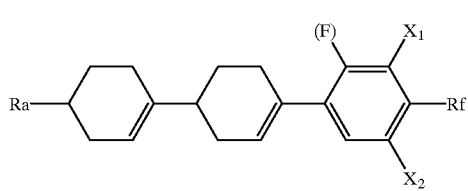

(1-4)

(1-5)
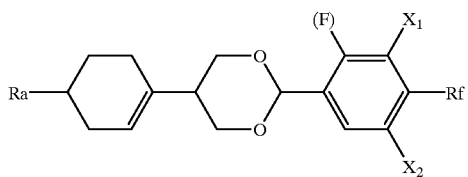
(1-6)
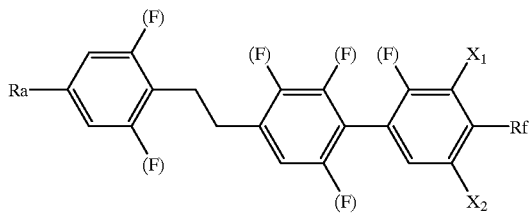
(1-7)
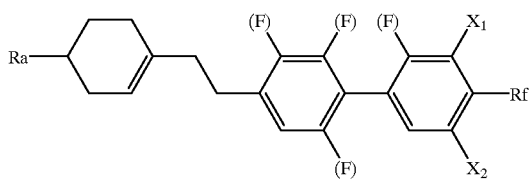
(1-8)
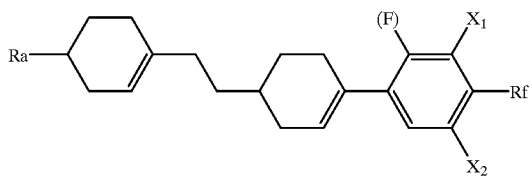
(1-9)
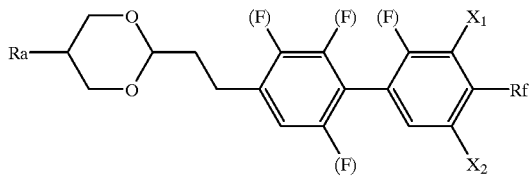
(1-10)
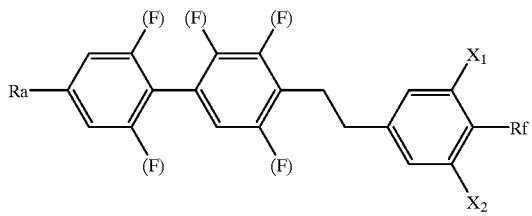
(1-11)
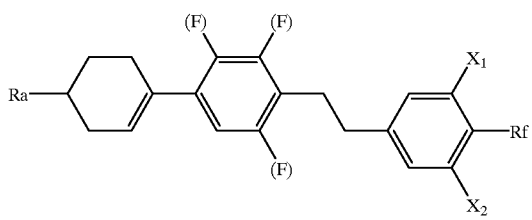

(1-12)
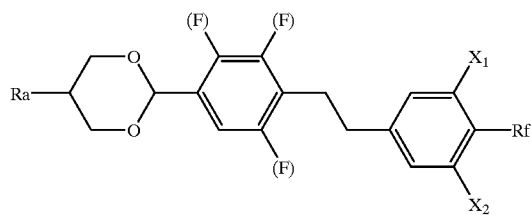
(1-13)
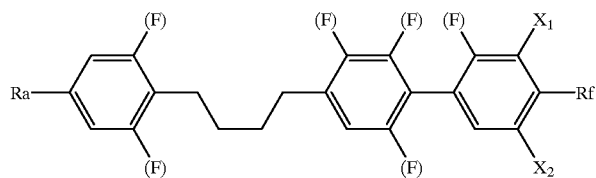
(1-14)
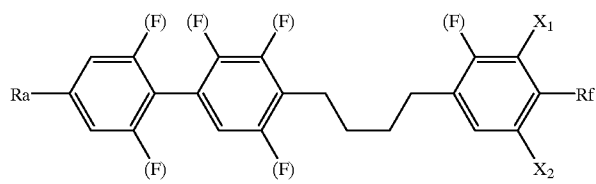
(1-15)
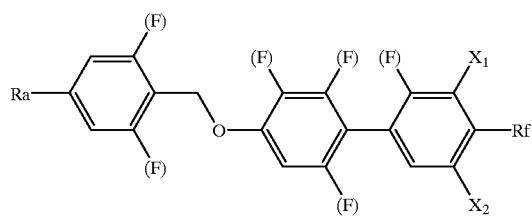
(1-16)
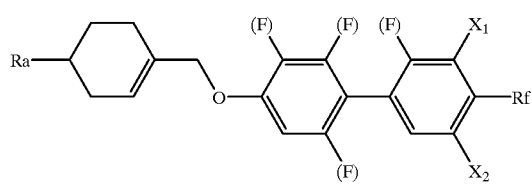
(1-17)
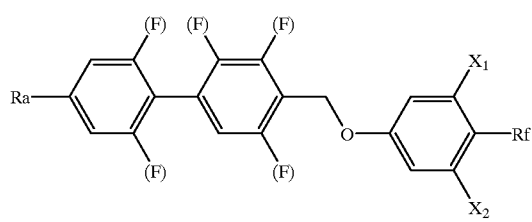
(1-18)
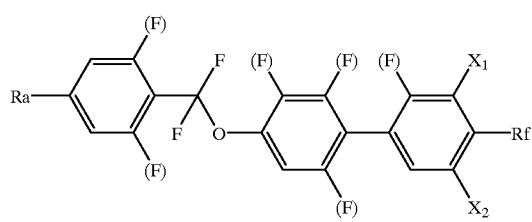

-continued
(1-19)
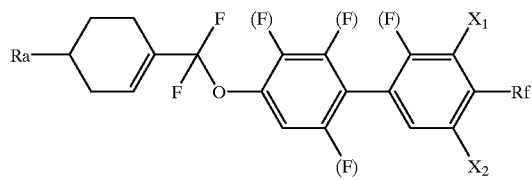
(1-20)
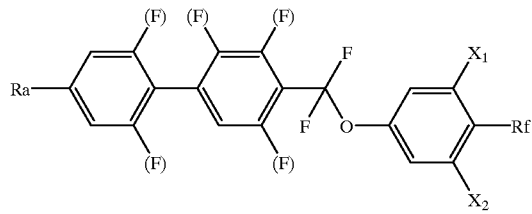
(1-21)
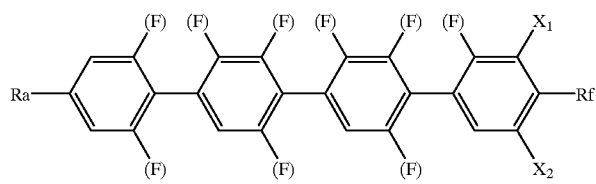
(1-22)
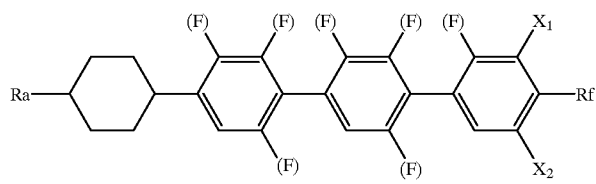
(1-23)
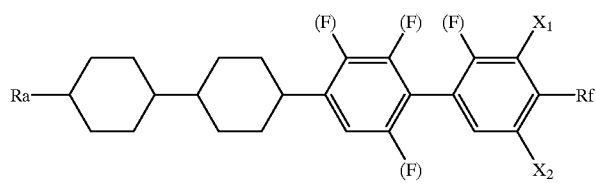
(1-24)
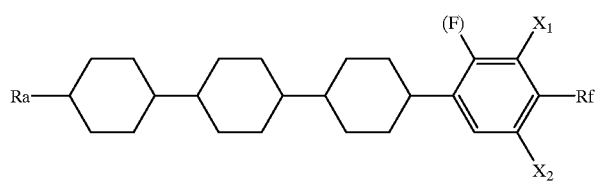
(1-25)
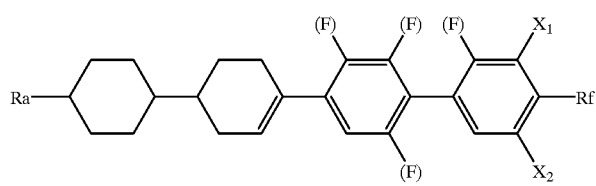
(1-26)
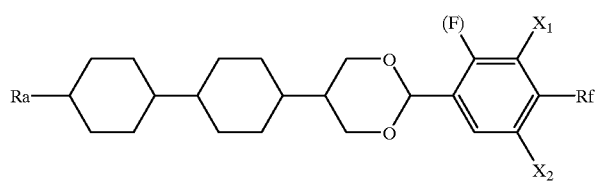

-continued
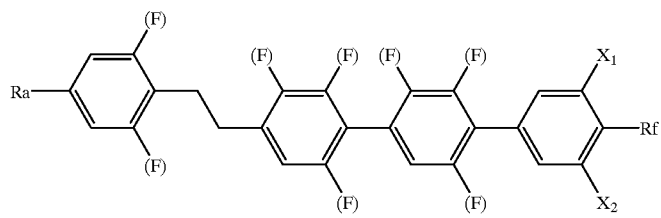
(1-27)
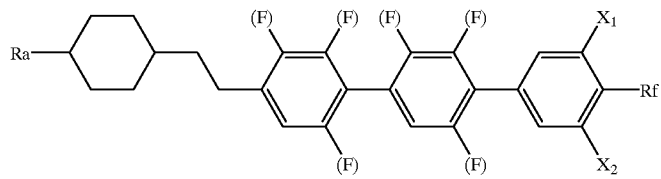
(1-28)
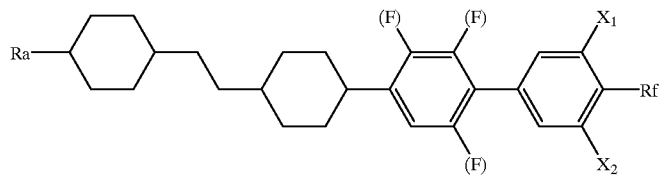
(1-29)
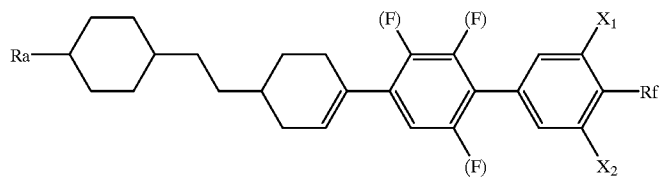
(1-30)
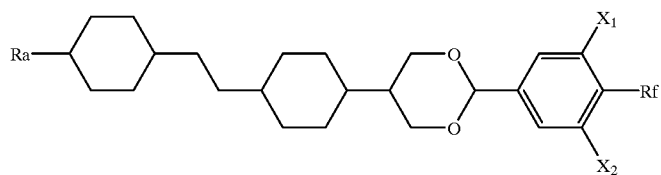
(1-31)
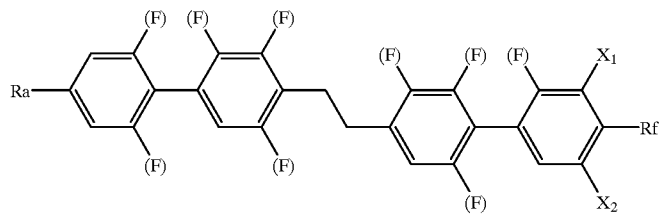
(1-32)
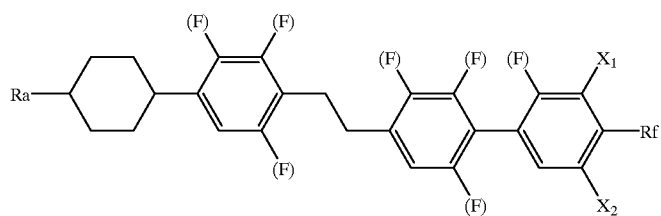
(1-33)

-continued
(1-34)
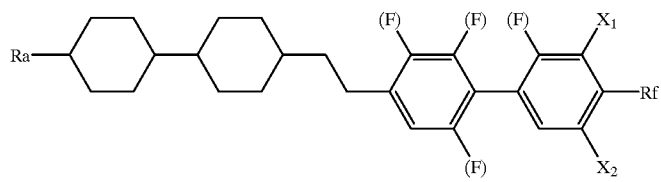
(1-35)
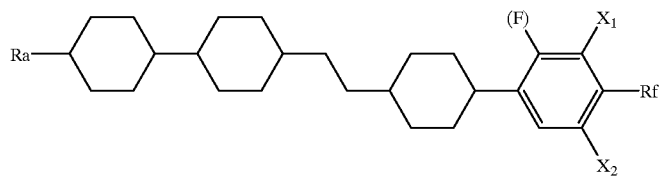
(1-36)
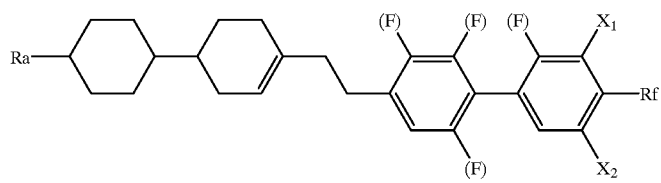
(1-37)
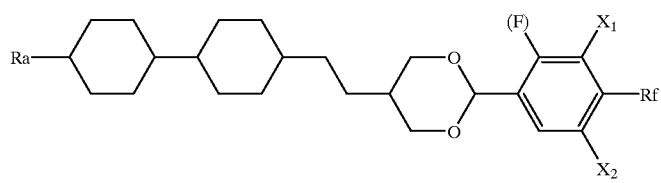
(1-38)
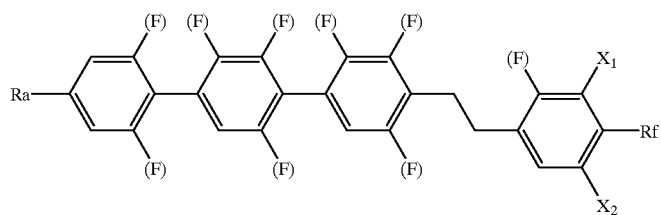
(1-39)
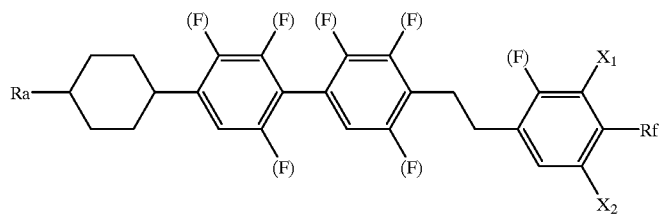
(1-40)
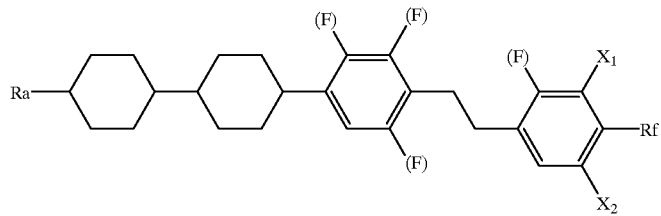

(1-41)
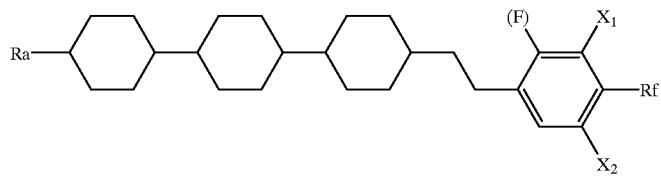
(1-42)
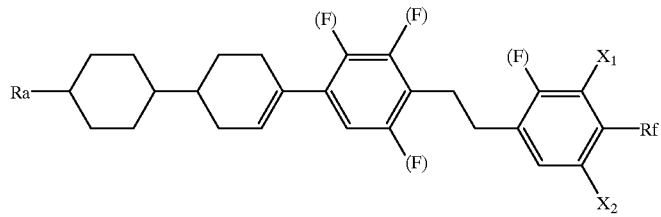
(1-43)
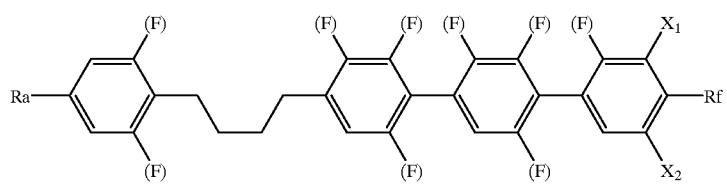
(1-44)
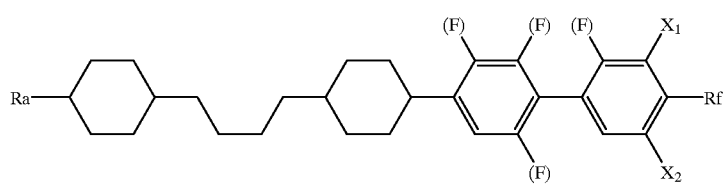
(1-45)
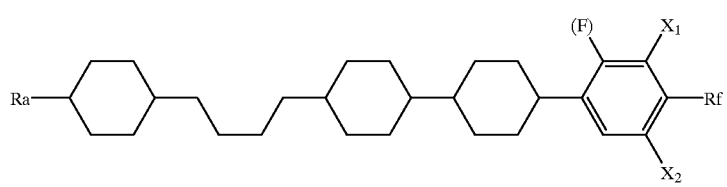
(1-46)
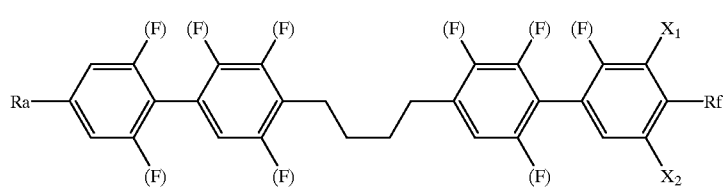
(1-47)
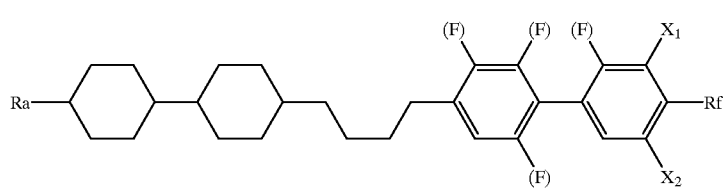
(1-48)
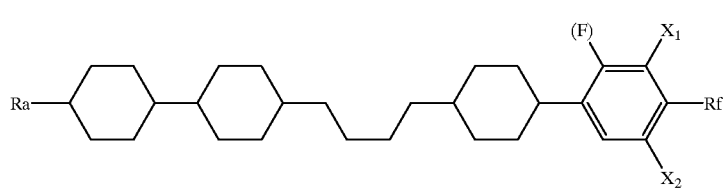

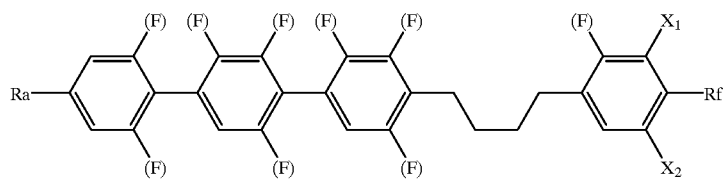
(1-49)
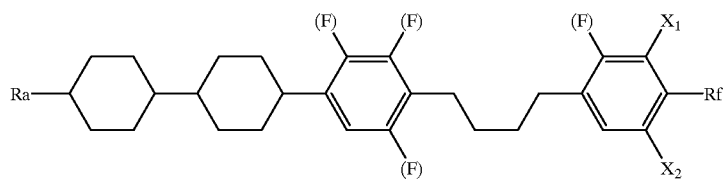
(1-50)
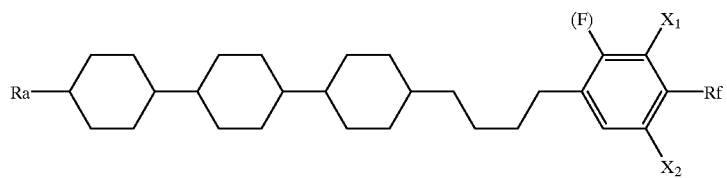
(1-51)
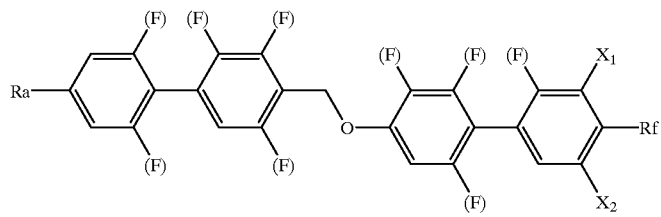
(1-52)
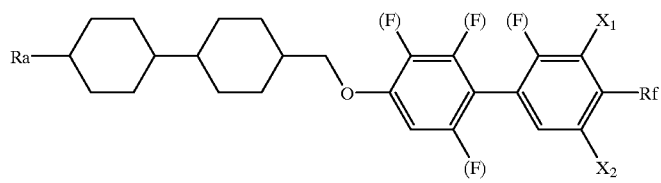
(1-53)
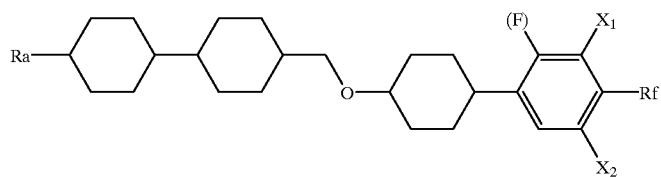
(1-54)
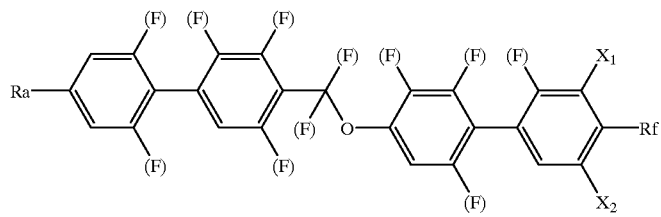
(1-55)

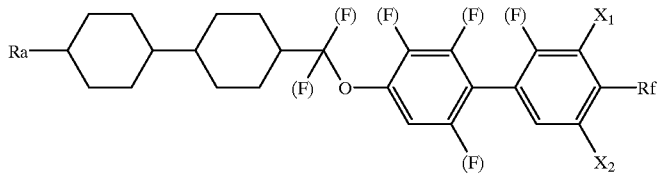

(1-56)

One terminal group Ra of the liquid crystalline compound represented by formula (1) is a straight- or branched chain monovalent organic radical of 1–20 carbons. It may have one or more of —O—, —S—, —CO—, —CH=CH— or an ethynylene bond in the radical, —O— and/or —S— being not adjacent to one another. A hydrogen atom in Ra may be substituted with a halogen atom or a cyano group.

Specific examples of Ra include an alkyl group; an alkenyl group and an alkadienyl group which have —CH=CH— in the groups; an alkynyl group which has an ethynylene bond in the group; an alkoxy group, an alkoxyalkyl group, an alkenyloxy group, an alkoxyalkenyl group, an alkenyloxyalkyl group, an alkynyloxy group, an alkoxyalkynyl group and an alkynyloxyalkyl group which have —O— in the groups; a thioalkyl group and an alkylthioalkyl group which have —S— in the groups; an alkanoyl group and an alkenoyl group which have —CO— in the groups; and a halogen-substituted alkyl group, a halogen-substituted alkenyl group, a halogen-substituted alkoxy group, a halogen-substituted alkenyloxy group, a halogen-substituted alkoxyalkyl group, a halogen-substituted alkoxyalkenyl group and a halogen-substituted alkynyl group, wherein a hydrogen atom in said groups is substituted with a halogen atom; and a cyano-substituted alkyl group and a cyano-substituted alkenyl group wherein a hydrogen atom in said groups is substituted with a cyano group.

An alkyl group includes a straight-chain alkyl group of 1–20 carbons such as methyl, ethyl, propyl, butyl, pentyl, hexyl, heptyl, decyl, pentadecyl and eicosyl, and a branched-chain alkyl group of 1–20 carbons such as isopropyl, sec-butyl, tert-butyl, 2-methylbutyl, isopentyl, isohexyl, 3-ethyloctyl, 3,8-dimethyltetradecyl and 5-ethyl-5-methylnonadecyl. The said branched-chain alkyl group may be optically active.

An organic radical which has —CH=CH— in the radical includes a straight chain alkenyl group such as vinyl, propenyl, butenyl, pentenyl, hexenyl, decenyl and eicosenyl, an alkadienyl group such as butadienyl, pentadienyl, hexadienyl, heptadienyl, octadienyl and eicosadienyl, and a branched chain alkenyl group such as isopropenyl, isopentenyl, isoheptenyl, 3-ethyloctenyl, 3,5-dimethyltetradecenyl and 5-ethyl-5-methylnonadecenyl. An alkynyl group which has an ethynylene bond in the group includes ethynyl, propynyl, butynyl, pentynyl and octynyl.

An organic radical which has —O— in the radical includes an alkoxy group such as methoxy, ethoxy, propoxy, butoxy, pentyloxy and nonyloxy, and an alkoxyalkyl group such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl and octyloxymethyl.

It further includes an alkoxyalkenyl group such as methoxypropenyl, ethoxypropenyl, pentyloxypropenyl, methoxybutenyl, ethoxybutenyl, pentyloxybutenyl, methoxypentenyl, propoxypentenyl, methoxyhexenyl, propoxyhexenyl, methoxyheptenyl and methoxyoctenyl, an alkenyloxy group such as propenyloxy, butenyloxy, pentenyloxy and octenyloxy, an alkenyloxyalkyl group such as propenyloxymethyl, propenyloxyethyl, propenyloxybutyl, butenyloxymethyl, butenyloxyethyl, butenyloxypentyl, pentenyloxymethyl, pentenyloxypropyl, hexenyloxymethyl, hexenyloxyethyl, heptenyloxymethyl and octenyloxymethyl, an alkynyloxy group such as ethynyloxy, propynyloxy, butynyloxy, pentynyloxy and tetradecynyloxy, and an alkoxyalkynyl group such as methoxypropynyl, methoxypentynyl, ethoxybutynyl, propoxypropynyl, hexyloxyheptynyl, methoxymethylbutynyl, methoxypropylethynyl and butoxymethylpropynyl.

An organic radical which has —S— in the radical includes an alkylthioalkyl group such as methylthiomethyl, methylthioethyl, methylthiopropyl, methylthiobutyl, methylthiooctyl, ethylthiomethyl, ethylthioethyl, ethylthioheptyl, propylthiomethyl, propylthioethyl, propylthiopropyl, propylthiopentyl, hexylthiomethyl and heptylthioethyl. An alkanoyl group which has —CO— in the radical includes methylcarbonyl, ethylcarbonyl, propylcarbonyl, methoxycarbonyl, ethoxycarbonyl, propoxycarbonyl, butoxycarbonyl, heptyloxycarbonyl, 2-oxopropyl, 2-oxobutyl, 3-oxobutyl, 2-oxopentyl, 4-oxopentyl, 3-oxohexyl, 5-oxohexyl, 2-oxoheptyl, 3-oxoheptyl, 6-oxoheptyl, 2-oxooctyl, 4-oxooctyl, 7-oxooctyl, 3-oxononyl, 6-oxononyl, 8-oxononyl, 2-oxodecyl, 5-oxodecyl and 9-oxodecyl.

An organic radical where a hydrogen atom in the above substituents is substituted with a halogen atom and/or a cyano group includes a halogen-substituted alkyl group such as fluoromethyl, difluoromethyl, trifluoromethyl, 2-fluoroethyl, 1,2-difluoroethyl, 1,1,2,2-tetrafluoroethyl, 2-bromo-1,2-difluoroethyl, 3-fluoropropyl, 1,2,3,3-tetrafluoropropyl, 1,1,2,3,3,3-hexafluoropropyl, 3-fluorobutyl, 4-fluorobutyl, 1,1,2,4-tetrafluorobutyl, 3-fluoropentyl, 5-fluoropentyl, 2,3,3,4,5-pentafluoropentyl, 6-fluorohexyl, 2,3,4,6-tetrafluorohexyl, 7-fluoroheptyl and 8,8-difluorooctyl, a halogen-substituted alkoxy group such as difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 1,1,2,3,3,3-hexafluoropropoxy and perfluoropropoxy, a halogen-substituted alkenyl group such as 3-fluoropropenyl, 4-fluoro-1-butenyl, 4-fluoro-2-butenyl, 5-fluoro-1-pentenyl, 5-fluoro-2-pentenyl, 5-fluoro-3-pentenyl, 6-fluoro-1-hexenyl, 6-fluoro-3-hexenyl, 7-fluoro-5-heptenyl, 2-chlorovinyl, 2-fluorovinyl, 2-cyanovinyl, 2,2-difluorovinyl, 1,2-difluorovinyl, 2-chloro-2-fluorovinyl, 2-bromo-2-fluorovinyl, 2-fluoro-2-cyanovinyl, 3,3-difluoro-2-propenyl, 3-chloro-3-fluoro-1-propenyl, 2,3-difluoro-1-propenyl, 1,3-difluoro-2-propenyl, 1,3,3-trifluoro-2-propenyl, 1,2,4,4-tetrafluoro-3-butenyl, 5,5-difluoro-4-pentenyl, 3,3-difluoro-5-hexenyl and 8,8-difluoro-7-octenyl.

The liquid crystalline compounds represented by formula (1) according to the present invention can be prepared by a known, conventional method for organic synthesis. For example, they can be easily prepared in the manner as illustrated in the following Schemes 1–3.

In the Schemes, Ra, $A_1$, $A_2$, $A_3$, $Z_1$, $Z_2$, $X_1$, $X_2$ and Rf have the same meanings as defined above, n and o represent 0 or 1, p represents an integer of 1 or 2, and X and X' represent a halogen atom. (F) on the 1,4-phenylene ring stands for the case where said ring may be substituted with F.

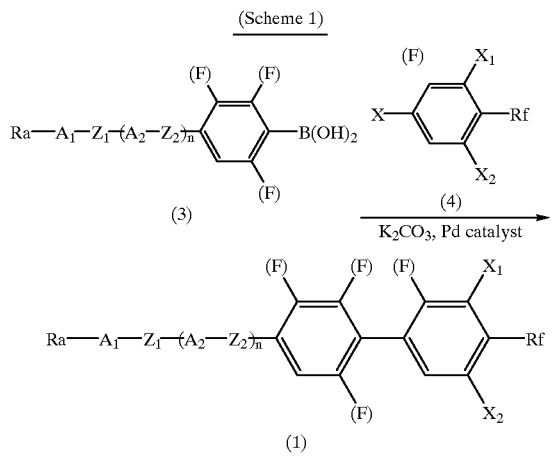

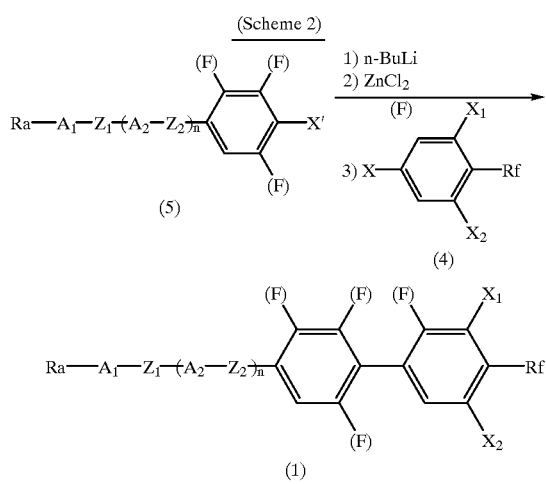

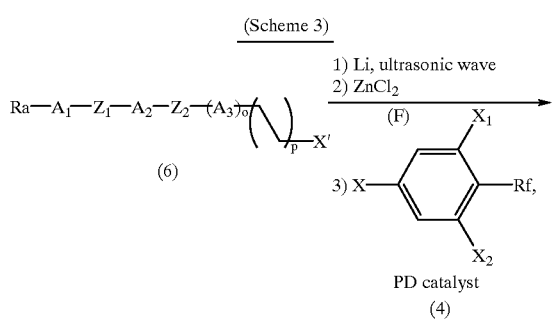

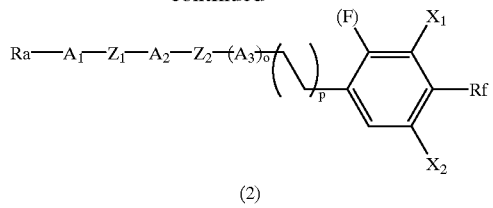

As shown in Scheme 1, compound (1) as an example of the present compounds can be prepared by reacting a boronic acid derivative (3) with a halide (4) in a mixed solvent of toluene or xylene, etc., alcohols such as ethanol and water, in the presence of a base such as $K_2CO_3$ or $Na_2CO_3$ and a catalyst such as Pd-C, $Pd(PPh_3)_4$ or $PdCl_2(PPh_3)_2$. Alternatively, as shown in Scheme 2, compound (1) can be prepared by reacting a halide (5) with a lithium reagent such as n-BuLi and a zinc reagent such as $ZnCl_2$ or $ZnBr_2$, followed by reacting with a halide (4).

As shown in Scheme 3, compound (2) as an example of the present compounds can be prepared by converting a halide (6) into its lithium salt, followed by reacting with a zinc reagent and a halide (4).

The compounds which contain —O— in the Ra radical or in the bridges $Z_1$–$Z_3$ between the rings can be prepared by reacting the corresponding halides and alcohols in a solvent such as dimethylsulfoxide, dimethylformamide, 1,2-dimethoxyethane, tetrahydrofuran, hexamethylphosphoric acid triamide or toluene, in the presence of a base, for example, sodium amide (Wright, J. B. et al., Journal of the American Chemical Society, 70, 3098 (1948)), potassium carbonate (Olson, W. T. et al., Journal of the American Chemical Society, 69, 2451 (1947)), triethylamine (Merker, R. L. et al., The Journal of Organic Chemistry, 26, 5180 (1961)), sodium hydroxide (Wilkins, C., Synthesis, 1973, 156), potassium hydroxide (Rebek, J. et al., The Journal of Organic Chemistry, 44, 1485 (1979)), barium hydroxide (Kawabe et al., The Journal of Organic Chemistry, 37, 4210 (1972)) or sodium hydride (Stark, C. J., Tetrahedron Letters, 22, 2089 (1981), Takai, K. et al., Tetrahedron Letters, 21, 1657 (1980)). Alternatively, they can be prepared from derivatives of trifluoromethanesulfonic acid ester or the like.

The compounds which contain a —C=C— bond in the Ra radical can easily be prepared by introducing the bond into molecules, for example, by Wittig reaction (Organic Reactions, Vol. 14, 3), Wittig-Schlosser reaction (Schlosser, M. et al., Angewandt Chemie International Edition in English, 5, 126 (1966)) or Wittig-Horner reaction (Cadogan, J. I. G., Organophosphorus Reagents in Organic Synthesis, Academic (1979)).

The compounds which contain an ethynylene bond in the Ra radical can be prepared, for example, by the method of W. Tao et al. (The Journal of Organic Chemistry, 55, 63 (1990)), i.e., by reacting the acetylene derivatives with halides in a solvent of alkylamine such as diethylamine or triethylamine in the presence of copper iodide and a Pd catalyst such as $Pd(PPh_3)_4$ or $PdCl_2(PPh_3)_2$. This reaction is preferably carried out at temperatures in the range between room temperature and the boiling point of the solvent under an inert gas atmosphere. They can also be prepared by Castro reaction (Raush, M. D. et al., The Journal of Organic Chemistry, 34, 468 (1969)).

The compounds which contain —COO— (carbonyloxy) in the Ra radical can be prepared, for example, by the method of E. J. Corey et al. (The Journal of Organic Chemistry, 38, 3223 (1973)), i.e., by converting the corresponding carboxylic acid into its acid halide with a halogenating agent such as thionyl chloride in a solvent such as toluene or benzene or without a solvent, followed by reacting with alcohols. This reaction is preferably carried out at temperatures in the range between room temperature and the boiling point of the solvent under an inert gas atmosphere, and more preferably in the presence of a base such as pyridine, triethylamine (Iselin, B. et al., Helvetica Chimica Acta, 40, 373 (1957)), dimethylaniline (Raha, C., Organic Synthesis, IV, 263 (1963)) or tetramethylurea (Newman, M. S. et al., Tetrahedron Letters, 3267 (1967)) to promote the reaction. Alternatively, they can be prepared by reacting the corresponding carboxylic acids with alcohols in a solvent such as dichloromethane or chloroform in the presence of a dehydrating agent such as dicyclohexylcarbodiimide and 4-dimethylaminopyridine (Neises, B. et al., Organic Synthesis, 63, 183 (1985)).

All the above reactions are known, but if necessary, other known reactions can be employed.

The liquid crystalline compounds represented by formula (1) according to the present invention have exceedingly high voltage holding ratio, low threshold voltage and their exceedingly small temperature dependency. They also have high $\Delta n$, and are easily mixed with various liquid crystal materials, and have excellent compatibility, especially at low temperatures. These liquid crystalline compounds further have sufficient physical and chemical stabilities under conditions where display devices are usually used. Moreover, the compounds having the desired physical values can be obtained by suitably selecting a 6-membered ring, a substituent thereof and/or a bridge between the rings among the molecular constitutional elements.

The compounds having three rings in the molecule exhibit liquid crystal phases at comparatively low temperatures, and the compounds having four rings in the molecule exhibit high isotropic phase transition temperature. The compounds having a cyclohexene ring or a dioxane ring exhibit comparatively low $\Delta n$, and the compounds having a dioxane ring exhibit comparatively high $\Delta \epsilon$.

The compounds having a double bond in the Ra radical have high elastic constant ratio (bend elastic constant/splay elastic constant), so that they can be used as a component of the compositions for STN to prepare the compositions having steep change of transmittance which can provide display devices of high contrast. The compounds where the Ra radical is optically active are particularly important as a chiral dopant. $\Delta \epsilon$ can be higher by substituting a hydrogen atom in the ring structure with a fluorine atom, while the compatibility can be improved.

The compounds having —$CF_2O$— or —$OCF_2$— in $Z_1$, $Z_2$ or $Z_3$ exhibit comparatively high $\Delta \epsilon$ and low viscosity.

Accordingly, suitable selection of a ring, a substituent and/or a bond can provide liquid crystalline compounds having desired physical properties.

Some of the compounds of the present invention exhibit such a high elastic constant that they are suitable for the compounds for low Vth.

Specific examples of the preferable compounds represented by formula (1) according to the present invention are given below, where the above abbreviations are used for rings (provided that the parenthesized abbreviation represents a position for substitution and a substituted atom or atoms based on a fluoroalkoxy group at the 4-position).

A) Examples of tricyclic compounds

| | |
|---|---|
| Compound No. 1 | $C_3H_7$—Be—$C_2H_4$—Be(3F)—Be(3F)—$OCF_2CFHCF_3$ |
| Compound No. 2 | $C_3H_7$—Be—Be—Be—$OCF_2CF_2H$ |
| Compound No. 3 | $C_5H_{11}$—Be—Be—Be(3F)—$OCF_2CFHCF_3$ |
| Compound No. 4 | $CH_3$—Be—Be(3F)—Be—$OCF_2CF_2H$ |
| Compound No. 5 | $C_3H_7$—Be—Be(2,3F)—Be—$OCF_2CF_2H$ |
| Compound No. 6 | $C_2H_5$—Be—Be—Be(3,5F)—$OCF_2CF_2H$ |
| Compound No. 7 | $C_4H_9$—Be—Be(3F)—Be(3F)—$OCF_2CFHCF_3$ |
| Compound No. 8 | $CH_3O$—Be—Be(3F)—Be(3,5F)—$OCF_2CF_2H$ |
| Compound No. 9 | $CH_3CH=CHC_2H_4$—Be(3F)—Be—Be(3,5F)—$OCF_2CFHCF_3$ |
| Compound No. 10 | $C_3H_7O$—Be—Be(3,5F)—Be(3F)—$OCF_2CFHCF_3$ |
| Compound No. 11 | $C_5H_{11}OCH_2$—Be(3F)—Be(3F)—Be(3F)—$OCF_2CF_2H$ |
| Compound No. 12 | $C_2H_5OC_5H_{10}$—Be(3F)—Be(3F)—Be(3,5F)—$OCF_2CFHCF_3$ |
| Compound No. 13 | $C_5H_{11}$—Be—Be(2,3F)—Be(2,3F)—$OCF_2CF_2H$ |
| Compound No. 14 | $CFH_2C_2H_4$—Be(3F)—Be(3,5F)—Be(3F)—$OCF_2CFHCF_3$ |
| Compound No. 15 | $C_2H_5$—Ch—Be—Be—$OCF_2CF_2H$ |
| Compound No. 16 | $C_3H_7$—Ch—Be—Be(3,5F)—$OCF_2CFHCF_3$ |
| Compound No. 17 | $C_4H_9$—Ch—Be(3,5F)—Be(3F)—$OCF_2CFHCF_3$ |
| Compound No. 18 | $C_5H_{11}O$—Ch—Be(3,5F)—Be(3,5F)—$OCF_2CF_2H$ |
| Compound No. 19 | $C_3H_7$—Do—Be(3F)—Be(3F)—$OCF_2CF_2H$ |
| Compound No. 20 | $C_5H_{11}$—Do—Be(3F)—Be(3,5F)—$OCF_2CFHCF_3$ |
| Compound No. 21 | $C_{15}H_{31}$—Do—Be—Be(3,5F)—$OCF_2CFHCF_3$ |
| Compound No. 22 | $C_4H_9$—Ch—Ch—Be(3,5F)—$OCF_2CF_2H$ |
| Compound No. 23 | $C_{10}H_{21}OCH_2$—Ch—Ch—Be(3F)—$OCF_2CFHCF_3$ |
| Compound No. 24 | $C_2H_5$—Ch—Do—Be(3,5F)—$OCF_2CF_2H$ |
| Compound No. 25 | $C_4H_9O$—Ch—Do—Be(3,5F)—$OCF_2CFHCF_3$ |
| Compound No. 26 | $C_2H_5$—Be—$C_2H_4$—Be—Be(3F)—$OCF_2CF_2H$ |
| Compound No. 27 | $C_3H_7$—Be—$C_2H_4$—Be—Be(3F)—$OCF_2CFHCF_3$ |
| Compound No. 28 | $C_4H_9$—Be—$C_2H_4$—Be—Be(3Cl)—$OCF_2CFHCF_3$ |
| Compound No. 29 | $C_5H_{11}$—Be—$C_2H_4$—Be(3F)—Be—$OCF_2CF_2H$ |
| Compound No. 30 | $C_7H_{15}$—Be—$C_2H_4$—Be—Be(3F)—$OCF_2CFHCF_3$ |
| Compound No. 31 | $C_4H_9$—Be(3F)—$C_2H_4$—Be—Be—$OCF_2CF_2H$ |
| Compound No. 32 | $CH_3$—Be(3F)—$C_2H_4$—Be—Be—$OCF_2CFHCF_3$ |
| Compound No. 33 | $C_3H_7$—Be—$C_2H_4$—Be—Be(3,5F)—$OCF_2CF_2H$ |
| Compound No. 34 | $H_2C=CHC_2H_4$—Be—$C_2H_4$—Be—Be(3,5F)—$OCF_2CF_2H$ |
| Compound No. 35 | $C_5H_{11}$—Be—$C_2H_4$—Be—Be(3,5F)—$OCF_2CFHCF_3$ |
| Compound No. 36 | $C_2H_5$—Be—$C_2H_4$—Be—Be(3F, 5Cl)—$OCF_2CF_2H$ |

-continued

| | |
|---|---|
| Compound No. 37 | $C_2H_5$—Be—$C_2H_4$—Be(3F)—Be(3F)—$OCF_2CF_2H$ |
| Compound No. 38 | $C_3H_7$—Be—$C_2H_4$—Be(3F)—Be(3F)—$OCF_2CFHCF_3$ |
| Compound No. 39 | $C_3H_7$—Be—$C_2H_4$—Be(3,5F)—Be—$OCF_2CF_2H$ |
| Compound No. 40 | $C_4H_9OCH_2$—Be—$C_2H_4$—Be(3,5F)—Be—$OCF_2CF_2H$ |
| Compound No. 41 | $C_2H_5O$—Be(3F)—$C_2H_4$—Be—Be(3F)—$OCF_2CF_2H$ |
| Compound No. 42 | $CH_3$—Be(3,5F)—$C_2H_4$—Be—Be—$OCF_2CFHCF_3$ |
| Compound No. 43 | $C_2H_5$—Be—$C_2H_4$—Be(3F)—Be(3,5F)—$OCF_2CF_2H$ |
| Compound No. 44 | $C_5H_{11}$—Be—$C_2H_4$—Be(3F)—Be(3F,5Cl)—$OCF_2CF_2H$ |
| Compound No. 45 | $C_2H_5O$—Be—$C_2H_4$—Be(3F)—Be(3,5F)—$OCF_2CFHCF_3$ |
| Compound No. 46 | $F_2C=CHC_2H_4$—Be(3F)—$C_2H_4$—Be(3F)—Be(3F)—$OCF_2CF_2H$ |
| Compound No. 47 | $C_2H_5CFHC_2H_4$—Be(3F)—$C_2H_4$—Be(3F)—Be(3F)—$OCF_2CFHCF_3$ |
| Compound No. 48 | $C_5H_{11}$—Be—$C_2H_4$—Be(3,5F)—Be(3,5F)—$OCF_2CF_2H$ |
| Compound No. 49 | $C_3H_7$—Be—$C_2H_4$—Be(3,5F)—Be(3,5F)—$OCF_2CFHCF_3$ |
| Compound No. 50 | $CH_3CH=CH$—Be—$C_2H_4$—Be(3,5F)—Be(3,5F)—$OCF_2CF_2H$ |
| Compound No. 51 | $C_5H_{11}$—Be—$C_2H_4$—Be(2,3F)—Be(2,3F)—$OCF_2CF_2H$ |
| Compound No. 52 | $CH_3$—Be(3F)—$C_2H_4$—Be(3F)—Be(3,5F)—$OCF_2CF_2H$ |
| Compound No. 53 | $C_5H_{11}$—Be(3F)—$C_2H_4$—Be(3F)—Be(3,5F)—$OCF_2CFHCF_3$ |
| Compound No. 54 | $C_4H_9$—Be(3F)—$C_2H_4$—Be(3F)—Be(3F,5Cl)—$OCF_2CFHCF_3$ |
| Compound No. 55 | $F_2C=CH$—Be(3F)—$C_2H_4$—Be(3F)—Be(3,5F)—$OCF_2CF_2H$ |
| Compound No. 56 | $C_6H_{13}$—Be(3F)—$C_2H_4$—Be(3,5F)—Be(3F)—$OCF_2CFHCF_3$ |
| Compound No. 57 | $C_5H_{11}O$—Be(3,5F)—$C_2H_4$—Be(3,5F)—Be—$OCF_2CF_2H$ |
| Compound No. 58 | $C_{12}H_{25}O$—Be(3,5F)—$C_2H_4$—Be(3F)—Be(3F)—$OCF_2CFHCF_3$ |
| Compound No. 59 | $C_4H_9$—Be(3F)—$C_2H_4$—Be(3,5F)—Be(3,5F)—$OCF_2CF_2H$ |
| Compound No. 60 | $CH_3OC_3H_6$—Be(3,5F)—$C_2H_4$—Be(3F)—Be(3,5F)—$OCF_2CFHCF_3$ |
| Compound No. 61 | $CH_3O$—Be(3,5F)—$C_2H_4$—Be(3,5F)—Be(3F)—$OCF_2CFHCF_3$ |
| Compound No. 62 | $C_2H_5$—Ch—$C_2H_4$—Be—Be(3,5F)—$OCF_2CF_2H$ |
| Compound No. 63 | $C_5H_{11}$—Ch—$C_2H_4$—Be(3,5F)—Be(3F)—$OCF_2CFHCF_3$ |
| Compound No. 64 | $H_2C=CHCH_2O$—Ch—$C_2H_4$—Be(3F)—Be(3,5F)—$OCF_2CF_2H$ |
| Compound No. 65 | $C_3H_7$—Ch—$C_2H_4$—Ch—Be(3F)—$OCF_2CF_2H$ |
| Compound No. 66 | $C_4H_9$—Ch—$C_2H_4$—Ch—Be(3,5F)—$OCF_2CFHCF_3$ |
| Compound No. 67 | $F(CN)C=CH$—Ch—$C_2H_4$—Ch—Be(3,5F)—$OCF_2CF_2H$ |
| Compound No. 68 | $CH_3$—Do—$C_2H_4$—Be—Be(3F,4Cl)—$OCF_2CF_2H$ |
| Compound No. 69 | $C_8H_{17}O$—Do—$C_2H_4$—Be(3F)—Be(3F)—$OCF_2CFHCF_3$ |
| Compound No. 70 | $C_2H_5OCH_2$—Do—$C_2H_4$—Be(3F)—Be(3,5F)—$OCF_2CFHCF_3$ |
| Compound No. 71 | $C_3H_7$—Be—Be—$C_2H_4$—Be(3F)—$OCF_2CF_2H$ |
| Compound No. 72 | $C_2H_5$—Be—Be—$C_2H_4$—Be(3F)—$OCF_2CFHCF_3$ |
| Compound No. 73 | $H_2C=CHC_2H_4$—Be—Be(3F)—$C_2H_4$—Be—$OCF_2CF_2H$ |
| Compound No. 74 | $C_5H_{11}$—Be—Be(3F)—$C_2H_4$—Be—$OCF_2CFHCF_3$ |
| Compound No. 75 | $C_{16}H_{33}$—Be(3F)—Be—$C_2H_4$—Be—$OCF_2CF_2H$ |
| Compound No. 76 | $C_4H_9$—Be(3F)—Be—$C_2H_4$—Be—$OCF_2CFHCF_3$ |
| Compound No. 77 | $CH_3$—Be—Be—$C_2H_4$—Be(3,5F)—$OCF_2CF_2H$ |
| Compound No. 78 | $C_3H_7O$—Be—Be—$C_2H_4$—Be(3,5F)—$OCF_2CFHCF_3$ |
| Compound No. 79 | $C_7H_{15}$—Be—Be—$C_2H_4$—Be(3F,5Cl)—$OCF_2CF_2H$ |
| Compound No. 80 | $F_2C=CHC_3H_6$—Be—Be(3F)—$C_2H_4$—Be(3F)—$OCF_2CF_2H$ |
| Compound No. 81 | $C_6H_{13}$—Be—Be(3F)—$C_2H_4$—Be(3F)—$OCF_2CFHCF_3$ |
| Compound No. 82 | $C_3H_7$—Be—Be(3,5F)—$C_2H_4$—Be—$OCF_2CF_2H$ |
| Compound No. 83 | $C_5H_{11}$—Be—Be(2,3F)—$C_2H_4$—Be—$OCF_2CF_2H$ |
| Compound No. 84 | $C_2H_5O$—Be—Be(3,5F)—$C_2H_4$—Be—$OCF_2CFHCF_3$ |
| Compound No. 85 | $C_3H_7$—Be(3F)—Be—$C_2H_4$—Be(3F)—$OCF_2CF_2H$ |
| Compound No. 86 | $C_4H_9$—Be(3,5F)—Be—$C_2H_4$—Be—$OCF_2CFHCF_3$ |
| Compound No. 87 | $C_2H_5$—Be—Be(3F)—$C_2H_4$—Be(3,5F)—$OCF_2CF_2H$ |
| Compound No. 88 | $C_5H_{11}$—Be—Be(3F)—$C_2H_4$—Be(3F,5Cl)—$OCF_2CF_2H$ |
| Compound No. 89 | $C_5H_{11}$—Be—Be(3F)—$C_2H_4$—Be(3,5F)—$OCF_2CFHCF_3$ |
| Compound No. 90 | $CFH_2C_4H_8$—Be(3F)—Be(3F)—$C_2H_4$—Be(3F)—$OCF_2CF_2H$ |
| Compound No. 91 | $C_9H_{19}$—Be(3F)—Be(3F)—$C_2H_4$—Be(3F)—$OCF_2CFHCF_3$ |
| Compound No. 92 | $C_4H_9$—Be—Be(3,5F)—$C_2H_4$—Be(3,5F)—$OCF_2CF_2H$ |
| Compound No. 93 | $C_3H_7$—Be—Be(3,5F)—$C_2H_4$—Be(3,5F)—$OCF_2CFHCF_3$ |
| Compound No. 94 | $CH_3CH=CHC_2H_4$—Be—Be(3,5F)—$C_2H_4$—Be(3,5F)—$OCF_2CFHCF_3$ |
| Compound No. 95 | $CH_3O$—Be(2,3F)—Be(2,3F)—$C_2H_4$—Be(2,3F)—$OCF_2CFHCF_3$ |
| Compound No. 96 | $C_7H_{15}$—Be(3F)—Be(3F)—$C_2H_4$—Be(3,5F)—$OCF_2CF_2H$ |
| Compound No. 97 | $C_3H_7$—Be(3F)—Be(3F)—$C_2H_4$—Be(3,5F)—$OCF_2CFHCF_3$ |
| Compound No. 98 | $C_3H_7$—Be(3F)—Be(3F)—$C_2H_4$—Be(3F,5Cl)—$OCF_2CF_2H$ |
| Compound No. 99 | $C_8H_{17}$—Be(3F)—Be(3,5F)—$C_2H_4$—Be(3F)—$OCF_2CF_2H$ |
| Compound No. 100 | $CH_3OCH_2CH=CH$—Be(3F)—Be(3,5F)—$C_2H_4$—Be(3F)—$OCF_2CFHCF_3$ |
| Compound No. 101 | $C_2H_5$—Be(3,5F)—Be(3F)—$C_2H_4$—Be—$OCF_2CF_2H$ |
| Compound No. 102 | $C_5H_{11}$—Be(3,5F)—Be(3F)—$C_2H_4$—Be—$OCF_2CFHCF_3$ |
| Compound No. 103 | $C_4H_9$—Be(3,5F)—Be(3F)—$C_2H_4$—Be(3F)—$OCF_2CFHCF_3$ |
| Compound No. 104 | $C_6H_{13}O$—Be(3,5F)—Be(3F)—$C_2H_4$—Be(3F)—$OCF_2CFHCF_3$ |
| Compound No. 105 | $C_3H_7$—Be(3F)—Be(3,5F)—$C_2H_4$—Be(3,5F)—$OCF_2CF_2H$ |
| Compound No. 106 | $C_4H_9$—Be(3F)—Be(3,5F)—$C_2H_4$—Be(3,5F)—$OCF_2CFHCF_3$ |
| Compound No. 107 | $CH_3OC_3H_6$—Be(3,5F)—Be(3F)—$C_2H_4$—Be(3,5F)—$OCF_2CF_2H$ |
| Compound No. 108 | $C_5H_{11}$—Be(3,5F)—Be(3,5F)—$C_2H_4$—Be(3F)—$OCF_2CF_2H$ |
| Compound No. 109 | $C_3H_7$—Ch—Be—Be(3F)—$C_2H_4$—Be(3F)—$OCF_2CF_2H$ |
| Compound No. 110 | $C_5H_{11}$—Ch—Be—Be(3,5F)—$C_2H_4$—Be(3F)—$OCF_2CFHCF_3$ |
| Compound No. 111 | $CH_3O$—Do—Be—Be—$C_2H_4$—Be(3,5F)—$OCF_2CF_2H$ |
| Compound No. 112 | $C_2H_5$—Do—Be—Be(3,5F)—$C_2H_4$—Be(3,5F)—$OCF_2CFHCF_3$ |
| Compound No. 113 | $C_3H_7$—Be—$C_4H_8$—Be—Be(3,5F)—$OCF_2CF_2H$ |
| Compound No. 114 | $C_4H_9$—Be—$C_4H_8$—Be(3F)—Be(3F)—$OCF_2CFHCF_3$ |
| Compound No. 115 | $C_5H_{11}$—Be(3F)—$C_4H_8$—Be(3F)—Be(3F)—$OCF_2CF_2H$ |

-continued

Compound No. 116  $C_3H_7O$—Be—$C_4H_8$—Be(3F)—Be(3,5F)—$OCF_2CFHCF_3$
Compound No. 117  $C_4H_9OCH_2$—Be—$C_4H_8$—Be(2,3F)—$OCF_2CF_2H$
Compound No. 118  $C_3H_7$—Be—$C_4H_8$—Be(3F)—$OCF_2CF_2H$
Compound No. 119  $C_7H_{15}$—Be—Be—$C_4H_8$—Be(3,5F)—$OCF_2CFHCF_3$
Compound No. 120  $C_6H_{13}$—Be(3F)—Be(3F)—$C_4H_8$—Be(3F)—$OCF_2CF_2H$
Compound No. 121  $CFH_2CH_2CH=CH$—Be—Be(3,5F)—$C_4H_8$—Be(3,5F)—$OCF_2CF_2H$
Compound No. 122  $CH_3$—Be—$CH_2O$—Be—Be(3,5F)—$OCF_2CF_2H$
Compound No. 123  $C_3H_7$—Be—$CH_2O$—Be(3F)—Be(3F)—$OCF_2CFHCF_3$
Compound No. 124  $C_5H_{11}$—Be—$CH_2O$—Be(3,5F)—Be(3F)—$OCF_2CF_2H$
Compound No. 125  $C_7H_{15}$—Be—$CH_2O$—Be(3,5F)—Be(3,5F)—$OCF_2CF_2H$
Compound No. 126  $C_3H_7OCH_2$—Be(3F)—$CH_2O$—Be(3,5F)—Be(3,5F)—$OCF_2CFHCF_3$
Compound No. 127  $CH_3O$—Ch—$CH_2O$—Be—Be(2,3F)—$OCF_2CF_2H$
Compound No. 128  $CH_3OCH_2$—Ch—$CH_2O$—Be(3F)—Be(3,5F)—$OCF_2CFHCF_3$
Compound No. 129  $C_2H_5$—Be—Be(3F)—$CH_2O$—Be(3F,5Cl)—$OCF_2CF_2H$
Compound No. 130  $C_4H_9$—Be(3F)—Be(3,5F)—$CH_2O$—Be(3,5F)—$OCF_2CFHCF_3$
Compound No. 131  $C_3H_7$—Be—$CF_2O$—Be(3F)—Be(3F)—$OCF_2CFHCF_3$
Compound No. 132  $C_3H_7$—Be—$CF_2O$—Be(3F)—Be(3,5F)—$OCF_2CF_2H$
Compound No. 133  $C_5H_{11}$—Be—$CF_2O$—Be(3,5F)—Be(3F)—$OCF_2CF_2H$
Compound No. 134  $C_{18}H_{37}$—Ch—$CF_2O$—Be—Be(3,5F)—$OCF_2CF_2H$
Compound No. 135  $F_2C=CHC_2H_4$—Ch—$CF_2O$—Be(3,5F)—Be(3F)—$OCF_2CFHCF_3$
Compound No. 136  $C_5H_{11}$—Be—Be—$CF_2O$—Be(3,5F)—$OCF_2CF_2H$
Compound No. 137  $C_3H_7$—Be(3F)—Be(3,5F)—$CF_2O$—Be(3F)—$OCF_2CFHCF_3$ B) Examples of tetracyclic compounds Compound No. 138  $C_3H_7$—Hx—$C_2H_4$—Hx—Be(3F)—Be(3F)—$OCF_2CF_2H$
Compound No. 139  $C_2H_5$—Be—Be—Be(3F)—Be(3F)—$OCF_2CFHCF_3$
Compound No. 140  $C_2H_5$—Be—Be—Be—Be(2,3F)—$OCF_2CF_2H$
Compound No. 141  $C_3H_7$—Be—Be—Be(2,3F)—Be—$OCF_2CFHCF_3$
Compound No. 142  $C_2H_5$—Be—Be(3F)—Be(3F)—Be(3,5F)—$OCF_2CFHCF_3$
Compound No. 143  $C_3H_7$—Be—Be—Be(3,5F)—Be(3,5F)—$OCF_2CF_2H$
Compound No. 144  $C_4H_9O$—Be—Be(3F)—Be(3F)—Be(3F)—$OCF_2CF_2H$
Compound No. 145  $C_3H_7$—Be(3F)—Be(3F)—Be(3F)—Be(3F)—$OCF_2CFHCF_3$
Compound No. 146  $CH_3OC_3H_{10}$—Be(3F)—Be(3F)—Be(3F)—Be(3,5F)—$OCF_2CFHCF_3$
Compound No. 147  $C_5H_{11}$—Be(3F)—Be(3,5F)—Be(3F)—Be(3F)—$OCF_2CF_2H$
Compound No. 148  $C_3H_7$—Hx—Be—Be—Be(2,3Cl)—$OCF_2CF_2H$
Compound No. 149  $C_3H_7$—Hx—Be—Be(2,3F)—Be—$OCF_2CF_2H$
Compound No. 150  $C_4H_9$—Hx—Be—Be(3,5F)—Be(3F)—$OCF_2CFHCF_3$
Compound No. 151  $C_5H_{11}$—Hx—Be—Be(3,5F)—Be(3F,5Cl)—$OCF_2CF_2H$
Compound No. 152  $C_3H_7OCH_2$—Hx—Be(3F)—Be(3,5F)—Be(3,5F)—$OCF_2CFHCF_3$
Compound No. 153  $C_3H_7$—Hx—Hx—Be(3F)—Be(3F)—$OCF_2CF_2H$
Compound No. 154  $C_6H_{13}$—Hx—Hx—Be—Be(2,3F)—$OCF_2CF_2H$
Compound No. 155  $C_3H_7$—Hx—Hx—Be(2,3Cl)—Be—$OCF_2CFHCF_3$
Compound No. 156  $C_4H_9$—Hx—Hx—Be—Be(3,5F)—$OCF_2CFHCF_3$
Compound No. 157  $C_5H_{11}$—Hx—Hx—Be(3F)—Be(3F)—$OCF_2CF_2H$
Compound No. 158  $C_2H_5$—Hx—Hx—Be(3,5F)—Be(3F)—$OCF_2CFHCF_3$
Compound No. 159  $C_3H_7$—Hx—Hx—Be(2,3F)—Be(2,3F)—$OCF_2CF_2H$
Compound No. 160  $C_2H_5OCH_2$—Hx—Hx—Be(3F)—Be(3F)—$OCF_2CF_2H$
Compound No. 161  $CFH_2C_2H_4$—Hx—Hx—Be(3F)—Be(3,5F)—$OCF_2CFHCF_3$
Compound No. 162  $CF_2HC_2H_4$—Hx—Hx—Be(3F)—Be(3F)—$OCF_2CF_2H$
Compound No. 163  $CH_3CH=CH$—Hx—Hx—Be(3F)—Be(3F)—$OCF_2CF_2H$
Compound No. 164  $F_2C=CH$—Hx—Hx—Be(3,5F)—Be(3F)—$OCF_2CFHCF_3$
Compound No. 165  $C_5H_{11}$—Hx—Hx—Hx—Be—$OCF_2CF_2H$
Compound No. 166  $C_6H_{13}$—Hx—Hx—Hx—Be(3F)—$OCF_2CF_2H$
Compound No. 167  $C_3H_7$—Hx—Hx—Hx—Be—$OCF_2CFHC_3$
Compound No. 168  $C_7H_{15}$—Hx—Hx—Hx—Be(3,5F)—$OCF_2CFHCF_3$
Compound No. 169  $C_2H_5$—Hx—Ch—Be(3,5F)—Be(3F)—$OCF_2CF_2H$
Compound No. 170  $C_4H_9$—Hx—Ch—Be(3F)—Be(3,5F)—$OCF_2CFHCF_3$
Compound No. 171  $CF_3C_2H_4$—Hx—Hx—Do—Be(3F)—$OCF_2CFHCF_3$
Compound No. 172  $C_8H_{17}OC_8H_{16}$—Hx—Hx—Do—Be(3,5F)—$OCF_2CF_2H$
Compound No. 173  $C_2H_5$—Be—$C_2H_4$—Be—Be—Be(3F)—$OCF_2CF_2H$
Compound No. 174  $C_2H_5$—Be—$C_2H_4$—Be—Be(3F)—$OCF_2CFHCF_3$
Compound No. 175  $C_4H_9$—Be—$C_2H_4$—Be—Be—Be(3,5F)—$OCF_2CF_2H$
Compound No. 176  $C_6H_{13}$—Be—$C_2H_4$—Be—Be—Be(3,5F)—$OCF_2CFHCF_3$
Compound No. 177  $C_3H_7$—Be—$C_2H_4$—Be—Be(3,5F)—Be—$OCF_2CF_2H$
Compound No. 178  $C_5H_{11}$—Be—$C_2H_4$—Be—Be(3,5F)—Be—$OCF_2CFHCF_3$
Compound No. 179  $C_3H_7$—Be—$C_2H_4$—Be—Be(3F)—Be(3F)—$OCF_2CF_2H$
Compound No. 180  $C_3H_7$—Be—$C_2H_4$—Be(3F)—Be—Be(3F)—$OCF_2CFHCF_3$
Compound No. 181  $C_2H_5$—Be—$C_2H_4$—Be—Be—Be(2,3Cl)—$OCF_2CF_2H$
Compound No. 182  $C_7H_{15}$—Be—$C_2H_4$—Be—Be(2,3F)—Be—$OCF_2CFHCF_3$
Compound No. 183  $C_3H_7O$—Be—$C_2H_4$—Be—Be(3F)—Be(3,5F)—$OCF_2CF_2H$
Compound No. 184  $C_5H_{11}O$—Be—$C_2H_4$—Be—Be(3,5F)—Be(3F)—$OCF_2CF_2H$
Compound No. 185  $C_3H_7OCH_2$—Be—$C_2H_4$—Be(3F)—Be(3F)—Be(3F)—$OCF_2CFHCF_3$
Compound No. 186  $CH_3OC_8H_{16}$—Be—$C_2H_4$—Be(3F)—Be—Be(3,5F)—$OCF_2CF_2H$
Compound No. 187  $C_4H_9$—Be(3F)—$C_2H_4$—Be(3F)—Be(3F)—Be(3F)—$OCF_2CF_2H$
Compound No. 188  $C_5H_{11}$—Be(3F)—$C_2H_4$—Be(3F)—Be(3F)—Be(3F,5Cl)—$OCF_2CFHCF_3$
Compound No. 189  $C_2H_5$—Be—$C_2H_4$—Be(3F)—Be(3F)—Be(3,5F)—$OCF_2CFHCF_3$
Compound No. 190  $C_3H_7$—Be(3F)—$C_2H_4$—Be—Be(3F)—Be(3,5F)—$OCF_2CF_2H$
Compound No. 191  $CFH_2C_4H_8$—Be—$C_2H_4$—Be(3,5F)—Be(3F)—Be(3F)—$OCF_2CF_2H$
Compound No. 192  $C_4H_9$—Be(3F)—$C_2H_4$—Be—Be(3,5F)—Be(3F)—$OCF_2CFHCF_3$ -continued Compound No. 193  $C_7H_{15}$—Be(3F)—$C_2H_4$—Be(3F)—Be(3F)—Be(3,5F)—$OCF_2CF_2H$
Compound No. 194  $C_6H_{13}$—Be(3F)—$C_2H_4$—Be—Be(3,5F)—Be(3,5F)—$OCF_2CFHCF_3$
Compound No. 195  $C_4H_9O$—Be(3F)—$C_2H_4$—Be(3,5F)—Be(3,5F)—Be—$OCF_2CF_2H$
Compound No. 196  $C_6H_{13}O$—Be(3,5F)—$C_2H_4$—Be(3,5F)—Be(3,5F)—Be(3,5F)—$OCF_2CFHCF_3$
Compound No. 197  $C_6H_{13}$—Hx—$C_2H_4(CH_2)_2$—Be—Be—Be(3,5F)—$OCF_2CF_2H$
Compound No. 198  $C_5H_{11}$—Hx—$C_2H_4$—Be—Be(3,5F)—Be(3F)—$OCF_2CFHCF_3$
Compound No. 199  $C_3H_7$—Hx—$C_2H_4$—Be—Be(3F)—Be(3,5F)—$OCF_2CF_2H$
Compound No. 200  $C_2H_5C(CH_3)HC_2H_4$—Hx—$C_2H_4$—Be(3F)—Be(3,5F)—Be(3F)—$OCF_2CF_2H$
Compound No. 201  $C_5H_{11}$—Hx—$C_2H_4$—Hx—Be—Be(3,5F)—$OCF_2CF_2H$
Compound No. 202  $C_3H_7$—Hx—$C_2H_4$—Hx—Be—Be(3F,5Cl)—$OCF_2CFHCF_3$
Compound No. 203  $C_3H_7$—Hx—$C_2H_4$—Hx—Be(3F)—Be(3F)—$OCF_2CFHCF_3$
Compound No. 204  $C_2H_5$—Hx—$C_2H_4$—Hx—Be—Be(2,3F)—$OCF_2CF_2H$
Compound No. 205  $C_4H_9$—Hx—$C_2H_4$—Hx—Be(3F)—Be(3,5F)—$OCF_2CFHCF_3$
Compound No. 206  $C_7H_{15}$—Hx—$C_2H_4$—Hx—Be(3F)—Be(3F,5Cl)—$OCF_2CF_2H$
Compound No. 207  $C_6H_{13}$—Hx—$C_2H_4$—Hx—Be(3,5F)—Be(3F)—$OCF_2CF_2H$
Compound No. 208  $CH_3$—Hx—$C_2H_4$—Hx—Be(3,5F)—Be(3F)—$OCF_2CFHCF_3$
Compound No. 209  $C_5H_{11}$—Hx—$C_2H_4$—Hx—Be(3,5F)—Be(3,5F)—$OCF_2CF_2H$
Compound No. 210  $H_2C=CHCH_2O$—Hx—$C_2H_4$—Hx—Be(3F)—Be(3,5F)—$OCF_2CF_2H$
Compound No. 211  $C_3H_7$—Hx—$C_2H_4$—Ch—Be(3F)—Be(3F)—$OCF_2CF_2H$
Compound No. 212  $H_2C=CHC_2H_4CH=CH$—Hx—$C_2H_4$—Ch—Be(3F)—Be(3,5F)—$OCF_2CFHCF_3$
Compound No. 213  $CH_3OC_3H_6$—Hx—$C_2H_4$—Hx—Do—Be(3F)—$OCF_2CFHCF_3$
Compound No. 214  $C_5H_{11}$—Hx—$C_2H_4$—Hx—Do—Be(3,5F)—$OCF_2CF_2H$
Compound No. 215  $C_2H_5$—Be—Be—$C_2H_4$—Be—Be(3F)—$OCF_2CF_2H$
Compound No. 216  $C_6H_{13}$—Be—Be—$C_2H_4$—Be—$OCF_2CFHCF_3$
Compound No. 217  $C_6H_{13}$—Be—Be—$C_2H_4$—Be—Be(3F)—$OCF_2CF_2H$
Compound No. 218  $C_2H_5$—Be—Be—$C_2H_4$—Be—Be(3,5F)—$OCF_2CF_2H$
Compound No. 219  $C_4H_9$—Be—Be—$C_2H_4$—Be(3,5F)—Be—$OCF_2CFHCF_3$
Compound No. 220  $C_5H_{11}$—Be—Be(3,5F)—$C_2H_4$—Be—$OCF_2CFHCF_3$
Compound No. 221  $C_3H_7$—Be—Be—$C_2H_4$—Be(3F)—Be(3F)—$OCF_2CF_2H$
Compound No. 222  $C_2H_5$—Be—Be(3F)—$C_2H_4$—Be—Be(3F)—$OCF_2CFHCF_3$
Compound No. 223  $C_3H_7O$—Be—Be—$C_2H_4$—Be—Be(2,3Cl)—$OCF_2CF_2H$
Compound No. 224  $C_4H_9$—Be—Be—$C_2H_4$—Be(2,3F)—Be(2,3Cl)—$OCF_2CFHCF_3$
Compound No. 225  $C_7H_{15}$—Be—Be—$C_2H_4$—Be(3F)—Be(3,5F)—$OCF_2CF_2H$
Compound No. 226  $C_2H_5OC_2H_4O$—Be—Be—$C_2H_4$—Be(3,5F)—Be(3F)—$OCF_2CFHCF_3$
Compound No. 227  $C_3H_7$—Be—Be(3,5F)—$C_2H_4$—Be—Be(3F)—$OCF_2CFHCF_3$
Compound No. 228  $CH_3C(CH_3)HCH_2O$—Be—Be(3F)—$C_2H_4$—Be(3F)—Be(3F)—$OCF_2CFHCF_3$
Compound No. 229  $C_5H_{11}OCH_2$—Be—Be(3F)—$C_2H_4$—Be—Be(3,5F)—$OCF_2CF_2H$
Compound No. 230  $CH_3$—Be(3F)—Be(3F)—$C_2H_4$—Be(3F)—Be(3F)—$OCF_2CF_2H$
Compound No. 231  $C_2H_5$—Be—Be(3F)—$C_2H_4$—Be(3F)—Be(3,5F)—$OCF_2CFHCF_3$
Compound No. 232  $C_3H_7$—Be(3F)—Be—$C_2H_4$—Be(3,5F)—Be(3F)—$OCF_2CFHCF_3$
Compound No. 233  $C_5H_{11}$—Be—Be(3,5F)—$C_2H_4$—Be(3F)—Be(3F)—$OCF_2CF_2H$
Compound No. 234  $C_4H_9O$—Be—Be—$C_2H_4$—Be(2,3F)—Be(2,3F)—$OCF_2CFHCF_3$
Compound No. 235  $C_6H_{13}$—Be(3F)—Be(3F)—$C_2H_4$—Be(3F)—Be(3,5F)—$OCF_2CF_2H$
Compound No. 236  $C_4H_9$—Be(3F)—Be—$C_2H_4$—Be(3,5F)—Be(3,5F)—$OCF_2CF_2H$
Compound No. 237  $CH_3OC_2H_4$—Be(3F)—Be(3,5F)—$C_2H_4$—Be(3,5F)—Be—$OCF_2CF_2H$
Compound No. 238  $C_3H_7$—Be(3,5F)—Be(3,5F)—$C_2H_4$—Be(3,5F)—Be(3,5F)—$OCF_2CF_2H$
Compound No. 239  $C_5H_{11}$—Be—Hx—$C_2H_4$—Be—Be(3F)—$OCF_2CF_2H$
Compound No. 240  $C_2H_5$—Hx—Be—$C_2H_4$—Be—Be(3F)—$OCF_2CF_2H$
Compound No. 241  $C_3H_7$—Hx—Be—$C_2H_4$—Be(3F)—Be—$OCF_2CFHCF_3$
Compound No. 242  $C_4H_9$—Hx—Be—$C_2H_4$—Be(3F)—Be(3F)—$OCF_2CF_2H$
Compound No. 243  $C_2H_5$—Hx—Be—$C_2H_4$—Be(2,3F)—Be—$OCF_2CFHCF_3$
Compound No. 244  $C_5H_{11}$—Hx—Be—$C_2H_4$—Be—Be(3,5F)—$OCF_2CFHCF_3$
Compound No. 245  $C_6H_{13}$—Hx—Be—$C_2H_4$—Be(3,5F)—Be—$OCF_2CF_2H$
Compound No. 246  $C_2H_5$—Hx—Be(3F)—$C_2H_4$—Be—Be(3,5F)—$OCF_2CFHCF_3$
Compound No. 247  $C_3H_7$—Hx—Be—$C_2H_4$—Be(3F)—Be(3,5F)—$OCF_2CF_2H$
Compound No. 248  $CFH_2$—Hx—Be—$C_2H_4$—Be(3,5F)—Be(3F)—$OCF_2CF_2H$
Compound No. 249  $C_3H_7OCH_2$—Hx—Be(3F)—$C_2H_4$—Be(3F)—Be(3,5F)—$OCF_2CFHCF_3$
Compound No. 250  $C_7H_{15}$—Hx—Be(3F)—$C_2H_4$—Be(3,5F)—Be(3F)—$OCF_2CF_2H$
Compound No. 251  $C_{18}H_{37}O$—Hx—Be(3,5F)—$C_2H_4$—Be(3F)—Be(3F)—$OCF_2CFHCF_3$
Compound No. 252  $CH_3$—Hx—Be(3F)—$C_2H_4$—Be(3,5F)—Be(3,5F)—$OCF_2CFHCF_3$
Compound No. 253  $C_5H_{11}$—Hx—Be(3,5F)—$C_2H_4$—Be(3F)—Be(3F,5Cl)—$OCF_2CF_2H$
Compound No. 254  $C_3H_7$—Hx—Hx—$C_2H_4$—Be—Be(3F)—$OCF_2CF_2H$
Compound No. 255  $CFH_2CH_2CH=CH$—Hx—Hx—$C_2H_4$—Be—Be(3F)—$OCF_2CFHCF_3$
Compound No. 256  $C_4H_9$—Hx—Hx—$C_2H_4$—Be(3F)—Be—$OCF_2CF_2H$
Compound No. 257  $C_5H_{11}$—Hx—Hx—$C_2H_4$—Be(3F)—Be(3F)—$OCF_2CFHCF_3$
Compound No. 258  $CFH_2C_4H_8$—Hx—Hx—$C_2H_4$—Be—Be(3,5F)—$OCF_2CF_2H$
Compound No. 259  $C_3H_7$—Hx—Hx—$C_2H_4$—Be—Be(3,5F)—$OCF_2CFHCF_3$
Compound No. 260  $C_6H_{13}$—Hx—Hx—$C_2H_4$—Be(3,5F)—Be—$OCF_2CF_2H$
Compound No. 261  $C_2H_5$—Hx—Hx—$C_2H_4$—Be(3F)—Be(3,5F)—$OCF_2CF_2H$
Compound No. 262  $CH_3CH=CHC_2H_4$—Hx—Hx—$C_2H_4$—Be(3F)—Be(3,5F)—$OCF_2CF_2H$
Compound No. 263  $C_7H_{15}$—Hx—Hx—$C_2H_4$—Be(3F)—Be(3,5F)—$OCF_2CFHCF_3$
Compound No. 264  $C_6H_{13}$—Hx—Hx—$C_2H_4$—Be(3,5F)—Be(3F)—$OCF_2CF_2H$
Compound No. 265  $CH_3OCH_2$—Hx—Hx—$C_2H_4$—Be(3,5F)—Be(3F)—$OCF_2CFHCF_3$
Compound No. 266  $F_2C=CH$—Hx—Hx—$C_2H_4$—Be(3,5F)—Be(3F)—$OCF_2CFHCF_3$
Compound No. 267  $C_5H_{11}$—Hx—Hx—$C_2H_4$—Be(2,3F)—Be(2,3F)—$OCF_2CFHCF_3$
Compound No. 268  $C_4H_9$—Hx—Hx—$C_2H_4$—Be(3,5F)—Be(3,5F)—$OCF_2CF_2H$
Compound No. 269  $C_7H_{15}O$—Hx—Hx—$C_2H_4$—Be(3,5F)—Be(3,5F)—$OCF_2CFHCF_3$
Compound No. 270  $H_2C=CHC_2H_4CH=CH$—Hx—Hx—$C_2H_4$—Be(3F)—Be(3,5F)—$OCF_2CF_2H$
Compound No. 271  $C_4H_9$—Hx—Hx—$C_2H_4$—Hx—Be—$OCF_2CF_2H$ -continued

| | |
|---|---|
| Compound No. 272 | $C_2H_5$—Hx—Hx—$C_2H_4$—Hx—Be—$OCF_2CFHCF_3$ |
| Compound No. 273 | $C_5H_{11}$—Hx—Hx—$C_2H_4$—Hx—Be(3F)—$OCF_2CF_2H$ |
| Compound No. 274 | $CH_3OC_3H_6$—Hx—Hx—$C_2H_4$—Hx—Be(3F)—$OCF_2CFHCF_3$ |
| Compound No. 275 | $C_5H_{11}$—Hx—Hx—$C_2H_4$—Hx—Be(3,5F)—$OCF_2CF_2H$ |
| Compound No. 276 | $C_7H_{15}$—Hx—Hx—$C_2H_4$—Hx—Be(3,5F)—$OCF_2CFHCF_3$ |
| Compound No. 277 | $CH_3OCH_2O$—Hx—Hx—$C_2H_4$—Hx—Be(3,5F)—$OCF_2CFHCF_3$ |
| Compound No. 278 | $C_3H_7$—Hx—Hx—$C_2H_4$—Hx—Be(2,3F)—$OCF_2CFHCF_3$ |
| Compound No. 279 | $F(CN)C=CH$—Hx—Hx—$C_2H_4$—Hx—Be(3F)—$OCF_2CF_2H$ |
| Compound No. 280 | $C_3H_7$—Hx—Ch—$C_2H_4$—Be—Be(3,5F)—$OCF_2CF_2H$ |
| Compound No. 281 | $C_5H_{11}$—Hx—Ch—$C_2H_4$—Be(3F)—Be(3,5F)—$OCF_2CFHCF_3$ |
| Compound No. 282 | $C_2H_5$—Hx—Hx—$C_2H_4$—Do—Be(3F)—$OCF_2CF_2H$ |
| Compound No. 283 | $C_4H_9$—Hx—Hx—$C_2H_4$—Do—Be(3F)—$OCF_2CFHCF_3$ |
| Compound No. 284 | $C_7H_{15}O$—Be—Be—Be—$C_2H_4$—Be(3F)—$OCF_2CF_2H$ |
| Compound No. 285 | $C_2H_5$—Be—Be—Be(3F)—$C_2H_4$—Be—$OCF_2CFHCF_3$ |
| Compound No. 286 | $C_5H_{11}$—Be—Be—$C_2H_4$—Be(3,5F)—$OCF_2CF_2H$ |
| Compound No. 287 | $C_3H_7$—Be—Be—Be—$C_2H_4$—Be(3,5F)—$OCF_2CFHCF_3$ |
| Compound No. 288 | $C_3H_7$—Be—Be—Be(3,5F)—$C_2H_4$—Be—$OCF_2CF_2H$ |
| Compound No. 289 | $CH_3OC_4H_8$—Be—Be—Be(3,5F)—$C_2H_4$—Be—$OCF_2CFHCF_3$ |
| Compound No. 290 | $C_6H_{13}$—Be—Be—Be(3F)—$C_2H_4$—Be(3F)—$OCF_2CF_2H$ |
| Compound No. 291 | $C_2H_5$—Be—Be(3F)—Be—$C_2H_4$—Be(3F)—$OCF_2CFHCF_3$ |
| Compound No. 292 | $C_3H_7$—Be—Be—Be—$C_2H_4$—Be(2,3Cl)—$OCF_2CF_2H$ |
| Compound No. 293 | $C_5H_{11}$—Be—Be—Be(2,3F)—$C_2H_4$—Be—$OCF_2CFHCF_3$ |
| Compound No. 294 | $H_2C=CHC_2H_4$—Be—Be—Be(3F)—$C_2H_4$—Be(3,5F)—$OCF_2CF_2H$ |
| Compound No. 295 | $C_4H_9$—Be—Be—Be(3,5F)—$C_2H_4$—Be(3F)—$OCF_2CFHCF_3$ |
| Compound No. 296 | $CH_3$—Be—Be(3F)—Be(3F)—$C_2H_4$—Be(3F)—$OCF_2CFHCF_3$ |
| Compound No. 297 | $F_2C=CHC_2H_4$—Be—Be(3F)—Be—$C_2H_4$—Be(3,5F)—$OCF_2CF_2H$ |
| Compound No. 298 | $C_4H_9$—Be(3F)—Be(3F)—Be(3F)—$C_2H_4$—Be(3F)—$OCF_2CF_2H$ |
| Compound No. 299 | $C_5H_{11}$—Be(3F)—Be(3F)—Be(3F)—$C_2H_4$—Be(3F,5Cl)—$OCF_2CFHCF_3$ |
| Compound No. 300 | $C_2H_5$—Be—Be(3F)—Be(3F)—$C_2H_4$—Be(3,5F)—$OCF_2CFHCF_3$ |
| Compound No. 301 | $C_6H_{13}$—Be(3F)—Be—Be(3F)—$C_2H_4$—Be(3,5F)—$OCF_2CF_2H$ |
| Compound No. 302 | $CFH_2CH_2$—Be—Be(3,5F)—Be(3F)—$C_2H_4$—Be(3F)—$OCF_2CF_2H$ |
| Compound No. 303 | $C_3H_7$—Be(3F)—Be—Be(3,5F)—$C_2H_4$—Be(3F)—$OCF_2CFHCF_3$ |
| Compound No. 304 | $C_5H_{11}$—Be(3F)—Be(3F)—Be(3F)—$C_2H_4$—Be(3,5F)—$OCF_2CF_2H$ |
| Compound No. 305 | $C_3H_7$—Be(3F)—Be—Be(3,5F)—$C_2H_4$—Be(3,5F)—$OCF_2CFHCF_3$ |
| Compound No. 306 | $CH_3OCH_2$—Be(3F)—Be(3,5F)—$C_2H_4$—Be(3,5F)Be—$OCF_2CF_2H$ |
| Compound No. 307 | $C_2H_5$—Be(3,5F)—Be(3,5F)—Be(3,5F)—$C_2H_4$—Be(3,5F)—$OCF_2CFHCF_3$ |
| Compound No. 308 | $C_2H_5$—Hx—Be—Be(3F)—$C_2H_4$—Be(3F)—$OCF_2CF_2H$ |
| Compound No. 309 | $C_3H_7$—Hx—Be—Be(3F)—$C_2H_4$—Be(3F)—$OCF_2CFHCF_3$ |
| Compound No. 310 | $C_4H_9$—Hx—Be—Be(3,5F)—$C_2H_4$—Be(3F)—$OCF_2CF_2H$ |
| Compound No. 311 | $C_5H_{11}$—Hx—Be—Be(3F)—$C_2H_4$—Be(3,5F)—$OCF_2CFHCF_3$ |
| Compound No. 312 | $C_6H_{13}$—Hx—Be—Be(3,5F)—$C_2H_4$—Be(3,5F)—$OCF_2CFHCF_3$ |
| Compound No. 313 | $C_7H_{15}$—Hx—Be(3F)—Be(3,5F)—$C_2H_4$—Be(3F)—$OCF_2CF_2H$ |
| Compound No. 314 | $C_3H_7$—Hx—Be(3,5F)—Be(3F)—$C_2H_4$—Be(3,5F)—$OCF_2CFHCF_3$ |
| Compound No. 315 | $C_2H_5$—Hx—Hx—Be(3F)—$C_2H_4$—Be—$OCF_2CF_2H$ |
| Compound No. 316 | $C_3H_7$—Hx—Hx—Be—$C_2H_4$—Be(3F)—$OCF_2CFHCF_3$ |
| Compound No. 317 | $C_2H_5$—Hx—Hx—Be—$C_2H_4$—Be(3,5F)—$OCF_2CF_2H$ |
| Compound No. 318 | $C_6H_{13}$—Hx—Hx—Be—$C_2H_4$—Be(2,3F)—$OCF_2CFHCF_3$ |
| Compound No. 319 | $C_3H_7$—Hx—Hx—Be(3F)—$C_2H_4$—Be(3F)—$OCF_2CFHCF_3$ |
| Compound No. 320 | $C_5H_{11}$—Hx—Hx—Be(3F)—$C_2H_4$—Be(3,5F)—$OCF_2CF_2H$ |
| Compound No. 321 | $C_5H_{11}$—Hx—Hx—Be(3,5F)—$C_2H_4$—Be(3F)—$OCF_2CFHCF_3$ |
| Compound No. 322 | $C_4H_9$—Hx—Hx—Be(3,5F)—$C_2H_4$—Be(3,5F)—$OCF_2CF_2H$ |
| Compound No. 323 | $C_7H_{15}$—Hx—Hx—Be(3,5F)—$C_2H_4$—Be(3F,5Cl)—$OCF_2CFHCF_3$ |
| Compound No. 324 | $H_2C=CH$—Hx—Hx—$C_2H_4$—Be(3F)—$OCF_2CFHCF_3$ |
| Compound No. 325 | $C_2H_5$—Hx—Hx—Hx—$C_2H_4$—Be(3,5F)—$OCF_2CFHCF_3$ |
| Compound No. 326 | $C_2H_5O$—Hx—Hx—Ch—$C_2H_4$—Be(3,5F)—$OCF_2CFHCF_3$ |
| Compound No. 327 | $C_3H_7$—Be—$C_4H_8$—Be(2,3F)—Be—Be(2,3F)—$OCF_2CFHCF_3$ |
| Compound No. 328 | $CH_3$—Be—$C_4H_8$—Be—Be(3F)—Be(3,5F)—$OCF_2CF_2H$ |
| Compound No. 329 | $C_5H_{11}$—Be—$C_4H_8$—Be(3F)—Be(3F)—Be(3,5F)—$OCF_2CFHCF_3$ |
| Compound No. 330 | $C_3H_7$—Be—$C_4H_8$—Be(3F)—Be(3,5F)—Be(3F)—$OCF_2CFHCF_3$ |
| Compound No. 331 | $C_6H_{13}$—Be—$C_4H_8$—Be—Be(3,5F)—Be(3,5F)—$OCF_2CF_2H$ |
| Compound No. 332 | $C_4H_9$—Be—$C_4H_8$—Be(3,5F)—Be(3,5F)—Be(3F)—$OCF_2CFHCF_3$ |
| Compound No. 333 | $C_2H_5$—Be(3F)—$C_4H_8$—Be(3F)—Be(3,5F)—Be(3,5F)—$OCF_2CFHCF_3$ |
| Compound No. 334 | $C_7H_{15}$—Hx—$C_4H_8$—Be—Be(3F)—Be(3,5F)—$OCF_2CF_2H$ |
| Compound No. 335 | $C_3H_7$—Hx—$C_4H_8$—Be—Be(3F)—Be(3F,5Cl)—$OCF_2CF_2H$ |
| Compound No. 336 | $C_4H_9$—Hx—$C_4H_8$—Be(3F)—Be(3F)—Be(3F)—$OCF_2CFHCF_3$ |
| Compound No. 337 | $C_5H_{11}$—Hx—$C_4H_8$—Be(3,5F)—Be(3F)—Be(3F)—$OCF_2CFHCF_3$ |
| Compound No. 338 | $C_3H_7$—Hx—$C_4H_8$—Be—Be(3,5F)—Be(3,5F)—$OCF_2CFHCF_3$ |
| Compound No. 339 | $C_2H_5O$—Hx—$C_4H_8$—Be(3F)—Be(3,5F)—Be(3,5F)—$OCF_2CFHCF_3$ |
| Compound No. 340 | $C_3H_7$—Hx—$C_4H_8$—Be(3,5F)—Be(3,5F)—Be(3,5F)—$OCF_2CF_2H$ |
| Compound No. 341 | $C_5H_{11}$—Hx—$C_4H_8$—Hx—Be(3F)—Be(3,5F)—$OCF_2CF_2H$ |
| Compound No. 342 | $C_3H_7OCH_2$—Hx—$C_4H_8$—Hx—Be(3F)—Be(3,5F)—$OCF_2CFHCF_3$ |
| Compound No. 343 | $C_3H_7$—Hx—$C_4H_8$—Hx—Be(3,5F)—Be(3F)—$OCF_2CFHCF_3$ |
| Compound No. 344 | $CH_3CH=CH$—Hx—$C_4H_8$—Hx—Be(3,5F)—Be(3F)—$OCF_2CF_2H$ |
| Compound No. 345 | $C_6H_{13}$—Hx—$C_4H_8$—Hx—Be(3,5F)—Be(3F,5Cl)—$OCF_2CFHCF_3$ |
| Compound No. 346 | $F_2C=CH$—Hx—$C_4H_8$—Hx—Be(3,5F)—Be(3,5F)—$OCF_2CFHCF_3$ |
| Compound No. 347 | $C_2H_5$—Hx—$C_4H_8$—Hx—Hx—Be(3,5F)—$OCF_2CF_2H$ |
| Compound No. 348 | $C_5H_{11}$—Hx—$C_4H_8$—Hx—Hx—Be(3,5F)—$OCF_2CFHCF_3$ |
| Compound No. 349 | $C_3H_7$—Hx—$C_4H_8$—Hx—Hx—Be(2,3F)—$OCF_2CF_2H$ |
| Compound No. 350 | $CH_3$—Be—Be—$C_4H_8$—Be—Be(3,5F)—$OCF_2CF_2H$ |

-continued

| | |
|---|---|
| Compound No. 351 | CH$_3$OC$_4$H$_8$—Be—Be(3F)—C$_4$H$_8$—Be(3F)—Be(3F)—OCF$_2$CFHCF$_3$ |
| Compound No. 352 | C$_4$H$_9$—Be—Be—C$_4$H$_8$—Be(3,5F)—Be(3F)—OCF$_2$CF$_2$H |
| Compound No. 353 | C$_8$H$_{17}$—Be—Be—C$_4$H$_8$—Be(3,5F)—Be(3,5F)—OCF$_2$CFHCF$_3$ |
| Compound No. 354 | C$_3$H$_7$—Be—Be(3F)—C$_4$H$_8$—Be(3,5F)—Be(3F)—OCF$_2$CF$_2$H |
| Compound No. 355 | C$_3$H$_7$—Be—Be(3,5F)—C$_4$H$_8$—Be(3,5F)—Be(3F)—OCF$_2$CF$_2$H |
| Compound No. 356 | C$_6$H$_{13}$—Be—Be(3F)—C$_4$H$_8$—Be(3,5F)—Be(3,5F)—OCF$_2$CFHCF$_3$ |
| Compound No. 357 | H$_2$C=CHC$_2$H$_4$—Be(3F)—Be(3,5F)—C$_4$H$_8$—Be(3,5F)—Be(3F)—OCF$_2$CFHCF$_3$ |
| Compound No. 358 | C$_5$H$_{11}$—Be(2,3F)—Be(2,3F)—C$_4$H$_8$—Be(2,3F)—Be(2,3F)—OCF$_2$CF$_2$H |
| Compound No. 359 | C$_3$H$_7$—Hx—Hx—C$_4$H$_8$—Be(3F)—Be(3F)—OCF$_2$CF$_2$H |
| Compound No. 360 | C$_5$H$_{11}$—Hx—Hx—C$_4$H$_8$—Be—Be(2,3F)—OCF$_2$CF$_2$H |
| Compound No. 361 | C$_3$H$_7$—Hx—Hx—C$_4$H$_8$—Be(2,3Cl)—Be—OCF$_2$CFHCF$_3$ |
| Compound No. 362 | CFH$_2$CH$_2$—Hx—Hx—C$_4$H$_8$—Be(3F)—Be(3,5F)—OCF$_2$CFHCF$_3$ |
| Compound No. 363 | C$_6$H$_{13}$—Hx—Hx—C$_4$H$_8$—Be(3F)—Be(3F,5Cl)—OCF$_2$CF$_2$H |
| Compound No. 364 | C$_2$H$_5$—Hx—Hx—C$_4$H$_8$—Be(3,5F)—Be(3F)—OCF$_2$CFHCF$_3$ |
| Compound No. 365 | C$_4$H$_9$—Hx—Hx—C$_4$H$_8$—Be(3,5F)—Be(3,5F)—OCF$_2$CF$_2$H |
| Compound No. 366 | C$_4$H$_9$—Hx—Hx—C$_4$H$_8$—Be(3,5F)—Be(3,5F)—OCF$_2$CFHCF$_3$ |
| Compound No. 367 | C$_7$H$_{15}$—Hx—Hx—C$_4$H$_8$—Be(3,5F)—Be(3F,5Cl)—OCF$_2$CF$_2$H |
| Compound No. 368 | C$_{16}$H$_{33}$O—Hx—Hx—C$_4$H$_8$—Be(3F)—Be(3,5F)—OCF$_2$CF$_2$H |
| Compound No. 369 | C$_3$H$_7$OC$_2$H$_4$—Hx—Hx—C$_4$H$_8$—Be(3F)—Be(3,5F)—OCF$_2$CFHCF$_3$ |
| Compound No. 370 | CF$_3$C$_2$H$_4$—Hx—Hx—C$_4$H$_8$—Be(3,5F)—Be(3F)—OCF$_2$CF$_2$H |
| Compound No. 371 | CH$_3$CFHC$_2$H$_4$—Hx—Hx—C$_4$H$_8$—Be(3,5F)—Be(3,5F)—OCF$_2$CFHCF$_3$ |
| Compound No. 372 | C$_5$H$_{11}$—Hx—Hx—C$_4$H$_8$—Hx—Be(3,5F)—OCF$_2$CFHCF$_3$ |
| Compound No. 373 | C$_3$H$_7$—Hx—Hx—C$_4$H$_8$—Hx—Be(3F,5Cl)—OCF$_2$CFHCF$_3$ |
| Compound No. 374 | C$_2$H$_5$CH=CH—Hx—Hx—C$_4$H$_8$—Hx—Be(3,5F)—OCF$_2$CF$_2$H |
| Compound No. 375 | C$_2$H$_5$—Be—Be—Be(3F)—C$_4$H$_8$—Be(3,5F)—OCF$_2$CF$_2$H |
| Compound No. 376 | C$_9$H$_{19}$—Be—Be—Be(3,5F)—C$_4$H$_8$—Be(3F)—OCF$_2$CFHCF$_3$ |
| Compound No. 377 | C$_4$H$_9$—Be(3F)—Be(3F)—Be(3F)—C$_4$H$_8$—Be(3F)—OCF$_2$CF$_2$H |
| Compound No. 378 | C$_5$H$_{11}$—Be—Be—Be(3,5F)—C$_4$H$_8$—Be(3,5F)—OCF$_2$CFHCF$_3$ |
| Compound No. 379 | C$_6$H$_{13}$—Be—Be(3,5F)—Be(3,5F)—C$_4$H$_8$—Be(3F)—OCF$_2$CFHCF$_3$ |
| Compound No. 380 | C$_5$H$_{11}$—Be(3F)—Be(3F)—Be(3F)—C$_4$H$_8$—Be(3,5F)—OCF$_2$CF$_2$H |
| Compound No. 381 | C$_3$H$_7$O—Be(3F)—Be(3F)—Be(3,5F)—C$_4$H$_8$—Be(3,5F)—OCF$_2$CF$_2$H |
| Compound No. 382 | C$_7$H$_{15}$—Be(3,5F)—Be(3F)—Be(3,5F)—C$_4$H$_8$—Be(3F)—OCF$_2$CFHCF$_3$ |
| Compound No. 383 | C$_3$H$_7$—Be(3,5F)—Be(3,5F)—Be(3F)—C$_4$H$_8$—Be(3F,5Cl)—OCF$_2$CF$_2$H |
| Compound No. 384 | C$_9$H$_{19}$O—Hx—Hx—Be(3F)—C$_4$H$_8$—Be(3,5F)—OCF$_2$CF$_2$H |
| Compound No. 385 | C$_5$H$_{11}$—Hx—Hx—Be(3,5F)—C$_4$H$_8$—Be(3F)—OCF$_2$CFHCF$_3$ |
| Compound No. 386 | C$_{12}$H$_{25}$OCH$_2$—Hx—Hx—Be(3,5F)—C$_4$H$_8$—Be(3F)—OCF$_2$CF$_2$H |
| Compound No. 387 | C$_2$H$_5$—Hx—Hx—Hx—C$_4$H$_8$—Be(3,5F)—OCF$_2$CF$_2$H |
| Compound No. 388 | C$_2$H$_5$C(CH$_3$)HCH$_2$—Hx—Hx—Hx—C$_4$H$_8$—Be(3F,5Cl)—OCF$_2$CFHCF$_3$ |
| Compound No. 389 | C$_6$H$_{13}$—Be—Be—CH$_2$O—Be(2,3F)Be—(2,3F)—OCF$_2$CF$_2$H |
| Compound No. 390 | C$_4$H$_9$—Be—Be(3F)—CH$_2$O—Be(3F)—Be(3F)—OCF$_2$CF$_2$H |
| Compound No. 391 | CH$_3$—Be—Be—CH$_2$O—Be(3,5F)—Be(3F)—OCF$_2$CFHCF$_3$ |
| Compound No. 392 | C$_5$H$_{11}$—Be—Be(3F)—CH$_2$O—Be(3,5F)—Be(3F)—OCF$_2$CF$_2$H |
| Compound No. 393 | C$_3$H$_7$—Be—Be(3,5F)—CH$_2$O—Be(3,5F)—Be(3F)—OCF$_2$CFHCF$_3$ |
| Compound No. 394 | C$_2$H$_5$OC$_2$H$_4$—Be—Be(3F)—CH$_2$O—Be(3,5F)—Be(3,5F)—OCF$_2$CF$_2$H |
| Compound No. 395 | H$_2$C=CHC$_2$H$_4$—Be—Be(3F)—CH$_2$O—Be(3,5F)—Be(3F)—OCF$_2$CFHCF$_3$ |
| Compound No. 396 | CH$_3$—Hx—Hx—CH$_2$O—Be—Be(2,3Cl)—OCF$_2$CF$_2$H |
| Compound No. 397 | C$_3$H$_7$—Hx—Hx—CH$_2$O—Be(3F)—Be(3,5F)—OCF$_2$CFHCF$_3$ |
| Compound No. 398 | C$_2$H$_5$—Hx—Hx—CH$_2$O—Be(3,5F)—Be(3F)—OCF$_2$CFHCF$_3$ |
| Compound No. 399 | C$_3$H$_7$—Hx—Hx—CH$_2$O—Be(3F)—Be(3F,5Cl)—OCF$_2$CF$_2$H |
| Compound No. 400 | C$_3$H$_7$—Hx—Hx—CH$_2$O—H—Be(3,5F)—OCF$_2$CF$_2$H |
| Compound No. 401 | C$_4$H$_9$—Hx—Hx—CH$_2$O—Hx—Be(3,5F)—OCF$_2$CFHCF$_3$ |
| Compound No. 402 | C$_5$H$_{11}$—Hx—Hx—CH$_2$O—Hx—Be(3F,5Cl)—OCF$_2$CF$_2$H |
| Compound No. 403 | C$_6$H$_{13}$—Be—Be—CF$_2$O—Be(3F)—Be(3F)—OCF$_2$CF$_2$H |
| Compound No. 404 | C$_7$H$_{15}$—Be—Be—CF$_2$O—Be(3,5F)—Be(3F)—OCF$_2$CFHCF$_3$ |
| Compound No. 405 | CH$_3$OCH$_2$—Be—Be—CF$_2$O—Be(3F)—Be(3,5F)—OCF$_2$CF$_2$H |
| Compound No. 406 | C$_2$H$_5$—Be—Be(3,5F)—CF$_2$O—Be(3F)—Be(3F)—OCF$_2$CFHCF$_3$ |
| Compound No. 407 | C$_5$H$_{11}$—Be—Be(3,5F)—CF$_2$O—Be(3F)—Be(3,5F)—OCF$_2$CF$_2$H |
| Compound No. 408 | C$_2$H$_5$O—Be(3,5F)—Be(3,5F)—CF$_2$O—Be(3F)Be(3F)—OCF$_2$CF$_2$H |
| Compound No. 409 | C$_5$H$_{11}$—Hx—Hx—CF$_2$O—Be(3F)—Be(3F)—OCF$_2$CF$_2$H |
| Compound No. 410 | C$_3$H$_7$—Hx—Hx—CF$_2$O—Be(3F)—Be(3,5F)—OCF$_2$CFHCF$_3$ |
| Compound No. 411 | C$_3$H$_7$—Hx—Hx—CF$_2$O—Be(3,5F)—Be(3F)—OCF$_2$CF$_2$H |
| Compound No. 412 | C$_5$H$_{11}$OCH$_2$—Hx—Hx—CF$_2$O—Be(3,5F)—Be(3F)—OCF$_2$CF$_2$H |
| Compound No. 413 | C$_5$H$_{11}$—Hx—Hx—CF$_2$O—Be(3,5F)—Be(3F,5Cl)—OCF$_2$CF$_2$H |
| Compound No. 414 | CH$_3$CH=CH—Hx—Hx—CF$_2$O—Be(3,5F)—Be(3,5F)—OCF$_2$CFHCF$_3$ |

The above liquid crystalline compounds of the present invention are exceedingly excellent as a constituent of new liquid crystal compositions having preferable properties, especially nematic liquid crystal compositions, and can suitably be used as a constituent of the liquid crystal compositions for liquid crystal display devices of a TN mode, a STN mode and a TFT mode.

The liquid crystal compositions of the present invention contain at least one of the above liquid crystalline compounds represented by formula (1), and preferably at least one of the above liquid crystalline compounds represented by formula (1) as a first component and at least one of the known liquid crystalline compounds represented by formula (2) and/or formula (3) as a second component.

As the second component, there is suitably used at least one of the compounds represented by formula (2)

$$L_1-(A_5)_a-Z_4-(-A_6-Z_5-)_b-A_4-R_1 \qquad (2)$$

wherein a, b, $A_4$, $A_5$, $A_6$, $Z_4$, $Z_5$, $L_1$ and $R_1$ have the same meanings as defined above.

Specific examples of the compounds represented by formula (2) are illustrated by formulae (2A), (2B) and (2C)

wherein a, $L_1$, $R_1$, $Z_4$ and $Z_5$ have the same meanings as defined above, and $X_3$, $X_4$, $X_5$ and $X_6$ independently of one another represent H or F.

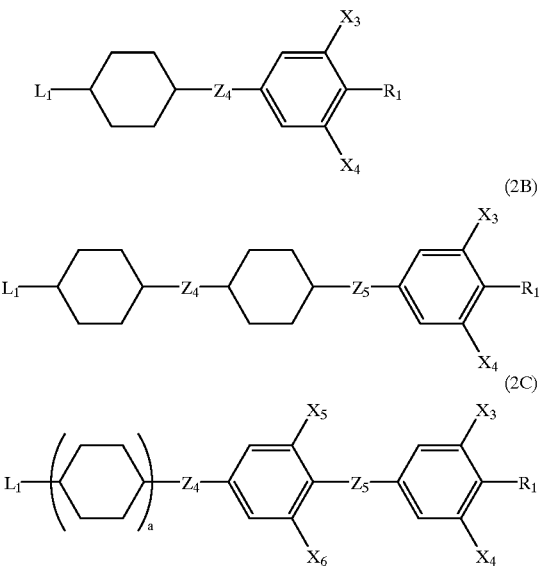

(2A)

(2B)

(2C)

As another second component, there is also suitable at least one of the compounds represented by formula (3)

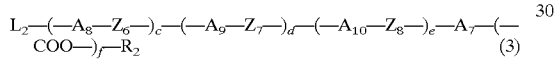

(3)

wherein c, d, e, f, $A_7$, $A_8$, $A_9$, $A_{10}$, $Z_6$, $Z_7$, $Z_8$, $L_2$ and $R_2$ have the same meanings as defined above.

Specific examples of the compounds represented by formula (3) are illustrated by formulae (3A) to (3E).

In formula (3A), c and e represent 0 or 1, ring $A_7$ is selected from trans-1,4-cyclohexylene or 1,4-phenylene which may be substituted with one or more fluorine atoms, ring $A_9$ is selected from trans-1,4-cyclohexylene, 1,4-phenylene or 1,3-dioxane-2,5-diyl, ring $A_{10}$ is selected from trans-1,4-cyclohexylene, 1,4-phenylene or 1,3-pyrimidine-2,5-diyl, bridge $Z_7$ is selected from —$(CH_2)_2$—, —COO— or a single bond, bridge $Z_8$ is a single bond, and terminal group $L_2$ has the same meaning as defined above.

In formula (3B), d represents 0 or 1, terminal group $L_2$ represents an alkyl group of 1–10 carbons, and $X_7$ represents H or F.

In formula (3C), c, d and e represent 0 or 1, rings $A_9$ and $A_{10}$, independently of one another, are selected from trans-1,4-cyclohexylene or 1,4-phenylene, bridges $Z_6$ and $Z_7$, independently of one another, are selected from —COO— or a single bond (—), bridge $Z_8$ is selected from —COO— or ethynylene, terminal group $R_2$ is selected from F, —$OCF_3$, —$OCF_2H$, —$CF_3$, —$CF_2H$ or —$CFH_2$, terminal group $L_2$ represents an alkyl group of 1–10 carbons, and $X_8$ and $X_9$ independently of one another represent H or F.

In formula (3D), f represents 0 or 1, ring $A_7$ is selected from trans-1,4-cyclohexylene or 1,4-phenylene, ring $A_8$ is selected from trans-1,4-cyclohexylene, 1,4-phenylene or 1,3-pyrimidine-2,5-diyl, bridge $Z_6$ is selected from ethynylene, —COO—, —$(CH_2)_2$— or a single bond (—), and terminal groups $R_2$ and $L_2$, independently of one another, are selected from a monovalent saturated organic radical of 1–10 carbons which may have a non-adjacent —O— in the radical, and a monovalent unsaturated organic radical of 2–10 carbons having —CH=CH— at the termi-nal of the radical and/or in the radical in which a non-adjacent —O— may be inserted in the radical.

In formula (3E), e represents 0 or 1, ring $A_7$ is selected from trans-1,4-cyclohexylene or 1,4-phenylene, ring $A_8$ is selected from trans-1,4-cyclohexylene, 1,4-phenylene and 1,3-pyrimidine-2,5-diyl, ring $A_9$ is selected from trans-1,4-cyclohexylene, 1,4-phenylene which may be substituted with one or more fluorine atoms, and 1,3-pyrimidine-2,5-diyl, bridges $Z_6$ and $Z_8$, independently of one another, are selected from —COO—, —$(CH_2)_2$— or a single bond (—), bridge $Z_7$ is selected from —CH=CH—, ethynylene, —COO— or a single bond (—), and terminal groups $R_2$ and $L_2$, independently of one another, are selected from a monovalent saturated organic radical of 1–10 carbons which may have a non-adjacent —O— in the radical, and a monovalent unsaturated organic radical of 2–10 carbons having —CH=CH— at the terminal of the radical and/or in the radical in which a non-adjacent —O— may be inserted in the radical.

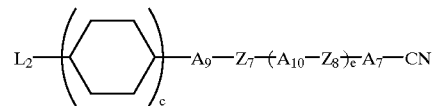

(3A)

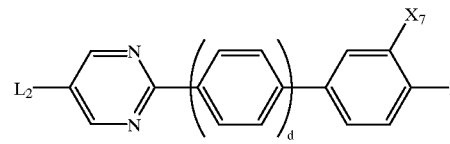

(3B)

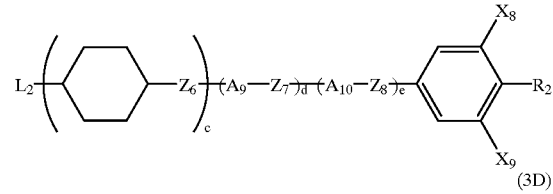

(3C)

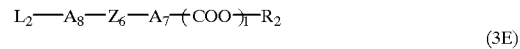

(3D)

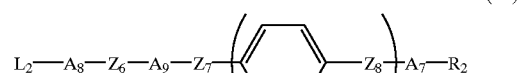

(3E)

More preferable liquid crystal compositions contain at least one of the liquid crystalline compounds represented by formula (1) as a first component, and at least one of the liquid crystalline compounds represented by formula (2) and at least one of the liquid crystalline compounds represented by formula (3) as a second component. Known compounds can further be incorporated as a third component for the purpose of adjusting the threshold voltage, liquid crystal phase temperature range, optical anisotropy, dielectric anisotropy, viscosity and the like.

The content of the liquid crystalline compounds represented by formula (1) is preferably 0.1 to 99% by weight so as to produce excellent properties.

Suitable examples of the compounds included in formula (2A) can include those of formulae (2A-1) to (2A-15), suitable examples of the compounds included in formula (2B) can include those of formulae (2B-1) to (2B-48), and suitable examples of the compounds included in formula (2C) can include those of formulae (2C-1) to (2C-55).

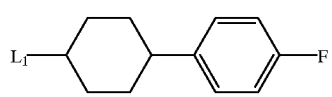 (2A-1)
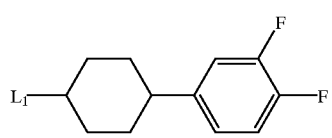 (2A-2)
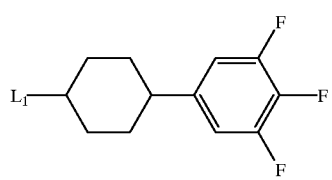 (2A-3)
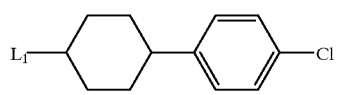 (2A-4)
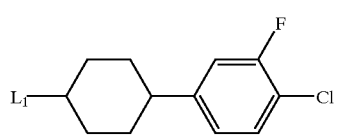 (2A-5)
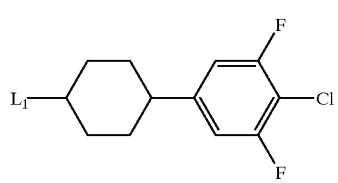 (2A-6)
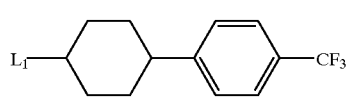 (2A-7)
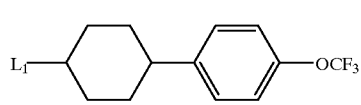 (2A-8)
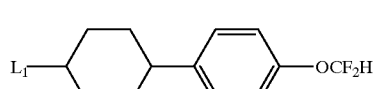 (2A-9)
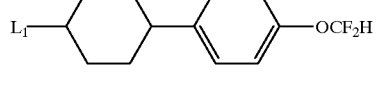 (2A-10)
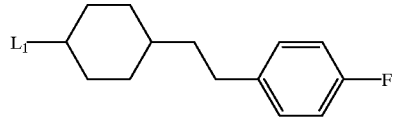 (2A-11)
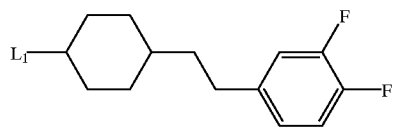

(2A-12)
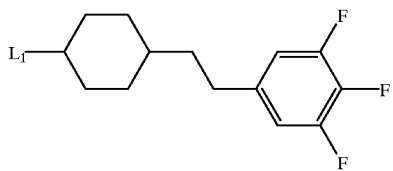
(2A-13)
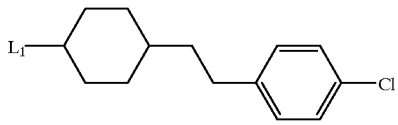
(2A-14)
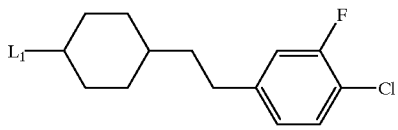
(2A-15)
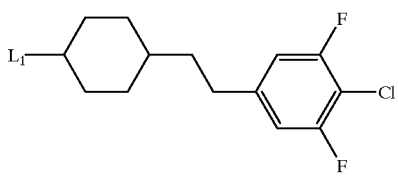
(2B-1)
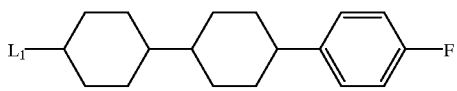
(2B-2)
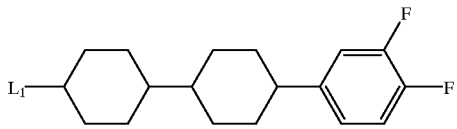
(2B-3)
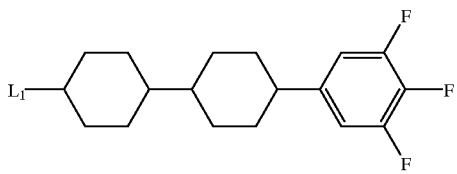
(2B-4)
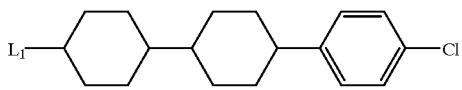
(2B-5)
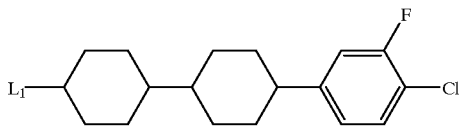
(2B-6)
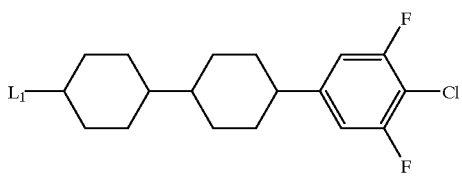

(2B-7)
(2B-8)
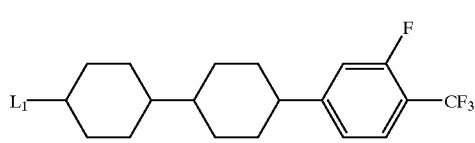
(2B-9)
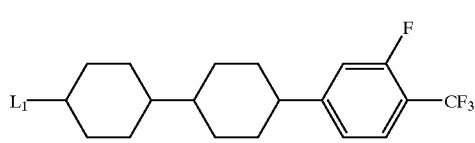
(2B-10)
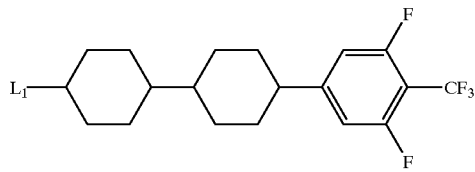
(2B-11)
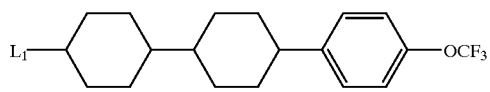
(2B-12)
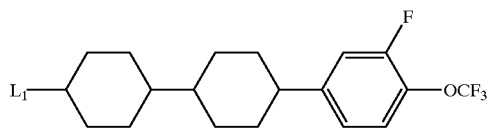
(2B-13)
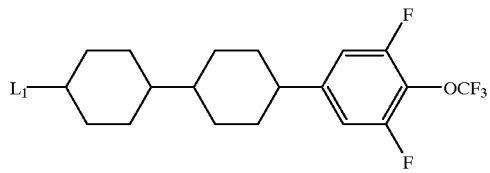
(2B-14)
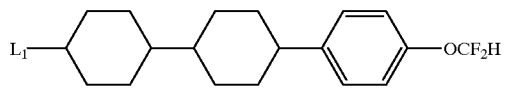
(2B-15)
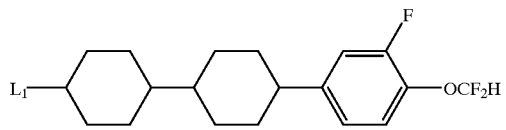
(2B-16)
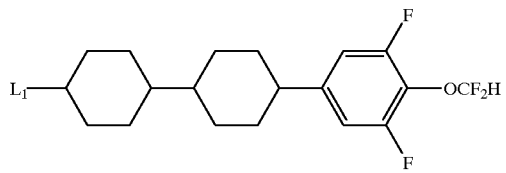

-continued
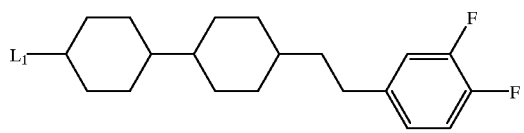
(2B-17)
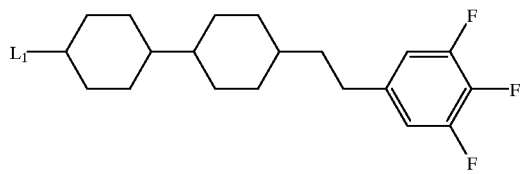
(2B-18)
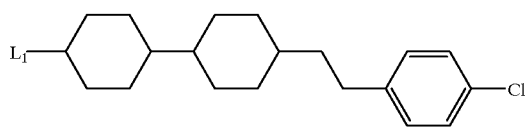
(2B-19)
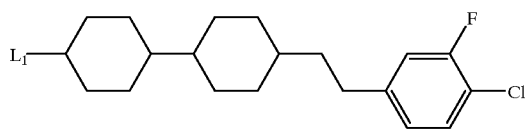
(2B-20)
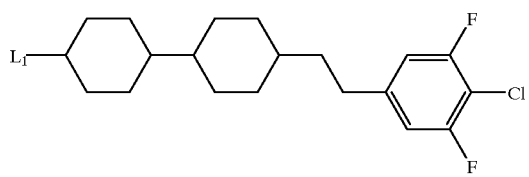
(2B-21)
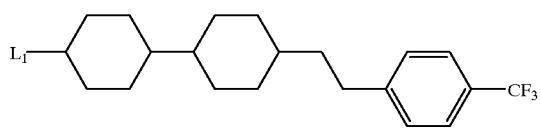
(2B-22)
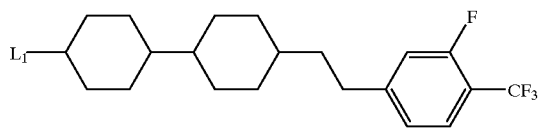
(2B-23)
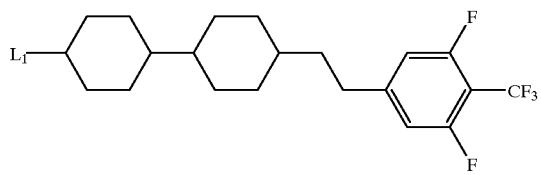
(2B-24)
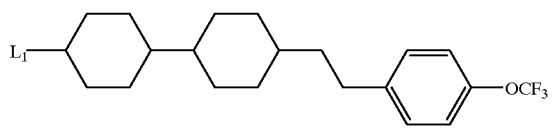
(2B-25)
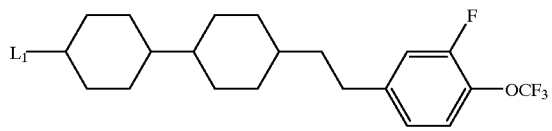
(2B-26)

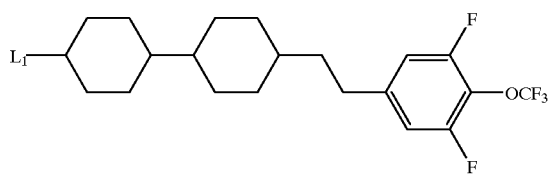
(2B-27)
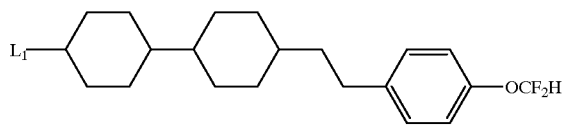
(2B-28)
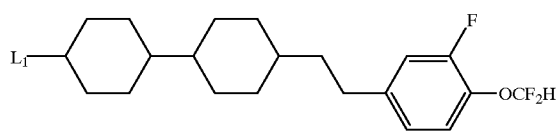
(2B-29)
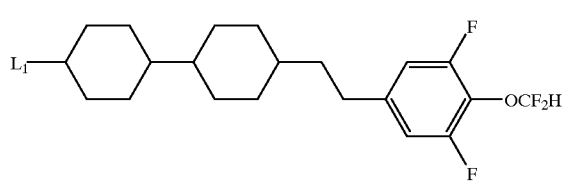
(2B-30)
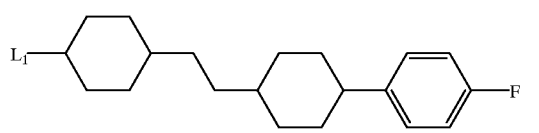
(2B-31)
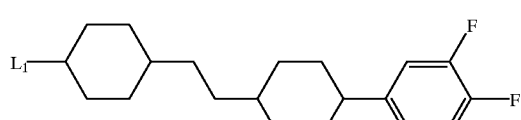
(2B-32)
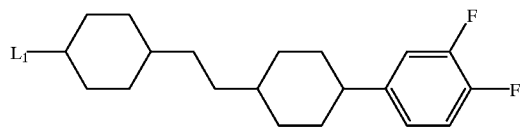
(2B-33)
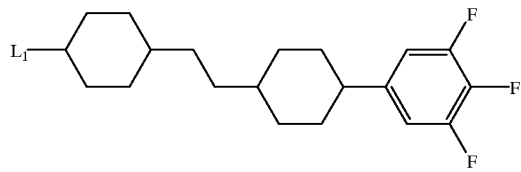
(2B-34)
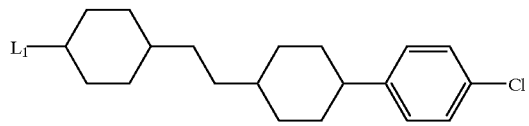
(2B-35)
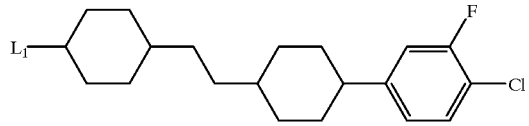

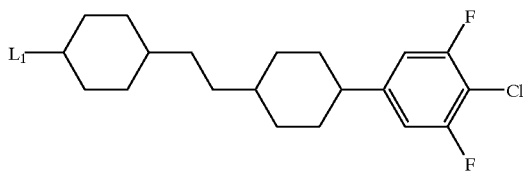
(2B-36)
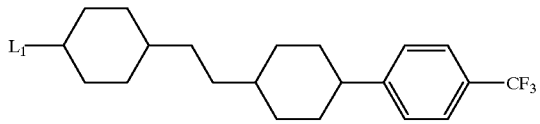
(2B-37)
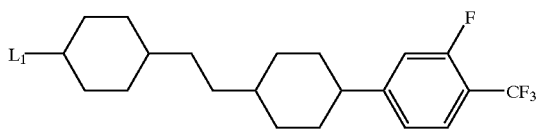
(2B-38)
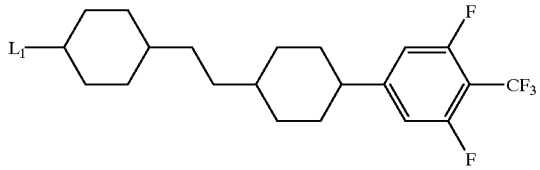
(2B-39)
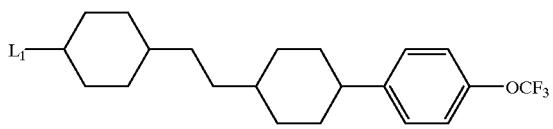
(2B-40)
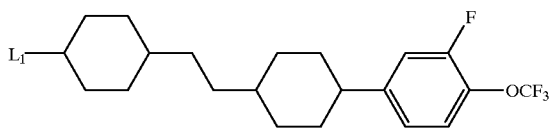
(2B-41)
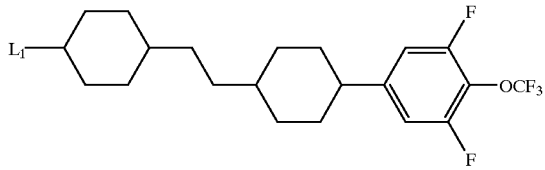
(2B-42)
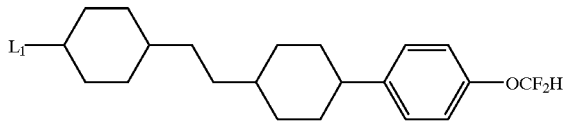
(2B-43)
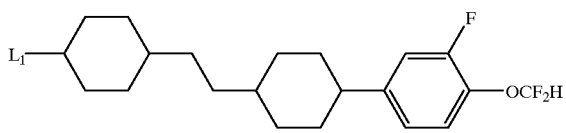
(2B-44)

-continued
(2B-45)
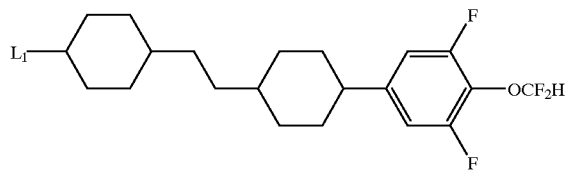
(2B-46)
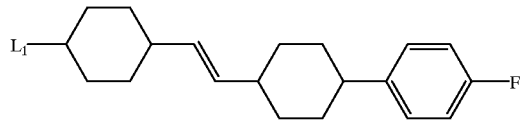
(2B-47)
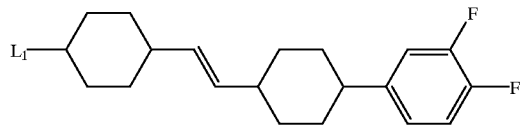
(2B-48)
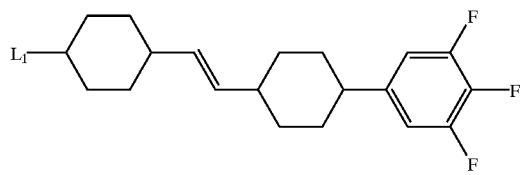
(2C-1)
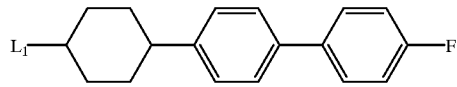
(2C-2)
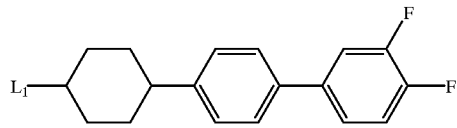
(2C-3)
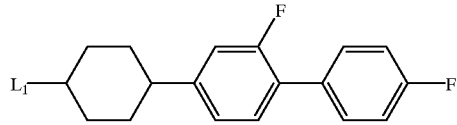
(2C-4)
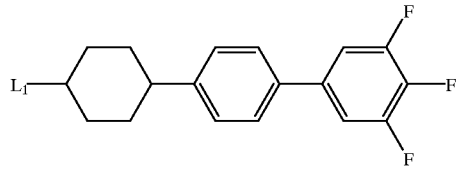
(2C-5)
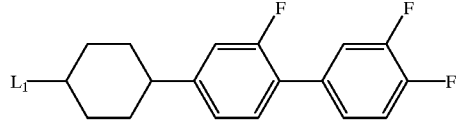
(2C-6)
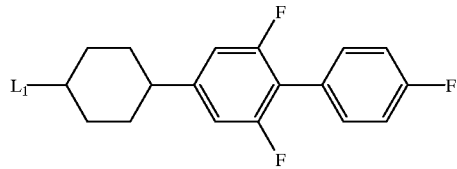

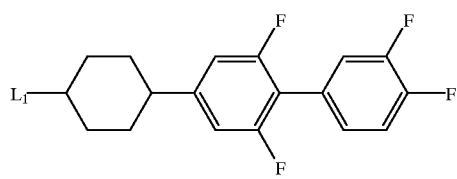 (2C-7)
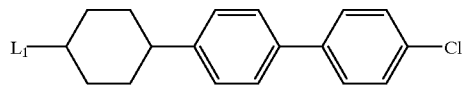 (2C-8)
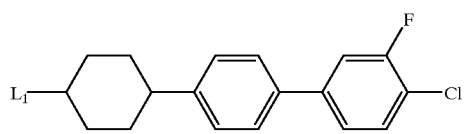 (2C-9)
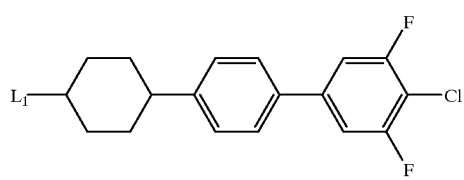 (2C-10)
 (2C-11)
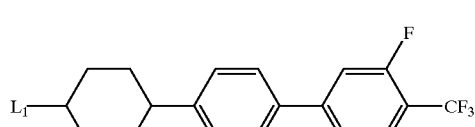 (2C-12)
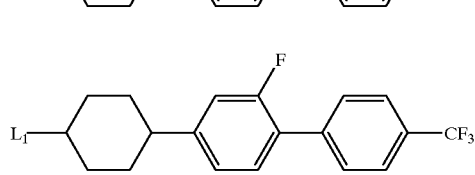 (2C-13)
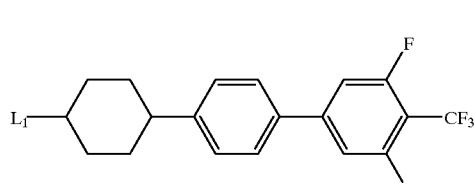 (2C-14)
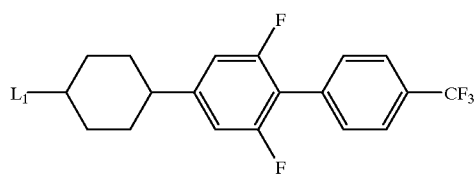 (2C-15)
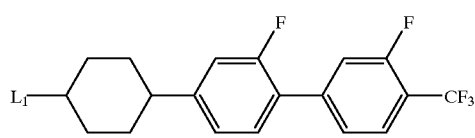 (2C-16)

-continued
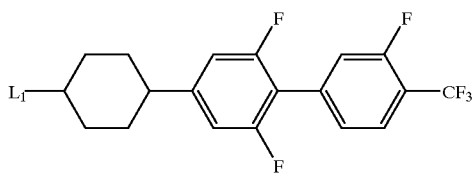
(2C-17)
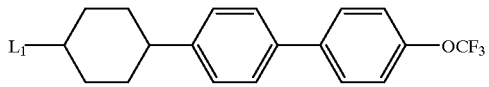
(2C-18)
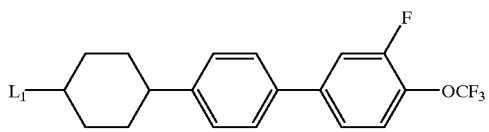
(2C-19)
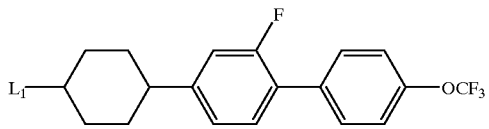
(2C-20)
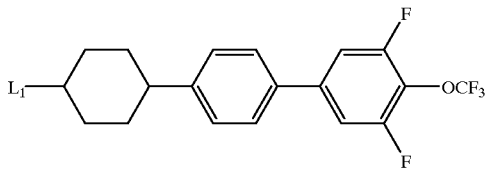
(2C-21)
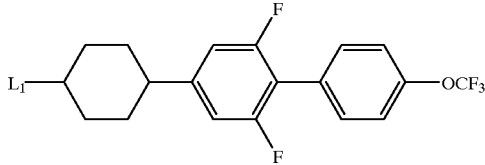
(2C-22)
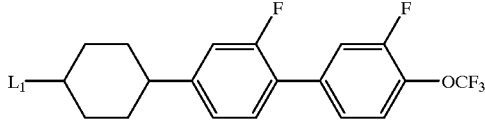
(2C-23)
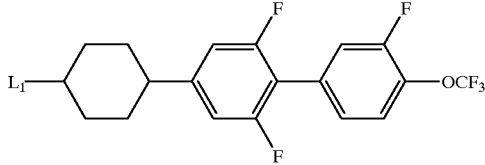
(2C-24)
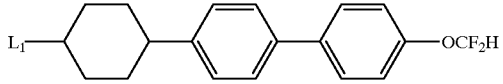
(2C-25)
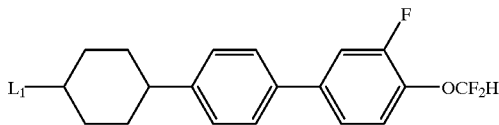
(2C-26)

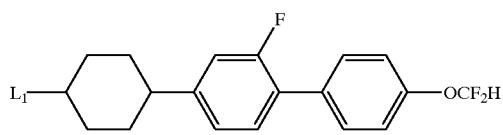
(2C-27)
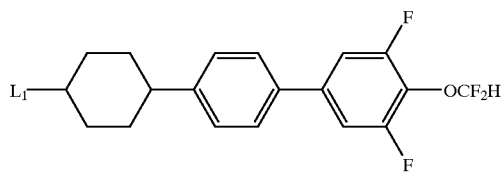
(2C-28)
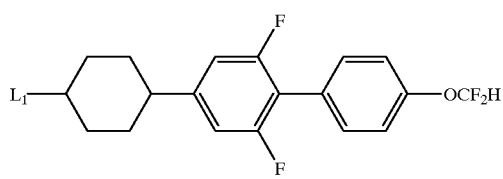
(2C-29)
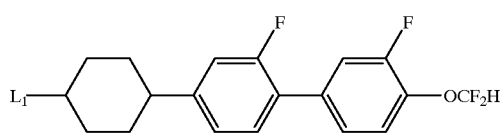
(2C-30)
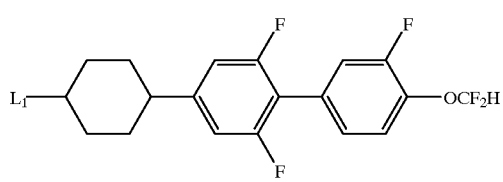
(2C-31)
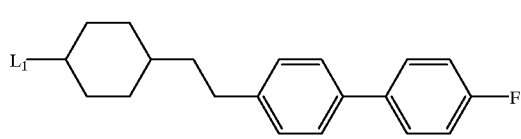
(2C-32)
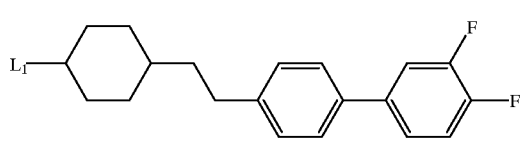
(2C-33)
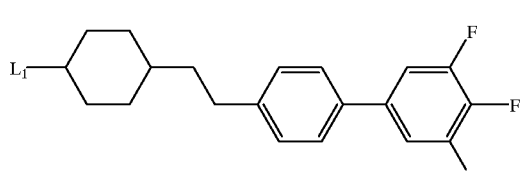
(2C-34)
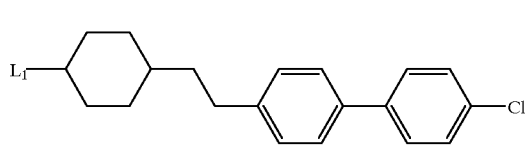
(2C-35)

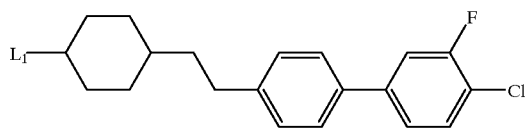
(2C-36)
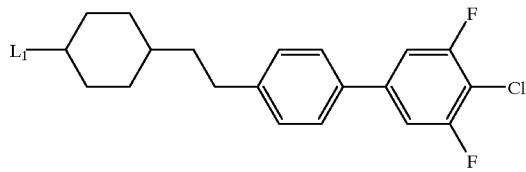
(2C-37)
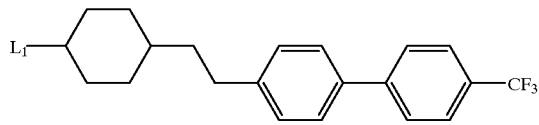
(2C-38)
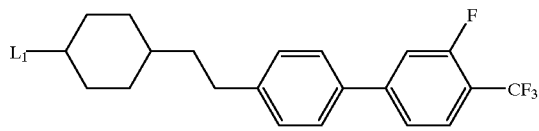
(2C-39)
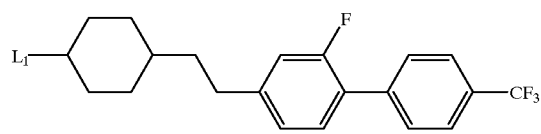
(2C-40)
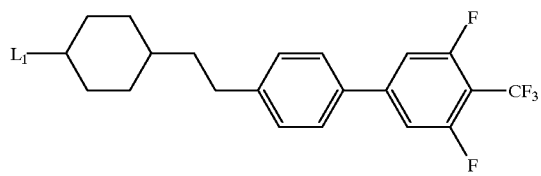
(2C-41)
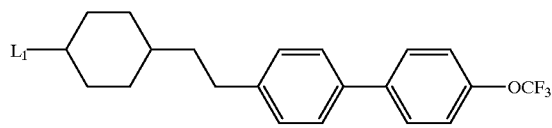
(2C-42)
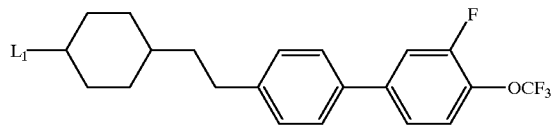
(2C-43)
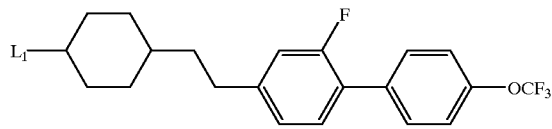
(2C-44)
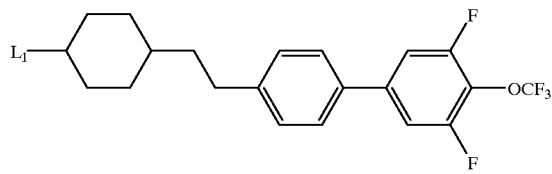
(2C-45)

-continued
(2C-46)
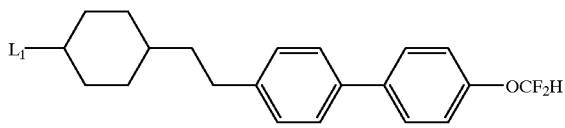
(2C-47)
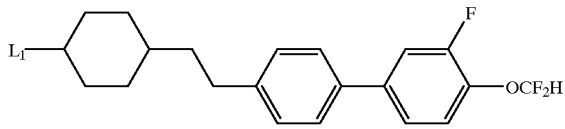
(2C-48)
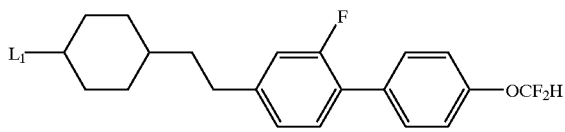
(2C-49)
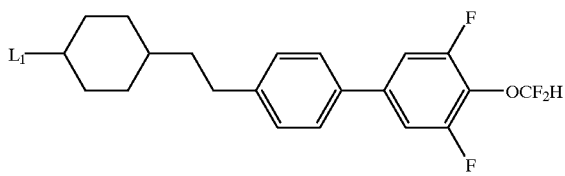
(2C-50)
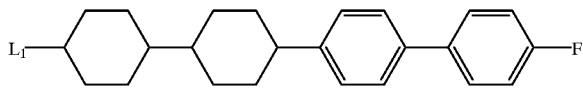
(2C-51)
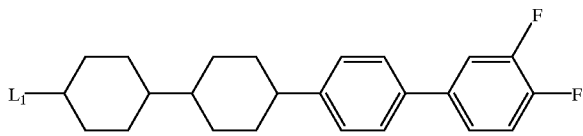
(2C-52)
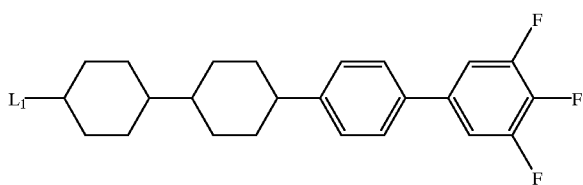
(2C-53)
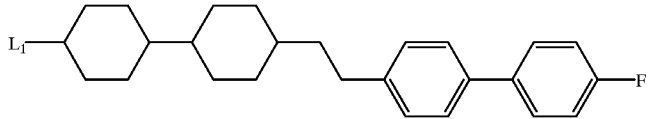
(2C-54)
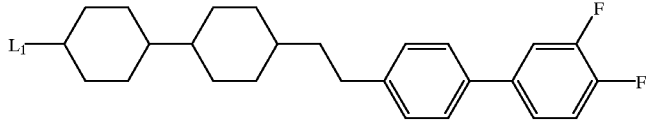
(2C-55)
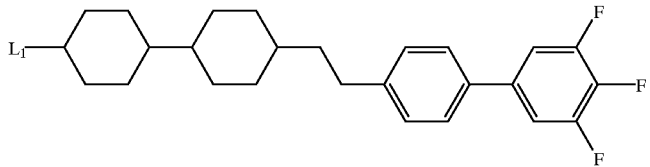

These compounds represented by formula (2) exhibit a positive dielectric anisotropy, and have very excellent thermal and chemical stabilities.

The amount of these compounds used is suitably in the range of 1–99% by weight based on the total amount of the liquid crystal composition, preferably 10–97% by weight, and more preferably 40–95% by weight.

Suitable examples of the compounds included in formulae (3A), (3B) and (3C) as the second component are shown by formulae (3A-1) to (3A-24), (3B-1) to (3B-3) and (3C-1) to (3C-28).

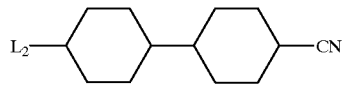
(3A-1)

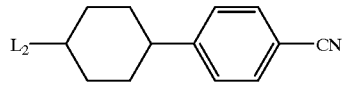
(3A-2)

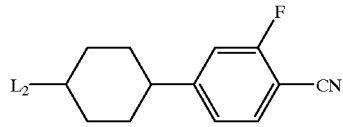
(3A-3)

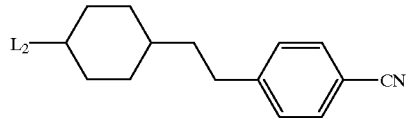
(3A-4)

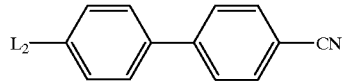
(3A-5)

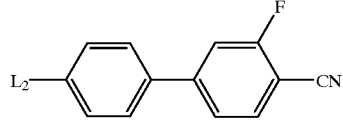
(3A-6)

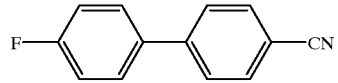
(3A-7)

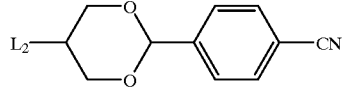
(3A-8)

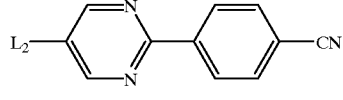
(3A-9)

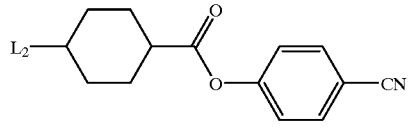
(3A-10)

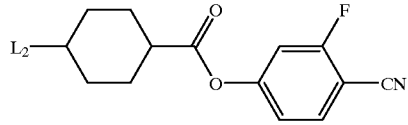
(3A-11)

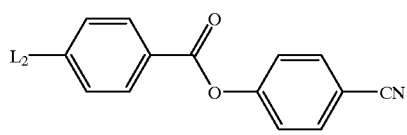
(3A-12)
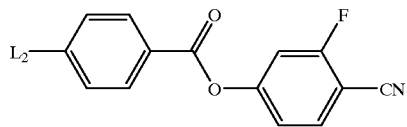
(3A-13)
(3A-14)
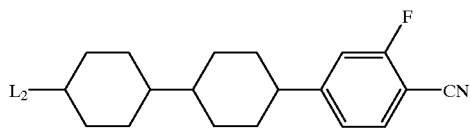
(3A-15)
(3A-16)
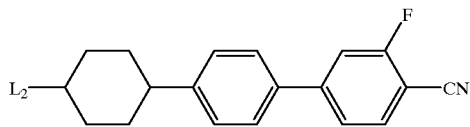
(3A-17)
(3A-18)
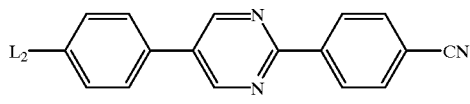
(3A-19)
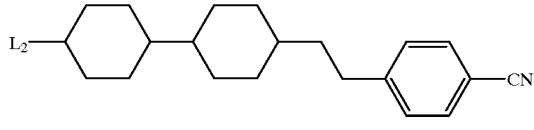
(3A-20)
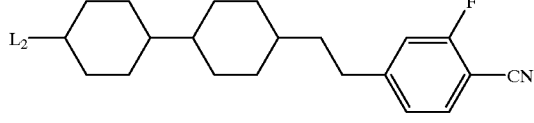
(3A-21)
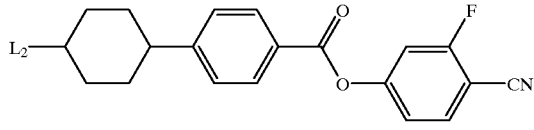
(3A-22)

-continued
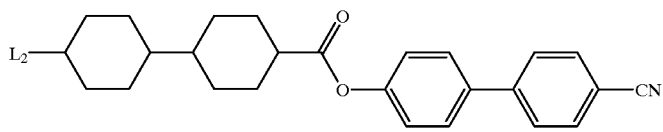
(3A-23)
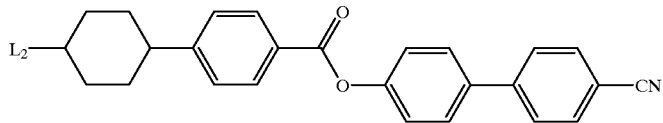
(3A-24)
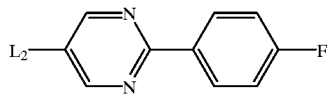
(3B-1)
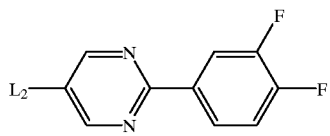
(3B-2)
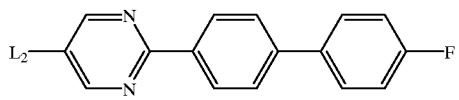
(3B-3)
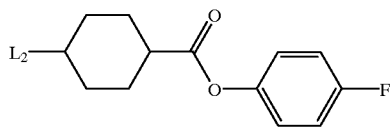
(3C-1)
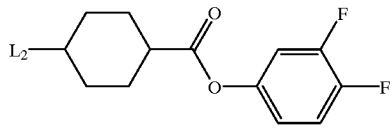
(3C-2)
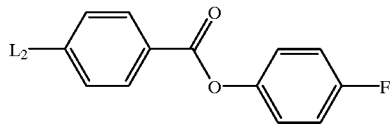
(3C-3)
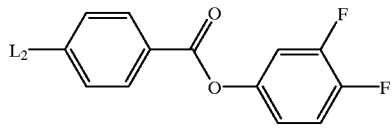
(3C-4)
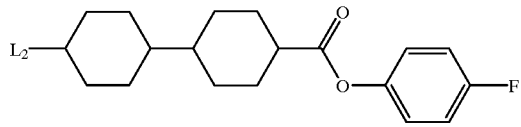
(3C-5)
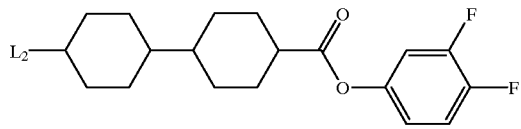
(3C-6)

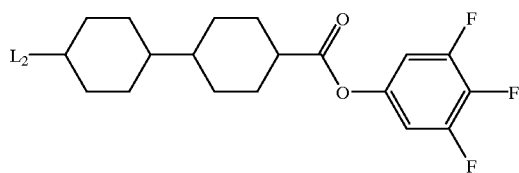
(3C-7)
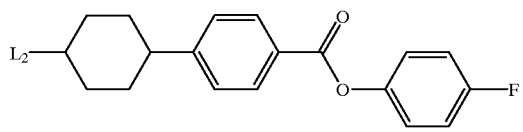
(3C-8)
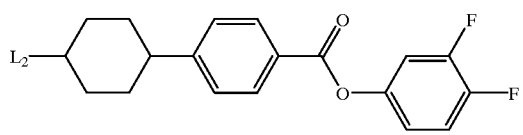
(3C-9)
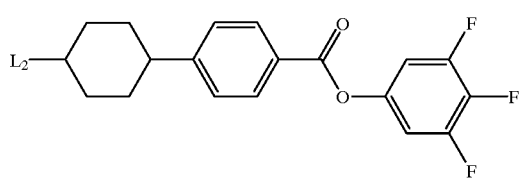
(3C-10)
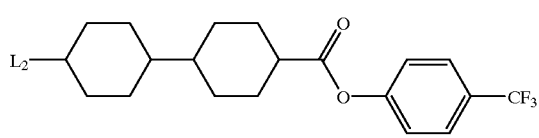
(3C-11)
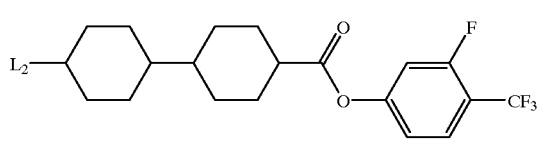
(3C-12)
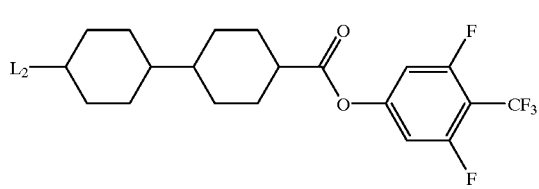
(3C-13)
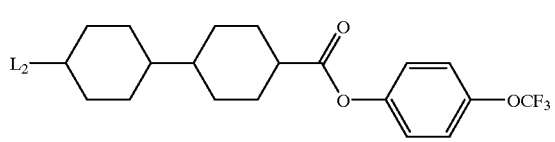
(3C-14)
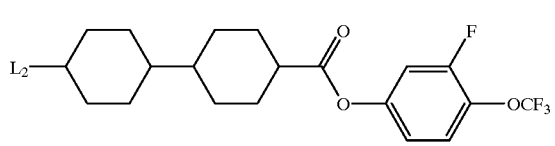
(3C-15)

(3C-16)
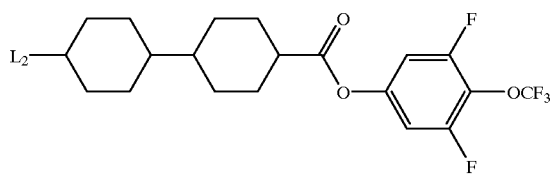
(3C-17)
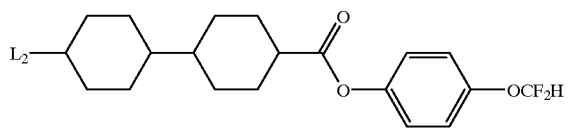
(3C-18)
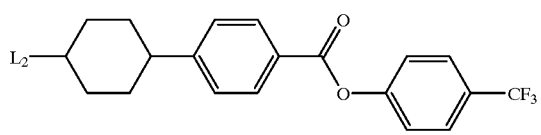
(3C-19)
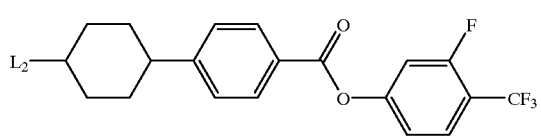
(3C-20)
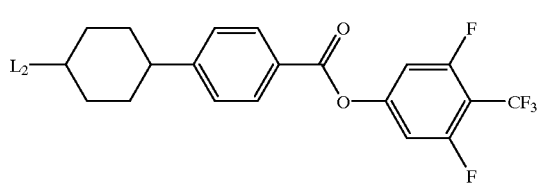
(3C-21)
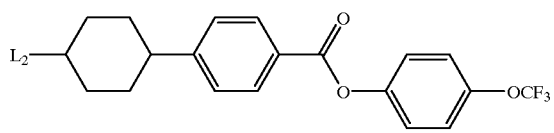
(3C-22)
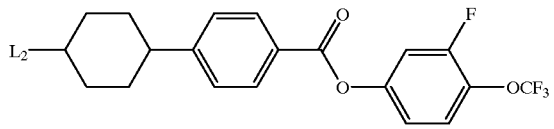
(3C-23)
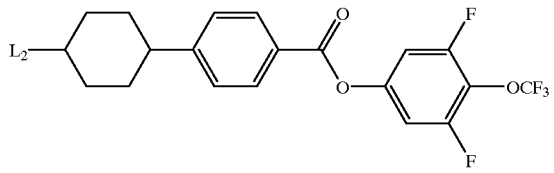
(3C-24)

(3C-25)
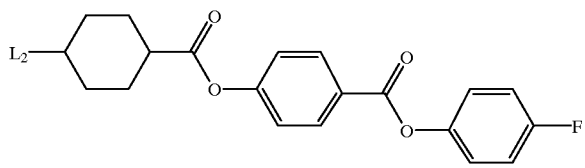

(3C-26)
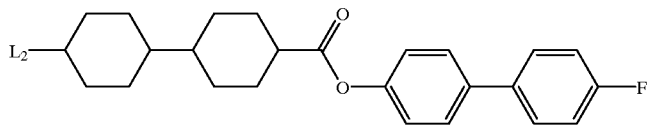

(3C-27)
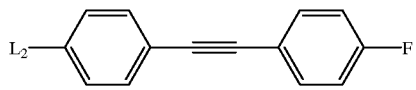

(3C-28)
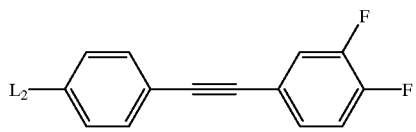

These compounds represented by formulae (3A) to (3C) exhibit a positive and high dielectric anisotropy value, and are used as a component of the compositions especially for the purpose of reducing the threshold voltage. They are also used for the purpose of adjusting the viscosity and optical anisotropy, broadening the liquid crystal phase temperature range, and further, improving the steepness.

Suitable examples of the compounds included in formulae (3D) and (3E) as a second component are shown by formulae (3D-1) to (3D-8) and (3E-1) to (3E-13).

(3D-1)
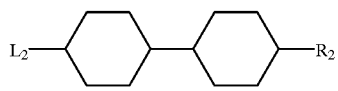

(3D-2)
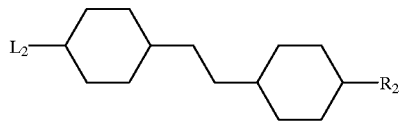

(3D-3)
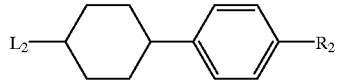

(3D-4)
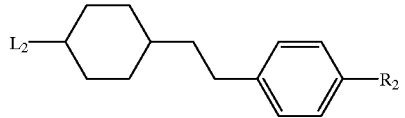

(3D-5)
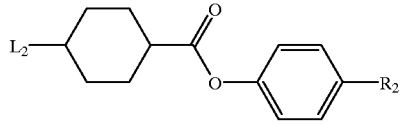

-continued
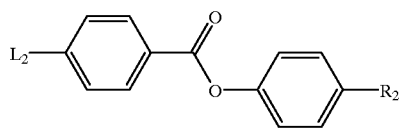
(3D-6)
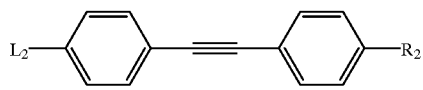
(3D-7)
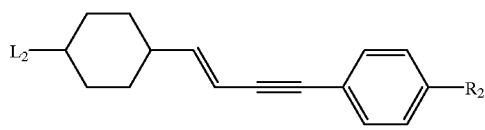
(3D-8)
(3E-1)
(3E-2)
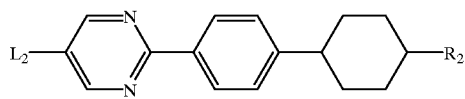
(3E-3)
(3E-4)
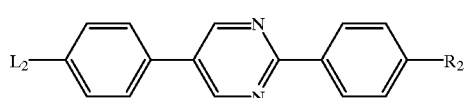
(3E-5)
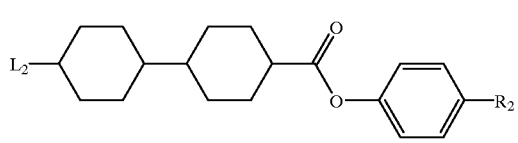
(3E-6)
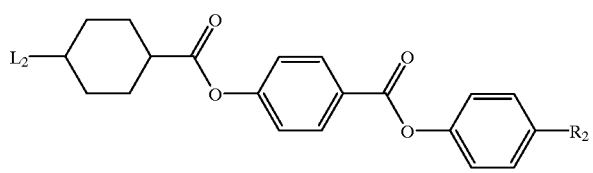
(3E-7)
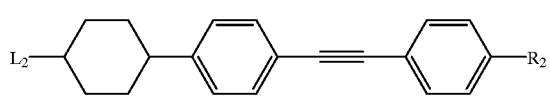
(3E-8)
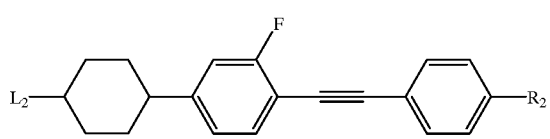
(3E-9)

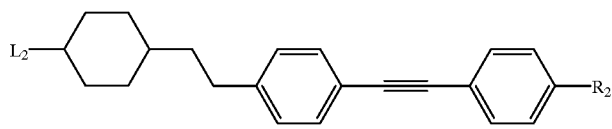

(3E-10)

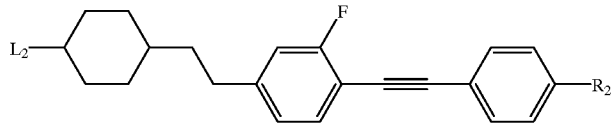

(3E-11)

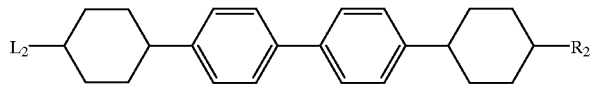

(3E-12)

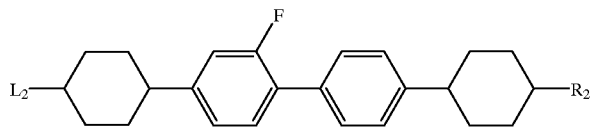

(3E-13)

These compounds represented by formulae (3D) and (3E) exhibit a negative or slightly positive dielectric anisotropy value. The compounds of formula (3D) are used as a component of the compositions mainly for the purpose of lowering the viscosity and adjusting the optical anisotropy, and the compounds of formula (3E) are used mainly for the purpose of broadening the liquid crystal phase temperature range and/or adjusting the optical anisotropy.

The compounds represented by formula (3) are essential for preparing the liquid crystal compositions particularly for a STN or usual TN display mode. The amount of these compounds used is suitably in the range of 1–99% by weight based on the total amount of the liquid crystal composition, preferably 10–97% by weight, and more preferably 40–95% by weight, in the preparation of the liquid crystal compositions for usual STN and TN display modes.

The liquid crystal compositions are generally prepared by known methods per se, for example, by dissolving various components one another at an elevated temperature. If necessary, appropriate additives may be added to improve and optimize the compositions depending on their intended applications.

Such additives are well known to those skilled in the art and described in detail in the literatures. Usually added is a chiral dopant or the like which has the effects of inducing the helical structure of the liquid crystal, adjusting a twist angle as required and preventing a reverse twist.

The liquid crystal compositions can also be used for a GH mode by incorporating therein dichroic dyes such as merocyanines, styryls, azo, azomethines, azoxy, quinophthalones, anthraquinones and tetrazines.

The liquid crystal compositions of the present invention can also be used for NCAP formed by micro-capsulation of nematic liquid crystals, and for polymer dispersion type liquid crystal display devices (PDLCD) wherein a three-dimensional network polymer is formed in the liquid crystal, for example, a polymer network liquid crystal display device (PNLCD), as well as for an electrically controlled birefringence (ECB) mode and a dynamic scattering (DS) mode.

The followings are examples of the liquid crystal compositions comprising the compound selected from the liquid crystalline compounds represented by formula (1) according to the present invention.

For the compounds contained in the liquid crystal compositions, rings are represented by the same abbreviations as mentioned above, an ethynylene bond is represented by —Tr—, parenthesized abbreviations represent a position for substitution and a substituted atom or atoms based on a right terminal group being at the 4-position, and a terminal alkyl group except for those specifically stated is represented only by the number of carbons. The aforementioned compound Nos. are added to the liquid crystalline compounds of the present invention, respectively.

"%" in the composition examples is by weight unless stated otherwise.

| Composition Example 1 | |
|---|---|
| 3-Hx—Hx—C$_2$H$_4$—Be—Be(3,5F)—OCF$_2$CFHCF$_3$ (Compound No. 259) | 20.0% |
| 2-Hx—Hx—Be(3F)—F | 13.0% |
| 3-Hx—Hx—Be(3F)—F | 13.0% |
| 5-Hx—Hx—Be(3F)—F | 14.0% |
| 2-Hx—C$_2$H$_4$—Hx—Be(3F)—F | 8.0% |
| 3-Hx—C$_2$H$_4$—Hx—Be(3F)—F | 4.0% |
| 5-Hx—C$_2$H$_4$—Hx—Be(3F)—F | 8.0% |
| 2-Hx—Be—Be(3F)—F | 5.0% |
| 3-Hx—Be—Be(3F)—F | 5.0% |
| 5-Hx—Be—Be(3F)—F | 10.0% |
| Composition Example 2 | |
| 3-Be—C$_2$H$_4$—Be(3F)—Be(3F)—OCF$_2$CFHCF$_3$ (Compound No. 1) | 12.0% |
| 7-Hx—Be(3F)—F | 10.0% |
| 3-Hx—Be—OC$_2$H$_5$ | 10.0% |
| 2-Hx—Hx—Be(3F)—F | 10.0% |
| 3-Hx—Hx—Be(3F)—F | 10.0% |
| 5-Hx—Hx—Be(3F)—F | 10.0% |
| 2-Hx—Be—Be(3F)—F | 4.0% |
| 3-Hx—Be—Be(3F)—F | 4.0% |
| 5-Hx—Be—Be(3F)—F | 8.0% |
| 3-Hx—Hx—Be—OCF$_3$ | 6.0% |
| 3-Hx—Hx—Be—CH$_3$ | 9.0% |
| 3-Hx—Hx—Be—OCH$_3$ | 5.0% |

| | |
|---|---|
| 3-Hx—Hx—Be—C₃H₇ | 2.0% |
| Composition Example 3 | |
| | |
| 3-Be—C₂H₄—Be(3,5F)—Be(3,5F)—OCF₂CFHCF₃ | 10.0% |
| (Compound No. 49) | |
| 7-Hx—Be(3F)—F | 3.0% |
| 3-Hx—Be—OC₂H₅ | 10.0% |
| 2-Hx—Hx—Be(3F)—F | 10.0% |
| 3-Hx—Hx—Be(3F)—F | 10.0% |
| 5-Hx—Hx—Be(3F)—F | 10.0% |
| 2-Hx—Be—Be(3F)—F | 9.0% |
| 3-Hx—Be—Be(3F)—F | 9.0% |
| 5-Hx—Be—Be(3F)—F | 16.0% |
| 2-Hx—Be—Be—F | 4.0% |
| 3-Hx—Be—Be—F | 4.0% |
| 5-Hx—Be—Be—F | 3.0% |
| 3-Hx—Be—Be(3,5F)—F | 5.0% |
| Composition Example 4 | |
| | |
| 5-Be—C₂H₄—Be—Be(3,5F)—OCF₂CFHCF₃ | 12.0% |
| (Compound No. 35) | |
| 7-Hx—Be—F | 4.0% |
| 3-Hx—C₂H₄—Hx—Be—F | 12.0% |
| 4-Hx—C₂H₄—Hx—Be(3,5F)—F | 10.0% |
| 5-Hx—C₂H₄—Hx—Be(3,5F)—F | 10.0% |
| 3-Hx—Hx—Be(3,5F)—F | 10.0% |
| 4-Hx—Hx—Be(3,5F)—F | 5.0% |
| 3-Hx—Hx—C₂H₄—Be(3,5F)—F | 15.0% |
| 5-Hx—Hx—C₂H₄—Be(3,5F)—F | 10.0% |
| 3-Hx—Be—Be(3,5F)—F | 12.0% |
| Composition Example 5 | |
| | |
| 3-Hx—Hx—C₂H₄—Be—Be(3F)—OCF₂CF₂H | 6.0% |
| (Compound No. 254) | |
| 7-Hx—Be(3,5F)—F | 7.0% |
| 3-Hx—C₂H₄—Hx—Be(3,5F)—F | 12.0% |
| 4-Hx—C₂H₄—Hx—Be(3,5F)—F | 10.0% |
| 3-Hx—Hx—Be(3,5F)—F | 10.0% |
| 4-Hx—Hx—Be(3,5F)—F | 5.0% |
| 3-Hx—Hx—Be(3,5F)—F | 10.0% |
| 3-Hx—Hx—COO—Be(3,5F)—F | 10.0% |
| 4-Hx—Hx—COO—Be(3,5F)—F | 3.0% |
| 5-Hx—Hx—COO—Be(3,5F)—F | 3.0% |
| 2-Hx—Be—COO—Be(3,5F)—F | 3.0% |
| 3-Hx—Do—Be(3,5F)—F | 15.0% |
| 3-Hx—Hx—Be—Be(3,5F)—F | 6.0% |
| Composition Example 6 | |
| | |
| 3-Hx—C₂H₄—Hx—Be(3F)—Be(3F)—OCF₂CF₂H | 10.0% |
| (Compound No. 138) | |
| 5-Hx—CH═CH—Hx—Be(3,5F)—F | 7.0% |
| 3-Hx—Hx—Be—Cl | 7.0% |
| 5-Hx—Hx—Be—Cl | 8.0% |
| 3-Hx—C₂H₄—Hx—Be(3F)—Cl | 7.0% |
| 5-Hx—C₂H₄—Hx—Be(3F)—Cl | 8.0% |
| 2-Hx—Hx—Be(3F)—F | 3.0% |
| 3-Hx—Hx—Be(3F)—F | 3.0% |
| 5-Hx—Hx—Be(3F)—F | 3.0% |
| 3-Hx—Hx—Be(3F)—OCF₂H | 6.0% |
| 2-Hx—Be—Be(3F)—F | 4.0% |
| 3-Hx—Be—Be(3F)—F | 4.0% |
| 5-Hx—Be—Be(3F)—F | 8.0% |
| 3-Hx—Be—Be(3,5F)—F | 6.0% |
| 5-Hx—Be—Be(3,5F)—F | 6.0% |
| 3-Hx—C₂H₄—Hx—Be(3,5F)—F | 5.0% |
| 5-Hx—C₂H₄—Hx—Be(3,5F)—F | 5.0% |
| Composition Example 7 | |
| | |
| 3-Hx—C₂H₄—Hx—Be(3F)—Be(3F)—OCF₂CF₂H | 8.0% |
| (Compound No. 138) | |
| 5-Hx—C₂H₄—Be(3F)—F | 10.0% |
| 7-Hx—Be—F | 7.0% |
| 2-Hx—Hx—Be(3F)—F | 15.0% |
| 3-Hx—Hx—Be(3F)—F | 15.0% |
| 5-Hx—Hx—Be(3F)—F | 15.0% |
| 2-Hx—C₂H₄—Hx—Be(3F)—F | 8.0% |
| 3-Hx—C₂H₄—Hx—Be(3F)—F | 4.0% |
| 5-Hx—C₂H₄—Hx—Be(3F)—F | 8.0% |
| 3-Hx—C₂H₄—Be—Tr—Be—C₂H₅ | 5.0% |

| | |
|---|---|
| 3-Hx—Hx—C₄H₉ | 5.0% |
| Composition Example 8 | |
| | |
| 3-Hx—Hx—C₂H₄—Be—Be(3F)—OCF₂CF₂H | 7.0% |
| (Compound No. 254) | |
| CH₃CH═CHC₂H₄—Be—COO—Be(3,5F)—CN | 7.0% |
| 3-Hx—Be—CN | 25.0% |
| 3-Hx—Be—OC₂H₅ | 4.0% |
| 3-Hx—Hx—C₄H₉ | 11.0% |
| 3-Hx—Hx—C₅H₁₁ | 5.0% |
| 3-Hx—Hx—Be—CH₃ | 10.0% |
| 3-Hx—Hx—Be—C₃H₇ | 11.0% |
| 3-Hx—Be(3F)—Tr—Be—C₂H₅ | 8.0% |
| 3-Hx—C₂H₄—Be—Tr—Be—C₂H₅ | 4.0% |
| 3-Hx—C₂H₄—Be—Tr—Be—C₃H₇ | 4.0% |
| 3-Hx—C₂H₄—Be—Tr—Be—C₄H₉ | 4.0% |
| Composition Example 9 | |
| | |
| 5-Be—C₂H₄—Be—Be(3,5F)—OCF₂CFHCF₃ | 6.0% |
| (Compound No. 35) | |
| H₂C═CHC₂H₄—Hx—Be—CN | 10.0% |
| CH₃CH═CHC₂H₄—Hx—Be—CN | 10.0% |
| 3-Hx—Be—CN | 15.0% |
| 3-Hx—Hx—C₄H₉ | 12.0% |
| 2-Be—Tr—Be—OCH₃ | 7.0% |
| 3-Hx—Hx—Be—CH₃ | 8.0% |
| 3-Hx—Hx—Be—C₃H₇ | 12.0% |
| 3-Hx—Hx—Be—F | 4.0% |
| 2-Hx—C₂H₄—Be—Tr—Be—C₂H₅ | 4.0% |
| 3-Hx—C₂H₄—Be—Tr—Be—C₂H₅ | 4.0% |
| 3-Hx—C₂H₄—Be—Tr—Be—C₃H₇ | 4.0% |
| 3-Hx—C₂H₄—Be—Tr—Be—C₄H₉ | 4.0% |
| Composition Example 10 | |
| | |
| 3-Hx—Hx—C₂H₄—Be—Be(3,5F)—OCF₂CFHCF₃ | 7.0% |
| (Compound No. 259) | |
| H₂C═CHC₂H₄—Hx—Be—CN | 10.0% |
| CH₃CH═CHC₂H₄—Hx—Be—CN | 10.0% |
| 3-Hx—Be—CN | 18.0% |
| 5-Hx—Be—CN | 4.0% |
| CH₃OCH₂—Hx—Be—CN | 6.0% |
| 3-Hx—Hx—C₄H₉ | 10.0% |
| CH₃OCH₂—Hx—Hx—C₅H₁₁ | 5.0% |
| 2-Be—Tr—Be—CH₃ | 3.0% |
| 2-Be—Tr—Be—OCH₃ | 8.0% |
| 3-Hx—Hx—Be—CH₃ | 6.0% |
| 3-Hx—Hx—Be—C₃H₇ | 8.0% |
| 3-Hx—Hx—Be—CN | 5.0% |
| Composition Example 11 | |
| | |
| 3-Hx—C₂H₄—Hx—Be(3F)—Be(3F)—OCF₂CF₂H | 7.0% |
| (Compound No. 138) | |
| 3-Be—COO—Be(3F)—CN | 4.0% |
| C₃H₇OCH₂—Be—COO—Be(3F)—CN | 4.0% |
| 5-Py—Be—CN | 8.0% |
| H₂C═CH—Hx—Be—CN | 8.0% |
| CH₃CH═CH—Hx—Be—CN | 8.0% |
| 3-Hx—Be—OC₂H₅ | 4.0% |
| 5-Hx—Hx—CH═CH₂ | 14.0% |
| 3-Hx—Hx—CH₂CH═CHCH₃ | 7.0% |
| H₂C═CH—Hx—Hx—Be—CH₃ | 15.0% |
| H₂C═CHC₂H₄—Hx—Hx—Be—CH₃ | 7.0% |
| 3-Hx—Be—Tr—Be—C₂H₅ | 5.0% |
| 3-Hx—C₂H₄—Be—Tr—Be—C₂H₅ | 5.0% |
| 3-Hx—C₂H₄—Be—Tr—Be—C₃H₇ | 4.0% |
| Composition Example 12 | |
| | |
| 3-Hx—C₂H₄—Hx—Be(3F)—Be(3F)—OCF₂CF₂H | 9.0% |
| (Compound No. 138) | |
| C₂H₅OCH₂—Be—COO—Be(3F)—CN | 4.0% |
| C₃H₇OCH₂—Be—COO—Be(3F)—CN | 13.0% |
| 2-Hx—Be(3F)—CN | 7.0% |
| 3-Hx—Be(3F)—CN | 13.0% |
| 5-Py—Be(3F)—F | 5.0% |
| 3-Hx—Hx—C₄H₉ | 4.0% |
| 2-Be—Tr—Be—CH₃ | 3.0% |
| 3-Py—Be—Be—F | 6.0% |
| 4-Py—Be—Be—F | 5.0% |
| 3-Hx—Hx—Be—CH₃ | 10.0% |

-continued

| | |
|---|---|
| 3-Hx—C$_2$H$_4$—Be—Tr—Be—C$_2$H$_5$ | 5.0% |
| 3-Hx—C$_2$H$_4$—Be—Tr—Be—C$_3$H$_7$ | 4.0% |
| 3-Hx—Be(3F)—Tr—Be—C$_2$H$_5$ | 6.0% |
| 3-Hx—Be(3F)—Tr—Be—C$_3$H$_7$ | 6.0% |
| Composition Example 13 | |
| 5-Be—Hx—C$_2$H$_4$—Be—Be(3F)—OCF$_2$CF$_2$H (Compound No. 239) | 6.0% |
| 3-Hx—Hx—C$_2$H$_4$—Be—Be(3,5F)—OCF$_2$CFHCF$_3$ (Compound No. 259) | 14.0% |
| 2-Hx—Hx—Be(3F)—F | 13.0% |
| 3-Hx—Hx—(3F)—F | 13.0% |
| 5-Hx—Hx—Be(3F)—F | 14.0% |
| 2-Hx—C$_2$H$_4$—Hx—Be(3F)—F | 8.0% |
| 3-Hx—C$_2$H$_4$—Hx—Be(3F)—F | 4.0% |
| 5-Hx—C$_2$H$_4$—Hx—Be(3F)—F | 8.0% |
| 2-Hx—Be—Be(3F)—F | 5.0% |
| 3-Hx—Be—Be(3F)—F | 5.0% |
| 5-Hx—Be—Be(3F)—F | 10.0% |
| Composition Example 14 | |
| 5-Be(3F)—C$_2$H$_4$—Be(3F)—Be(3,5F)—OCF$_2$CFHCF$_3$ (Compound No. 53) | 15.0% |
| 7-HxB—F | 4.0% |
| 3-Hx—C$_2$H$_4$—Hx—Be—F | 12.0% |
| 4-Hx—C$_2$H$_4$—Hx—Be(3,5F)—F | 9.0% |
| 5-Hx—C$_2$H$_4$—Hx—Be(3,5F)—F | 9.0% |
| 3-Hx—Hx—Be(3,5F)—F | 9.0% |
| 4-Hx—Hx—Be(3,5F)—F | 5.0% |
| 3-Hx—Hx—C$_2$H$_4$—Be(3,5F)—F | 15.0% |
| 5-Hx—Hx—C$_2$H$_4$—Be(3,5F)—F | 10.0% |
| 3-Hx—Be—Be(3,5F)—F | 12.0% |

EXAMPLES

The present invention is further illustrated by the following examples.

A) Preparation of a Fluoro-substituted Alkyl Ether Compound (liquid crystalline compound)

In the following examples, C represents crystal, SA represents a smectic A phase, SB represents a smectic B phase, SX represents a smectic phase wherein the phase structure is not analyzed, N represents a nematic phase, Iso represents a isotropic phase, and the unit of the phase transition temperature is all in terms of ° C. The parenthesized phase shows a monotropic phase.

Example 1

Preparation of Compound No. 1: 3-fluoro-4-(1,1,2,3,3,3-hexafluoropropoxy)-2'-fluoro-4'-(2-(4-propylphenyl)ethyl)-biphenyl (the compound of formula (1) wherein m is 0, Rf is —OCF$_2$CFHCF$_3$, Ra is C$_3$H$_7$—(3), A$_0$ and A$_2$ are a F-substituted 1,4-phenylene group (Be(3F)), A$_1$ is a 1,4-phenylene group (Be), Z$_1$ is —CH$_2$CH$_2$—, and Z$_2$ is a single bond)

3.0 g (10.5 mmol) of 2-fluoro-4-(2-(4-propylphenyl)ethyl)phenyl boron acid, 4.6 g (13.6 mmol) of 3-fluoro-4-(1,1,2,3,3,3-hexafluoro)bromobenzene, 2.9 g (21.0 mmol) of K$_2$CO$_3$, 0.3 g of 5%-Pd/C, 15 ml of water and 30 ml of a mixed solvent of ethanol/toluene (1/1) were refluxed for 12 hours. 50 ml of toluene was added to the reaction mixture, and the resulting organic layer was washed with water three times and dried over anhydrous magnesium sulfate. The solvent was distilled off under reduced pressure, and the residue was subjected to a silica gel column chromatography (eluent: heptane/ethyl acetate) to afford 4.3 g of the crude 3-fluoro-4-(1,1,2,3,3,3-hexafluoropropoxy)-2'-fluoro-4'-(2-(4-propylphenyl)ethyl) biphenyl, which was then recrystallized from a mixed solvent of ethanol/ethyl acetate to give 0.8 g of the title compound (Compound No. 1). Yield: 15.8%

This compound exhibited a liquid crystal phase having the phase transition temperature:

C 75.0–76.1 (N 47.2) Iso

Each of the spectrum data well identified the structure thereof.

MS: 502 (M$^+$);

$^1$H-NMR (CDCl$_3$, TMS Internal standard) δ (ppm): 0.94 (t, 3H); 1.63 (qt, 2H); 2.57 (t, 2H); 2.93 (s, 4H); 4.79–5.35 (dtq, 1H); 6.93–7.45 (m, 10H)

The liquid crystalline Compound No. 49 was synthesized according to the method of Example 1. Compound No. 49: C$_3$H$_7$—Be—(CH$_2$)$_2$—Be(3,5F)—Be(3,5F)—OCF$_2$CFHCF$_3$ C 63.1–64.0 Iso The Compounds Nos. 2–48 and Nos. 50–137 can also be synthesized by a similar method.

Example 2

Preparation of Compound No. 138: 3-fluoro-4-(1,1,2,2-tetrafluoroethoxy)-2'-fluoro-4'-(trans-4-(2-(trans-4-propylcyclohexyl)ethyl)cyclohexyl)biphenyl (the compound of formula (1) wherein m is 1, Rf is —OCF$_2$CF$_2$H, Ra is C$_3$H$_7$—(3), A$_0$ and A$_3$ are a F-substituted 1,4-phenylene group (Be(3F)), both A$_1$ and A$_2$ are a trans-1,4-cyclohexylene group (Hx), Z$_1$ is —CH$_2$CH$_2$—, and both Z$_2$ and Z$_3$ are a single bond)

2.8 g (7.5 mmol) of 2-fluoro-4-(trans-4-(2-(trans-4-propylcyclohexyl)ethyl)cyclohexyl)phenyl boronic acid, 1.7 g (5.8 mmol) of 3-fluoro-4-(1,1,2,2-tetrafluoro)-bromobenzene, 2.1 g (15.0 mmol) of K$_2$CO$_3$, 0.05 g of 5%-Pd/C, 5 ml of water and 20 ml of a mixed solvent of ethanol/toluene (1/1) were refluxed for 14 hours. 50 ml of toluene was added to the reaction mixture, and the resulting organic layer was washed with water three times and dried over anhydrous magnesium sulfate. The solvent was distilled off under reduced pressure, and the residue was subjected to a silica gel column chromatography (eluent: heptane/ethyl acetate) to afford 2.3 g of the crude 3-fluoro-4-(1,1,2,2-tetrafluoroethoxy)-2'-fluoro-4'-(trans-4-(2-(trans-4-propylcyclohexyl)ethyl)cyclohexyl)biphenyl, which was then recrystallized from a mixed solvent of ethanol/ethyl acetate to give 1.3 g of the title compound (Compound No. 138). Yield: 42.5%

This compound exhibited a liquid crystal phase having the phase transition temperature:

C 81.5 SX 108.7 N 240.7 Iso

Each of the spectrum data well identified the structure thereof.

MS: 540 (M$^+$);

$^1$H-NMR (CDCl$_3$, TMS Internal standard): δ (ppm): 0.79–2.51 (m, 31H); 5.98 (tt, 1H); 6.95–7.44 (m, 6H)

The Compounds Nos. 239, 254 and 259 were synthesized according to the method of Example 2.

Compound No. 239: C$_5$H$_{11}$—Be—Hx—C$_2$H$_4$—Be—Be(3F)—OCF$_2$CF$_2$H

C 59.8 SX 164.9 N 192.3 Iso

Compound No. 254: C$_3$H$_7$—Hx—Hx—C$_2$H$_4$—Be—Be(3F)—OCF$_2$CF$_2$H

C 67.2 SB 153.7 N 247.7 Iso

Compound No. 259: C$_3$H$_7$—Hx—Hx—C$_2$H$_4$—Be—Be(3,5F)—OCF$_2$CF$_2$H

C 68.4 SX 80.2 SB 108.0 N 241.6 Iso

The Compounds Nos. 139–414 other than the above-exemplified compounds can also be synthesized according to the method of Example 2.

B) Liquid Crystal Compositions

The followings are examples of the liquid crystal compositions comprising the liquid crystalline compounds according to the present invention.

In each use example, NI represents a nematic phase—isotropic phase transition temperature (° C.), $\Delta\epsilon$ represents a dielectric anisotropy value, $\Delta n$ represents an optical anisotropy value, $\eta$ represents a viscosity at 20° C. (mPa.s), and Vth represents a threshold voltage (V).

Example 3 (Use Example 1)

The liquid crystal composition comprising the following cyanophenylcyclohexane liquid crystalline compounds:

| | |
|---|---|
| 4-(trans-4-propylcyclohexyl)benzonitrile | 24% |
| 4-(trans-4-pentylcyclohexyl)benzonitrile | 36% |
| 4-(trans-4-heptylcyclohexyl)benzonitrile | 25% |
| 4-(trans-4-pentylcyclohexyl)-4'-cyanobiphenyl | 15% | has the following physical properties.

NI: 71.7, $\Delta\epsilon$: 11.0, $\Delta n$: 0.137, $\eta$: 27.0

Vth: 1.78 at a cell thickness of 9 $\mu m$

85% of the above composition was mixed with 15% of Compound No. 1 prepared in Example 1: 3-fluoro-4-(1,1,2,3,3,3-hexafluoropropoxy)-2'-fluoro-4'-(2-(4-propylphenyl)ethyl)biphenyl to afford a liquid crystal composition with the following physical properties:

NI: 67.7, $\Delta\epsilon$: 10.9, $\Delta n$: 0.137, $\eta$: 34.0

Vth: 1.65 at a cell thickness of 9.2 $\mu m$

This composition was allowed to stand in a freezer at $-20°$ C., but neither smectic phase nor deposition of crystals was observed even after 60 days lapsed.

Example 4 (Use Example 2)

The liquid crystal composition of Composition Example 1 had the following physical properties:

NI: 112.7, $\Delta\epsilon$: 5.5, $\Delta n$: 0.104, $\eta$: 36.0

Vth: 2.15 at a cell thickness of 9.0 $\mu m$

This composition was allowed to stand in a freezer at $-20°$ C., but neither smectic phase nor deposition of crystals was observed even after 60 days lapsed.

Example 5 (Use Example 3)

The liquid crystal composition of Composition Example 2 had the following physical properties:

NI: 90.3, $\Delta\epsilon$: 4.3, $\Delta n$: 0.100, $\eta$: 28.0

Vth: 2.05 at a cell thickness of 5.0 $\mu m$

This composition was allowed to stand in a freezer at $-20°$ C., but neither smectic phase nor deposition of crystals was observed even after 60 days lapsed.

Example 6 (Use Example 4)

The liquid crystal composition of Composition Example 3 had the following physical properties:

NI: 83.3, $\Delta\epsilon$: 6.2, $\Delta n$: 0.114, $\eta$: 29.9

Vth: 1.89 at a cell thickness of 9.0 $\mu m$

This composition was allowed to stand in a freezer at $-20°$ C., but neither smectic phase nor deposition of crystals was observed even after 60 days lapsed.

Example 7 (Use Example 5)

The liquid crystal composition of Composition Example 4 had the following physical properties:

NI: 73.1, $\Delta\epsilon$: 8.9, $\Delta n$: 0.085, $\eta$: 30.2

Vth: 1.54 at a cell thickness of 9.0 $\mu m$

This composition was allowed to stand in a freezer at $-20°$ C., but neither smectic phase nor deposition of crystals was observed even after 60 days lapsed.

Example 8 (Use Example 6)

The liquid crystal composition of Composition Example 5 had the following physical properties:

NI: 75.7, $\Delta\epsilon$: 12.1, $\Delta n$: 0.084, $\eta$: 34.5

Vth: 1.10 at a cell thickness of 5.0 $\mu m$

This composition was allowed to stand in a freezer at $-20°$ C., but neither smectic phase nor deposition of crystals was observed even after 60 days lapsed.

Example 9 (Use Example 7)

The liquid crystal composition of Composition Example 6 had the following physical properties:

NI: 114.0, $\Delta\epsilon$: 6.2, $\Delta n$: 0.107, $\eta$: 29.3

Vth: 2.18 at a cell thickness of 9.0 $\mu m$

This composition was allowed to stand in a freezer at $-20°$ C., but neither smectic phase nor deposition of crystals was observed even after 60 days lapsed.

Example 10 (Use Example 8)

The liquid crystal composition of Composition Example 7 had the following physical properties:

NI: 86.1, $\Delta\epsilon$: 3.9, $\Delta n$: 0.082, $\eta$: 22.5

Vth: 2.06 at a cell thickness of 5.0 $\mu m$

This composition was allowed to stand in a freezer at $-20°$ C., but neither smectic phase nor deposition of crystals was observed even after 60 days lapsed.

Example 11 (Use Example 9)

The liquid crystal composition of Composition Example 8 had the following physical properties:

NI: 100.7, $\Delta\epsilon$: 8.5, $\Delta n$: 0.135, $\eta$: 19.8

Vth: 2.13 at a cell thickness of 9.0 $\mu m$

This composition was allowed to stand in a freezer at $-20°$ C., but neither smectic phase nor deposition of crystals was observed even after 60 days lapsed.

Example 12 (Use Example 10)

The liquid crystal composition of Composition Example 10 had the following physical properties:

NI: 79.6, $\Delta n$: 0.129, $\eta$: 21.0

Vth: 1.82 at a cell thickness of 9.0 $\mu m$

This composition was allowed to stand in a freezer at $-20°$ C., but neither smectic phase nor deposition of crystals was observed even after 60 days lapsed.

Example 13 (Use Example 11)

The liquid crystal composition of Composition Example 11 had the following physical properties:

NI: 99.0, $\Delta n$: 0.135, $\eta$: 19.3

Vth: 2.05 at a cell thickness of 9.0 $\mu m$

This composition was allowed to stand in a freezer at $-20°$ C., but neither smectic phase nor deposition of crystals was observed even after 60 days lapsed.

Example 14 (Use Example 12)

The liquid crystal composition of Composition Example 12 had the following physical properties:

NI: 85.1, Δn: 0.164, η: 35.0

Vth: 1.30 at a cell thickness of 9.0 μm

This composition was allowed to stand in a freezer at −20° C., but neither smectic phase nor deposition of crystals was observed even after 60 days lapsed.

INDUSTRIAL APPLICABILITY

The liquid crystalline compounds of the present invention have exceedingly high voltage holding ratio, low threshold voltage, and their exceedingly small temperature dependency. They are further characterized by high An, broad liquid phase temperature range and excellent compatibility with other liquid crystal materials, especially at low temperatures. In addition, suitable selection of a 6-membered ring, a substituent and/or a bond in the molecular constitutional elements of the liquid crystalline compounds can provide new liquid crystal compositions with desired physical properties.

What is claimed is:

1. A liquid crystalline compound comprising a fluoro-substituted alkyl ether compound represented by formula (1)

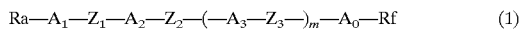
$$Ra-A_1-Z_1-A_2-Z_2-(-A_3-Z_3-)_m-A_0-Rf \qquad (1)$$

wherein m is 0 or 1; $A_0$, $A_1$, $A_2$ and $A_3$ represent a six-membered ring, ring $A_0$ is 1,4-phenylene which may be substituted with 1 to 3 of F and/or Cl, rings $A_1$, $A_2$, and $A_3$, independently of one another, are selected from trans-1,4-cyclohexylene, 1,4-phenylene which may be substituted with one or more halogen atoms, cyclohexene-1,4-diyl or 1,3-dioxane-2,5-diyl with the proviso that at least one of $A_1$, $A_2$ and $A_3$ is 1,3-dioxane-2,5-diyl; $Z_1$, $Z_2$, and $Z_3$ represent a bridge between the rings and independently of one another, are selected from —(CH$_2$)$_2$—, —(CH$_2$)$_4$—, —CH$_2$O—, —OCH$_2$— bonds, one or more hydrogen atoms in these bonds being optionally substituted with a halogen atom, or a single bond; Rf represents OCF$_2$CF$_2$H; and Ra is a straight- or branched monovalent organic radical of 1 to 20 carbons in which one or more hydrogen atoms in the radical may be substituted with a halogen atom and/or a cyano group, and in which one or more of —O—, —S—, —CO—, —CH=CH— or an ethynylene bond may be inserted in the radical, but two or more —O— and/or —S— are not adjacent to one another.

2. The liquid crystalline compound as claimed in claim 1 which is a tricyclic compound wherein m is 0.

3. The liquid crystalline compound as claimed in claim 1 which is a tetracyclic compound wherein m is 1.

4. The liquid crystalline compound as claimed in claim 1 wherein m is 0 and at least one of rings $A_1$ and $A_2$ is 1,4-phenylene which may be substituted with one or more halogen atoms, cyclohexene-1,4-diyl or 1,3-dioxane-2,5-diyl.

5. The liquid crystalline compound as claimed in claim 1 wherein m is 1 and ring $A_0$ is 1,4-phenylene which is substituted with F or Cl at 3-position.

6. A liquid crystal composition which comprises at least one of the liquid crystalline compounds represented by formula (1) as defined in claim 1.

7. A liquid crystal composition which comprises as a first component at least one of the liquid crystalline compounds represented by formula (1) as defined in claim 1, and as a second component at least one of the compounds represented by formula (2)

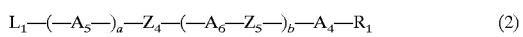
$$L_1-(-A_5-)_a-Z_4-(-A_6-Z_5-)_b-A_4-R_1 \qquad (2)$$

wherein a is 1 or 2, b is 0 or 1; $A_4$, $A_5$ and $A_6$ represent a six-membered ring, ring $A_4$ is 1,4-phenylene which may be substituted with one or two fluorine atoms, rings $A_5$ is trans-1,4-cyclohexylene, ring $A_6$ is trans-1,4-cyclohexylene, or 1,4-phenylene which may be substituted with one or more fluorine atoms; $Z_4$ and $Z_5$ represent a bridge between the rings and independently of one another, are selected from a single bond, —(CH$_2$)$_2$— or —CH=CH—; $R_1$ is selected from F, Cl, —OCF$_3$, —OCF$_2$H, —CF$_3$, —CF$_2$H or —CFH$_2$; and $L_1$ is an alkyl group of 1–10 carbons.

8. A liquid crystal composition which comprises as a first component at least one of the liquid crystalline compounds represented by formula (1) as defined in claim 1, and as a second component at least one of the compounds represented by formula (3)

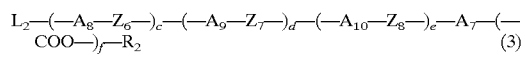
$$L_2-(-A_8-Z_6-)_c-(-A_9-Z_7-)_d-(-A_{10}-Z_8-)_e-A_7-(-COO-)_f-R_2 \qquad (3)$$

wherein c, d, e and f are independently of one another 0 or 1; $A_7$, $A_8$, $A_9$ and $A_{10}$ represent a six-membered ring, ring $A_7$ is trans-1,4-cyclohexylene or 1,4-phenylene which may be substituted with one or more fluorine atoms, rings $A_8$, $A_9$ and $A_{10}$, independently of one another, are selected from trans-1,4-cyclohexylene, 1,4-phenylene which may be substituted with one or more halogen atoms, cyclohexene-1,4-diyl, 1,3-dioxane-2,5-diyl or pyrimidine-2,5-diyl; $Z_6$, $Z_7$ and $Z_8$ represent a bridge between the rings and independently of one another, are selected from a single bond, —(CH$_2$)$_2$—, —COO—, —CH=CH—, ethynylene or 1-butene-3-ynylene; $R_2$ is selected from F, —OCF$_3$, —OCF$_2$H, —CF$_3$, —CF$_2$H, —CFH$_2$, —CN, a monovalent saturated organic radical of 1–10 carbons which may have one or more non-adjacent —O— in the radical, and a monovalent unsaturated organic radical of 2–10 carbons having —CH=CH at the terminal of the radical and/or in the radical in which one or more non-adjacent —O— may be inserted in the radical; $L_2$ is selected from a fluorine atom, a monovalent saturated organic radical of 1–10 carbons which may have one or more non-adjacent —O— in the radical, and a monovalent unsaturated organic radical of 2–10 carbons having —CH=CH at the terminal of the radical and/or in the radical in which one or more non-adjacent —O— may be inserted in the radical.

9. A liquid crystal composition which comprises a liquid crystal composition according to claim 8 in combination with a third component which is at least one of the compounds represented by formula (2)

$$L_1-(-A_5-)_a-Z_4-(-A_6-Z_5-)_b-A_4-R_1 \qquad (2)$$

wherein a is 1 or 2, b is 0 or 1; $A_4$, $A_5$ and $A_6$ represent a six-membered ring, ring $A_4$ is 1,4-phenylene which may be substituted with one or two fluorine atoms, rings $A_5$ is trans-1,4-cyclohexylene, ring $A_6$ is trans-1,4-cyclohexylene, or 1,4-phenylene which may be substituted with one or more fluorine atoms; $Z_4$ and $Z_5$ represent a bridge between the rings and independently of one another, are selected from a single bond, —(CH$_2$)$_2$— or —CH=CH—; $R_1$ is selected from F, Cl, —OCF$_3$, —OCF$_2$H, —CF$_3$, —CF$_2$H or —CFH$_2$; and $L_1$ is an alkyl group of 1–10 carbons.

10. A liquid crystal display device composed of the liquid crystal composition as claimed in any one of claims 6–8 and 9.

* * * * *